US010227356B2

(12) United States Patent
Kirkpatrick et al.

(10) Patent No.: US 10,227,356 B2
(45) Date of Patent: Mar. 12, 2019

(54) COMPOUNDS, COMPOSITIONS AND METHODS FOR INHIBITING CNKSR1

(71) Applicant: Phusis Therapeutics, Inc., San Diego, CA (US)

(72) Inventors: D. Lynn Kirkpatrick, Houston, TX (US); Martin Indarte, Buenos Aires (AR)

(73) Assignee: PHUSIS THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 15/133,789

(22) Filed: Apr. 20, 2016

(65) Prior Publication Data

US 2016/0304533 A1 Oct. 20, 2016

Related U.S. Application Data

(60) Provisional application No. 62/150,219, filed on Apr. 20, 2015.

(51) Int. Cl.

| | |
|---|---|
| ***C07D 403/14*** | (2006.01) |
| ***C07D 409/12*** | (2006.01) |
| ***C07D 317/66*** | (2006.01) |
| ***A61K 31/4184*** | (2006.01) |
| ***A61K 31/381*** | (2006.01) |
| ***A61K 31/36*** | (2006.01) |
| ***C07D 493/04*** | (2006.01) |
| ***C07D 413/14*** | (2006.01) |
| ***C07D 409/14*** | (2006.01) |
| ***C07D 417/14*** | (2006.01) |
| ***C07D 403/12*** | (2006.01) |
| ***C07D 405/12*** | (2006.01) |
| ***C07D 417/12*** | (2006.01) |
| ***C07D 317/46*** | (2006.01) |

(52) U.S. Cl.

CPC ......... *C07D 493/04* (2013.01); *C07D 317/46* (2013.01); *C07D 403/12* (2013.01); *C07D 405/12* (2013.01); *C07D 409/12* (2013.01); *C07D 409/14* (2013.01); *C07D 413/14* (2013.01); *C07D 417/12* (2013.01); *C07D 417/14* (2013.01)

(58) Field of Classification Search

CPC .. C07D 409/12; C07D 317/66; A61K 31/381; A61K 31/36

USPC .................. 549/60, 439; 514/444, 466, 394; 548/306.1

See application file for complete search history.

(56) References Cited

U.S. PATENT DOCUMENTS

| | | | |
|---|---|---|---|
| 3,821,222 | A | 6/1974 | Moore |
| 4,017,489 | A | 4/1977 | Lawrence |
| 4,251,528 | A | 2/1981 | Brittain et al. |
| 4,694,015 | A | 9/1987 | Sebille et al. |
| 4,939,140 | A | 7/1990 | Larsen et al. |
| 6,066,311 | A | 5/2000 | Cheetham et al. |
| 6,924,284 | B2 | 8/2005 | Beaton et al. |
| 9,340,532 | B2 * | 5/2016 | Kirkpatrick .......... C07D 417/14 |
| 2004/0092524 | A1 | 5/2004 | Perez et al. |
| 2004/0102360 | A1 | 5/2004 | Barnett et al. |
| 2004/0220182 | A1 | 11/2004 | Mujica-Fernaud et al. |
| 2007/0213378 | A1 | 9/2007 | Thomas et al. |
| 2007/0293516 | A1 | 12/2007 | Knight et al. |
| 2011/0144066 | A1 | 6/2011 | Mahadevan et al. |
| 2012/0059050 | A1 | 3/2012 | You et al. |
| 2012/0189670 | A1 | 7/2012 | Kirkpatrick et al. |
| 2013/0184317 | A1 | 7/2013 | Mahadevan et al. |
| 2014/0148400 | A1 | 5/2014 | Supuran et al. |
| 2015/0126563 | A1 | 5/2015 | Mahadevan et al. |
| 2015/0307482 | A1 | 10/2015 | Kirkpatrick et al. |

FOREIGN PATENT DOCUMENTS

| | | | |
|---|---|---|---|
| CA | 775563 | A | 1/1968 |
| DE | 2556011 | A1 | 6/1977 |
| DE | 3443225 | A1 | 6/1985 |
| EP | 2428504 | A1 | 3/2012 |
| EP | 2477625 | | 7/2012 |
| GB | 828963 | A | 2/1960 |
| JP | 2012522847 | A | 9/2012 |
| WO | WO 1990/15600 | A2 | 12/1990 |
| WO | WO 2000/18376 | A1 | 4/2000 |
| WO | WO 2002/083064 | A2 | 10/2002 |
| WO | WO 2003/076436 | A | 9/2003 |
| WO | WO 2003/084473 | A2 | 10/2003 |
| WO | WO 2005/090461 | A2 | 9/2004 |
| WO | WO 2005/000862 | A | 1/2005 |
| WO | WO 2005/005421 | A1 | 1/2005 |
| WO | WO 2005/097758 | A | 10/2005 |
| WO | WO 2006/046914 | A1 | 5/2006 |
| WO | WO 2007/039173 | A1 | 4/2007 |
| WO | WO 2008/083158 | A2 | 7/2008 |

(Continued)

OTHER PUBLICATIONS

Ohnuma, T. et al.: Synthetic studies on Mitomycins: the synthesis of Mitosene. Israel Journal of Chemistry, vol. 27, pp. 73-79, 1986.*

Baxter, I. et al.: Photolysis of t-butyl-substituted p-benzoquinone mono—or di-imine derivatives. Journal of the chemical society, section C, pp. 2604-2608, 1970.*

Anwar et al. "Reactions of some 5-aryl-2-thiono-1, 3, 4-thiadiazoles" Jan. 1, 1981, *Romanian Journal of Chemistry* 26(8): 1127-1134.

Banker et al. "Modern Pharmaceutics" 1979, *Marcel Dekker, Inc.*, New York (TOC).

Carpten et al. "A Transforming Mutation in the Pleckstrin Homology Domain of AKT1 in Cancer" Jul. 26, 2007, *Nature* 448(7152):439-444.

(Continued)

*Primary Examiner* — Charanjit Aulakh

(74) *Attorney, Agent, or Firm* — Pepper Hamilton LLP

(57) ABSTRACT

Compounds that inhibit CNKSR1, pharmaceutical compositions including compounds that inhibit CNKSR1 and methods of treating disease or disorders that respond to CNKSR1 inhibition are described herein. Additionally, methods of identifying inhibitors of CNKSR1 are described.

37 Claims, 17 Drawing Sheets

(56) References Cited

FOREIGN PATENT DOCUMENTS

| | | | |
|---|---|---|---|
| WO | WO 2009/129267 | A2 | 10/2009 |
| WO | WO 2010/085968 | A1 | 8/2010 |
| WO | WO 2011/032169 | A2 | 3/2011 |
| WO | WO 2014/093988 | A2 | 6/2014 |
| WO | WO 2016/172191 | A1 | 10/2016 |

OTHER PUBLICATIONS

Castillo et al. "Preferential Inhibition of Akt and Killing of Akt-dependent Cancer Cells by Rationally Designed Phosphatidylinositol Ether Lipid Analogues" Apr. 15, 2004, *Cancer Res.* 64(8):2782-92.
Catley et al. "Alkyl Phospholipids Perifosine Induces Myeloid Hyperplasia in a Murin Myeloma Model" Jul. 2007, *Exp. Hematol.* 35(7):1038-1046 (abstract).
Chemical Abstract Database compound (CAS RN 1022250-16-3) entering date May 25, 2008.
Chemical Abstract Database compound (CAS RN 1022557-01-2) entering date May 26, 2008.
Chemical Abstract Database: compound (CAS RN 477482-99-8), entering date Dec. 12, 2002.
Chemical Abstract Database: compound (CAS RN 477483-04-8), entering date Dec. 12, 2002.
Chemical Abstract Database: compound (CAS RN 919458-54-1), entering date Feb. 6, 2007.
Database Pubchem (Online) NCBI: Sep. 11, 2005 Database accession No. CID3800302.
Database Pubchem (Online) NCBI: Sep. 7, 2005 Database accession No. CID3268165.
Database Pubchem (Online) NCBI; Feb. 29, 2008 Database accession No. CID24283805.
Dhe-Paganon et al. "Crystal Structure of the Pleckstrin Homology-phosphotyrosine Binding (PH-PTB) Targeting Region of Insulin Receptor Substrate 1" Jul. 20, 1999, *PNAS USA* 96(15) : 8378-8383.
Du-Cuny et al. "Computational modeling of novel inhibitors targteting the Akt pleckstrin homology domain" Aug. 19, 2009, *Bioorganic & Medicinal Chemistry* 17(19):6983-6992.
European Search Report and Written Opinion dated Feb. 2, 2012 for EP 11181871.
Feldman et al. "Novel Small Molecule Inhibitors of 3'-phosphoinositide-dependent Kinsasel (PDK-1)" Sep. 30, 2004, *Eur. J. Cancer Supp.* 2(249):77.
Fengl "Enteric Coating" Oct. 22, 2002, *Enerex.ca* 5 pages.
Gills et al. "Spectrum of Activity and Molecular Correlates of Response to Phosphatidylinositol Ether Lipid Analogues, Novel Lipid-based Inhibitors of Akt" Mar. 2006, *Mol. Cancer Ther.* 5(3):713-722.
Giranda et al. "Novel ATP-competitive AKT Inhibitors Slow the Progression of Tumors in vivo" Sep. 30, 2004, *Eur. J. Cancer Supp.* 2(246):76-77.
Goodman et al. "The Pharmaceutical Basis of Therapeutics, $6^{th}$ ed." 1980, *MacMillan Publishing Co.*, New York (TOC).
Humphreys et al. "Toxicity and antileukemic effectiveness of pyridine derivatives and 1,3,4-thiadiazole derivatives in mice. Relationship to nicotinamide antagonism" 1962, *Cancer Res.* 22:483-550.
International Search Report and Written Opinion dated Jun. 3, 2014 for PCT/US2013/75505.
International Search Report and Written Opinion dated May 26, 2011 for PCT/US2010/048813.
International Search Report and Written Opinion dated Oct. 19, 2009 for PCT/US2009/040575.
International Search Report dated Dec. 15, 2009 for PCT/US2009/040575.
Kim et al. "Targeting the Phosphatidylinositol-3 Kinase/Akt Pathway for the Treatment of Cancer" Dec. 2005, *Curr. Opin. Investig. Drugs* 6(12):1250-1258.
Komander et al. "Structural Insights into the Regulation of Pdk1 by Phosphoinositides and Inositol Phosphates" 2004, *EMBO J.* 23(20):3918-3928.
Kumar et al. "AKT Crystal Structure and AKT-specific Inhibitors" Nov. 2005, *Oncogene* 24(50):7493-7501.
Li "Recent Progress in the Discovery of Akt Inhibitors as Anticancer Agents" 2007, *Expert Opin. Ther. Patents* 17:1077-1130.
Mahadevan et al. "Discovery of a novel class of AKT pleckstrin homology domain inhibitors" Sep. 2008, *Mol. Cancer Ther.* 7(9):2621-2632.
Mahieu et al. "Synthesis of new thiosulfonates and disulfides from sulfonyl chlorides and thiols" Jan. 1, 1986, *Synthetic Communications* 16(13):1709-1722.
Meuillet et al. "In Vivo Molecular Pharmacology and Antitumor Activity of the Targeted Akt Inhibitor PX-316" 2004, *Oncol. Res.* 14(10):513-527 (abstract).
Meuillet et al. "Specific Inhibition of the Akt2 Pleckstrin Homology domain by D-3-deoxy-phosphatidyl-myo-inositol Analogues" Apr. 2003, *Mol. Cancer. Ther.* 2(4):390-399.
Miyahara et al. "Antitumor activity of 2-Acylamino-1,3,4-thiadiazoles and related compounds" 1982, *Chem. Pharm. Bul.* 30(12):4402-4406.
Moses, et al., "In vitro and in vivo activity of novel small-molecule inhibitors targeting the pleckstrin homology domain of protein kinase B/AKT" Jun. 15, 2009, *Cancer Research* 69(12):5073-5081.
Office Action issued in Australian Application No. 2009236256, dated May 2, 2013.
Office Action issued in Australian Application No. 2009236256, dated Jun. 11, 2014.
Office Action issued in European Application No. 11181871.2, dated Jul. 10, 2013.
Office Action issued in European Application No. 11181871.2, dated Sep. 25, 2014.
Office Action issued in U.S. Appl. No. 12/937,898, dated Aug. 30, 2012.
Office Action issued in U.S. Appl. No. 12/937,898, dated Jun. 18, 2012.
Office Action issued in U.S. Appl. No. 13/789,209 dated Jun. 25, 2014.
Peng et al. "Dwarfism, Impaired Skin Development, Skeletal Muscle Atrophy, Delayed Bone Development, and Impeded Adipogenesis in Mice Lacking Akt1 and Akt2" Jun. 1, 2003, *Genes Dev.* 17(11):1352-1365.
Powell et al. "Bile Acid Hydrophobicity is Correlated with Induction of Apoptosis and/or Growth Arrest in HCT116 Cells" 2001, *Biochem J.* 356:481-486.
Runge et al. "Uber einige unsymmetrishce heterocyclische Disulfide, II" Jul. 1, 1963, *J. Fuer Praktische Chemie* 21(1-2):39-49 (cited in German/ no translation available).
Sassiver et al. "2-Sulfanilamido-5-methoxy-,1,3,4-thiadiazole and related compounds" 1966, *J. Med. Chem.* 9(4):541-545.
Stein et al. "Discovery and structure of activity relationships of sulfonamide ETA-selective antagonists" 1995, *J. Med. Chem.* 38:1344-1354.
Supplementary European Search Report and Written Opinion dated Sep. 17, 2012 for EP 10816289.
Supplementary European Search Report and Written Opinion dated Apr. 14, 2016 for EP13863280.
Thomas et al. "High-resolution Structure of Pleckstrin Homology Domain of Protein Kinase B/akt Bound to Phosphatidylinositol (3,4,5)-trisphosphate" Jul. 2002, *Curr. Biol.* 12(14):1256-1262.
International Search Report for PCT/US2016/028414 dated Jul. 29, 2016.

* cited by examiner

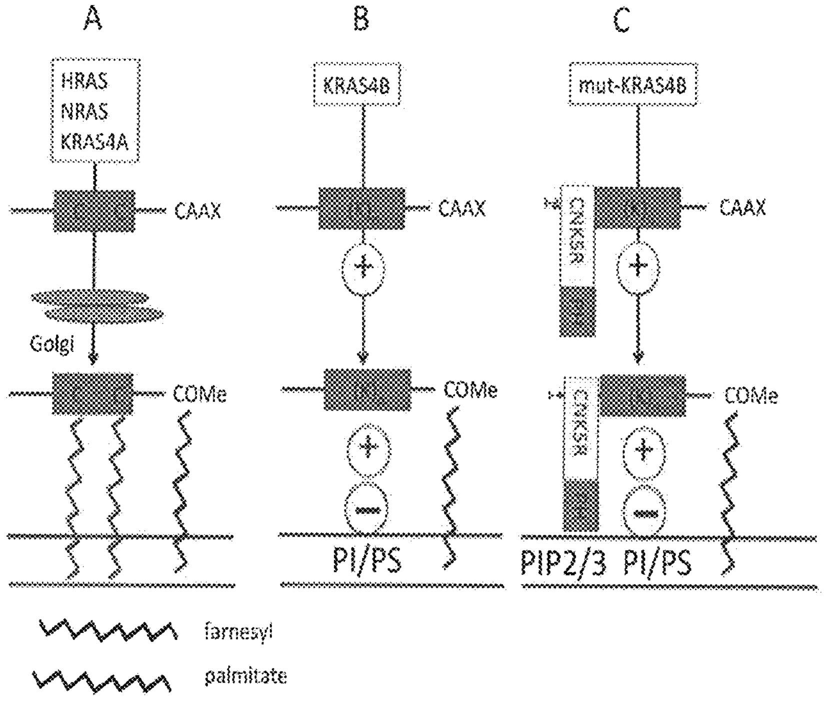

Figure 1

Role of CNKSR1 in mut-KRAS signaling. RAS undergo C-terminal CAAX farnesylation (or geranylgeranylation) followed by Rce1/ICMT processing. A, HRAS,NRAS and KRAS4A undergo hypervariable (hv) domain palmitoylation and Golgi processing leading to their lipid raft membrane localization. B, KRAS4B does not undergo Golgi processing and its polybasic hv domain binds to membrane PI and PS in specific lipid rafts. C, Without wishing to be bound it is believed that mut-KRAS but not wt-KRAS associates in a unique signaling nanocluster with the PH domain containing protein CNKSR1 to bind to PIP2/3 rich membrane lipid rafts necessary for mut-KRAS signaling

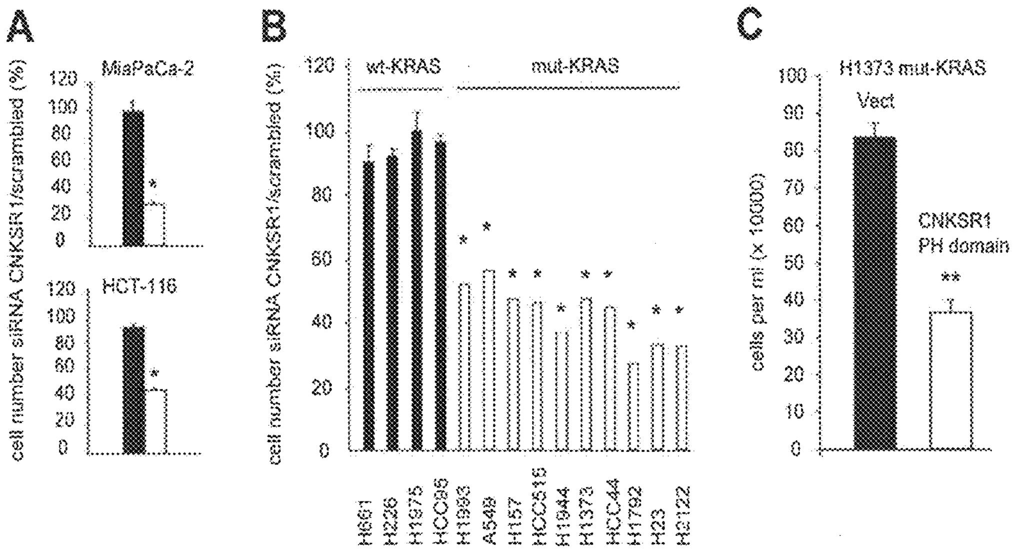

Figure 2

CNKSR1as a target for inhibition of mut-KRAS cell growth. A, Validation using CNKSR1 siRNA in MiaPaCa-2 and HCT-116 isogenic wt- and mut-KRAS cell lines. Filled boxes are wt-KRAS and open boxes mut-KRAS. Values are means of 3 determinations and bars are SE. * $p<0.05$. B,CNKSR1 siRNA in a panel of NSCLC cell lines with filled boxes showing wt-KRAS, and open boxes mut-KRAS cells. Values are expressed as a % relative to scrambled siRNA control. Bars are SE. * $p<0.05$ compared to scrambled siRNA. C Growth of H1373 mut-KRAS NSCLC cell line stably transfected with (closed boxes) vector alone or with (open boxes) a CNSKR1 PH domain construct that acts as a dominant negative inhibitor of cell growth. Bars are SE. ** $p<0.01$.

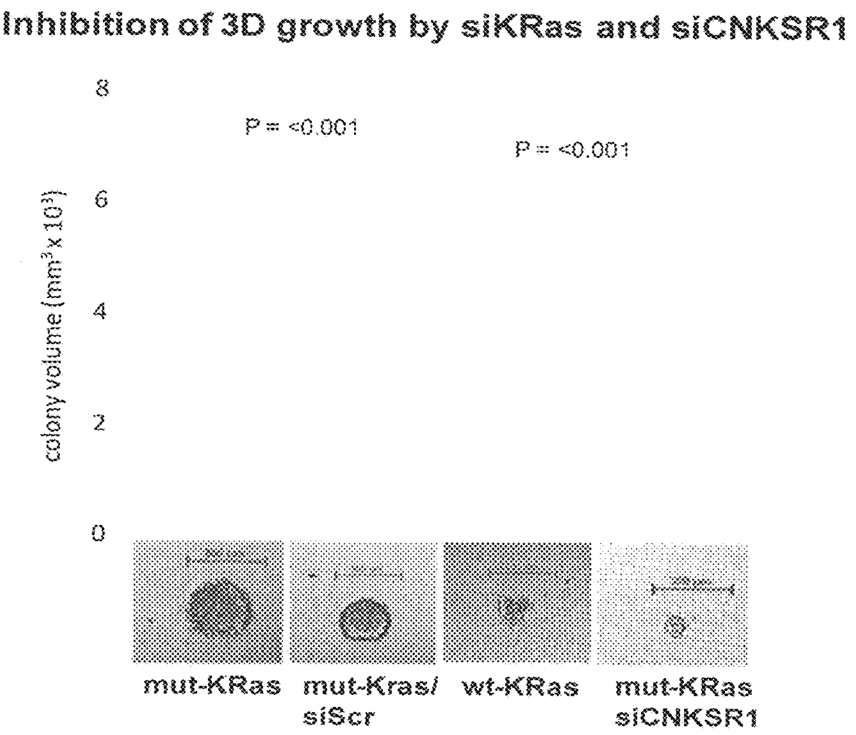

Figure 3

CNKSR1 is necessary for mut-KRAS anchorage independent cell growth

HCT-116 colon cancer cells (mutant-KRas G12D) (Mut-KRas) and the same cells with mutant-KRAS removed by homologous recombination leaving an allele of wild type-KRas (wt-KRas) were used for the study. siCNKSR1 or siscrambled siRNA as a control was reverse transfected into the cells 24 hr before plating. The cell number was optimized for plating for the best cell density and found to be 20,000 cells per ml. The lid was removed from a 96-well Greiner plate and turned upside down. 20 µl of the 20,000 cells per mL suspension was then added directly into the middle of the circles found on the lid of the 96-well plate forming a small drop. 100 µL of media was added into the corresponding wells, used to maintain the temperature of the drops, and the lid was flipped back over carefully placing it back onto the plate without disturbing the drop. The plate was then placed into the incubator for 3 days to allow the cells to migrate to the bottom of the drop due to gravity. After 3 days, 400 µL of media was added to the corresponding wells a SCIVAX 96-well plate. The lid from the Greiner 96-well plate was removed and placed onto the SCIVAX 22 plate allowing the drop to come in contact with the media and placed back into the incubator. After one hour, 200 µL of media was removed from the corresponding wells carefully without disturbing the spheroid and imaged using an IN Cell Analyzer 6000 is a high performance laser confocal imager (GE Healthcare). Colony volume was calculated by the formula: volume = (diameter x width$^2$). Bars are mean of 3 determinations and bars are S.E.

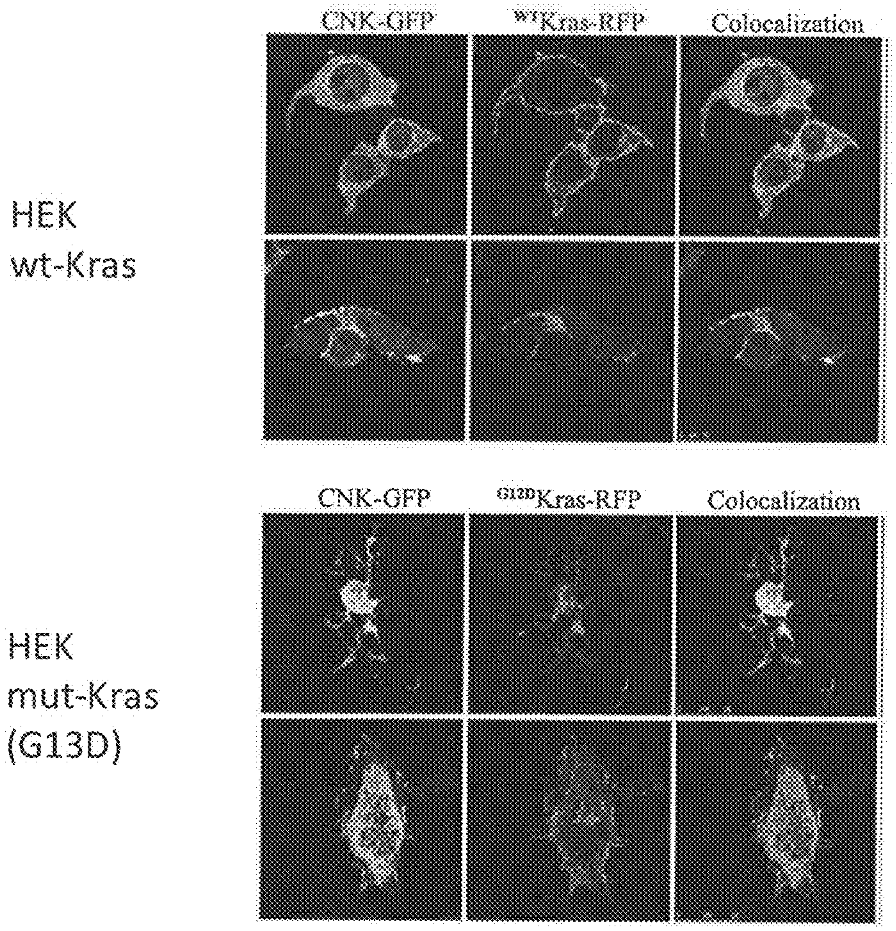

Figure 4

CNKSR1 (green) colocalizes with mutant-KRas (red) at the plasma membrane. HEK-293 cells were transfected with CNKSR1-GFP and mut-KRas(G13D) for 16 hr. Two photon confocal microscopy shows that CNKSR1 is located at the plasma membrane and the cytoplasm in both wt-KRas and mut-KRas cells. KRas tends to be more membrane associated When cell the images are merged CNKSR1 and wt-KRas can be seen to be colocalized (within 500 nm) shown by the yellow/orange color. Mut-KRas colocalization is also seen but is more diffuse. Note the transformed phenotype of the mut-KRas cells.

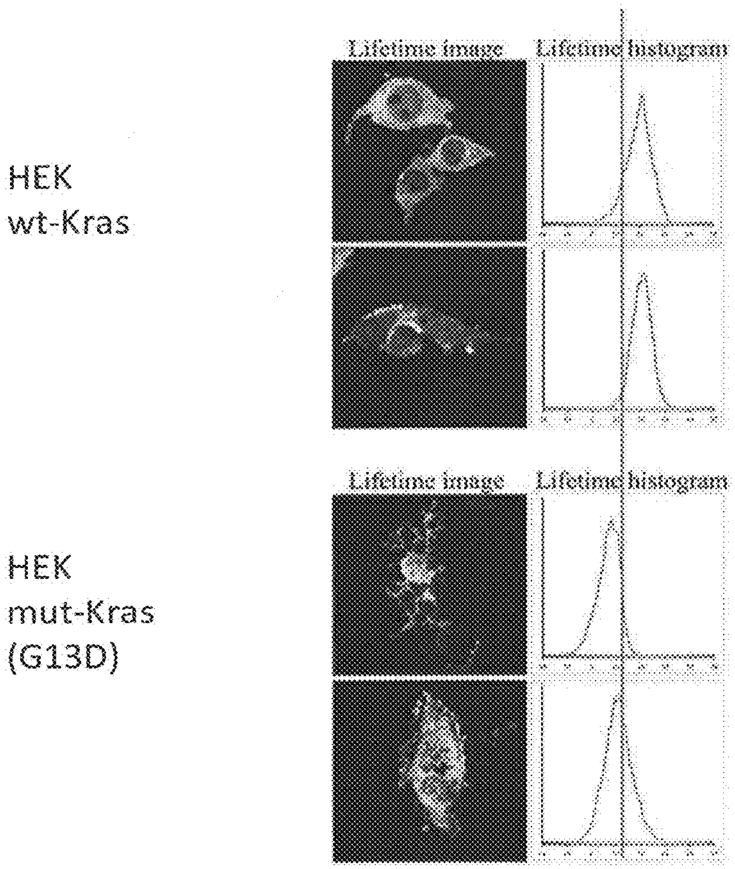

Figure 5

Fluorescence lifetime imaging microscopy (FLIM) showing that CNKSR1 binds directly to mut-KRas but not to wt-KRas in cells. HEK-293 cells were transfected with CNKSR1-GFP and mut-KRas(G13D and 16 hr later FLIM experiments were carried out using a Leica TCP SP5 inverted advanced confocal microscope system with internal photomultiplier tube (PMT) detector for TCSPC (time-correlated single-photon counting). The sample was excited with a tunable femtosecond (fs) titanium-sapphire laser with repetition rate of 80MHz and pulse width less then 80fs (Spectral Physics, Mai Tai BB). The wavelength used for two-photon excitation was 930 nm and the fluorescence was detected through a 525±25 nm interference filter. Images were obtained with oil-immersion objective (numerical aperture NA=1.4), a line scan speed of 400 Hz, with image size of 512x512 pixels. For FLIM analysis the pixels were reduced to 256x256. FLIM data was collected using Becker & Hickl SPC830 data and image acquisition card for TCSPC. The fluorescence decays were fitted with a single exponential decay model using Becker and 24 Hickl's SPCImage software and the GFP fluorescence lifetimes were calculated. The cell images in the left panel are two typical images false color for wt-KRas and mut-KRas cells and the fluorescence lifetimes shown on the right are for the entire cell measured by FLM. The results show a decrease in fluorescence lifetime in the right panel caused by when it CNKSR1 binds directly (i.e with a localization <100 nm) to mut-KRas but not to wt-KRas.

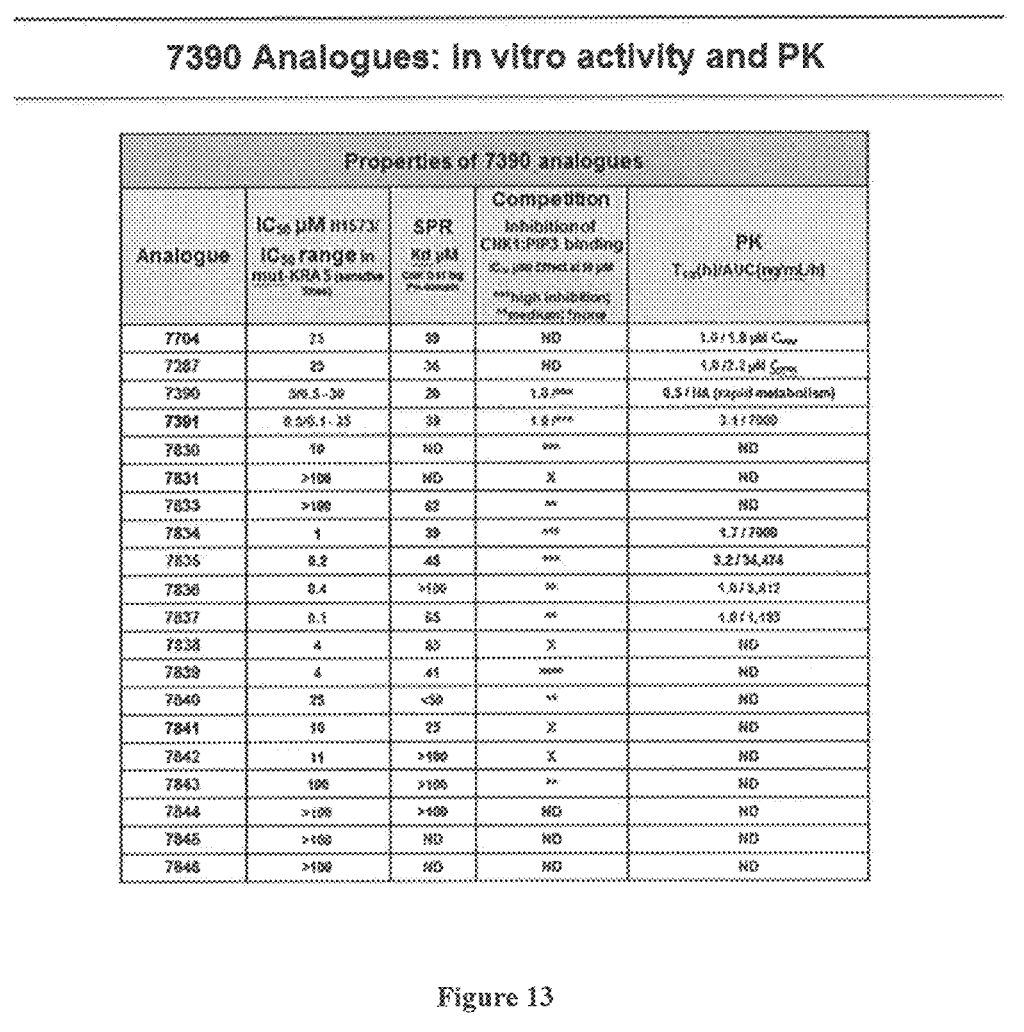

7390 Analogues: in vitro activity and PK

| Analogue | IC₅₀ µM H1573 IC₅₀ range in mut KRAS sensitive lines | SPR Kd µM cor 5:1 mg PX domain | Competition Inhibition of CRK1/P93 binding *** pic direct in pic ***high modulation ****medium hinse | PK T₁/₂(h)/AUC(ng·mL/h) |
|---|---|---|---|---|
| 7704 | 25 | 39 | ND | 1.9/1.8 µM C_max |
| 7287 | 20 | 36 | ND | 1.9/2.2 µM C_max |
| 7390 | 3/6.5-39 | 26 | 1.3,**** | 0.5/NA (rapid metabolism) |
| 7391 | 9.5/5.1-25 | 30 | 1.8,**** | 3.1/7X69 |
| 7830 | 10 | ND | *** | ND |
| 7831 | >100 | ND | X | ND |
| 7833 | >100 | 62 | ** | ND |
| 7834 | 1 | 39 | *** | 1.7/7068 |
| 7835 | 8.2 | 45 | *** | 3.2/34,474 |
| 7836 | 6.4 | >100 | ** | 1.8/3,812 |
| 7837 | 9.1 | 55 | ** | 1.8/1,183 |
| 7838 | 4 | 50 | X | ND |
| 7839 | 6 | 41 | **** | ND |
| 7840 | 23 | <50 | ** | ND |
| 7841 | 16 | 27 | X | ND |
| 7842 | 11 | >100 | X | ND |
| 7843 | 100 | >100 | ** | ND |
| 7844 | >100 | >100 | ND | ND |
| 7845 | >100 | ND | ND | ND |
| 7846 | >100 | ND | ND | ND |

Figure 13

COMPOUNDS, COMPOSITIONS AND METHODS FOR INHIBITING CNKSR1

CROSS REFERENCE TO RELATED APPLICATIONS

This application claims the benefit of U.S. Provisional Application No. 62/150,219, entitled "COMPOUNDS, COMPOSITIONS AND METHODS FOR INHIBITING CNKSR1" and filed on Apr. 20, 2015, the contents of which are incorporated by reference in their entirety as if fully set forth herein.

SUMMARY

Single point mutations of at least one of the RAS genes (KRAS, HRAS, and NRAS) are found in many human cancers, particularly in colon, lung and pancreatic cancer. RAS mutations are most commonly found in KRAS (about 85%), less commonly in NRAS (about 12%) and rarely in HRAS (about 3%). KRAS encodes two splice variants, A and B, with divergent C-terminal sequences due to the alternate utilization of exon 4. Mutant KRAS (mut-KRAS) may be present in up to about 25% of all human tumors. Mut-KRAS may play a critical role in driving tumor growth and resistance to therapy. An agent with even a modest effect on mut-KRAS activity, or one that exhibits selective inhibition of a subset of mut-RAS could have a major impact on therapy, and decrease cancer patient suffering and morbidity. Thus, finding new agents that inhibit the growth of mut-KRAS tumors is desirable.

Embodiments herein are directed to small molecule drugs that may inhibit CNKSR1 through PH-domain binding and may selectively block the growth of mut-KRAS cancer cells without affecting wt-KRAS cells. In embodiments, inhibiting the CNKSR1 protein may block the growth of mut-KRAS cancer cells without affecting wt-KRAS cancer cell growth. In embodiments, CNKSR1 has a PH-domain that may be critical for allowing mut-KRAS to signal tumor growth. In embodiments, iterative molecular modeling and the SPR binding approach may be used to identify PH-domain inhibitors.

Some embodiments provide a compound or a pharmaceutically acceptable salt or a stereoisomer or a solvate or a polymorph according to Formula I:

Formula I

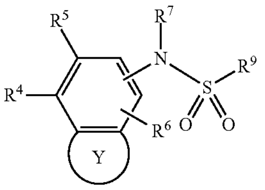

wherein

Y is a 3 to 10 membered optionally substituted heterocycle;

$R^4$ is hydrogen, halogen, hydroxy, —$C_1$-$C_4$ alkyl, —$C_1$-$C_4$ alkoxy, —$C_1$-$C_4$ perfluoroalkyl or optionally substituted $C_3$-$C_{10}$ heterocycle;

$R^5$ is —$C_1$-$C_4$ alkyl-OH, —$C_1$-$C_4$alkyl$R^8$, —$C_2$-$C_6$ alkenyl-OH, $C_1$-$C_4$ alkyl-$CO_2R^8$, $C_1$-$C_4$ alkenyl-$CO_2R^8$, —$C_1$-$C_4$ alkyl-C(O)—$C_1$-$C_4$ alkyl, —$C_2$-$C_6$ alkenyl-C(O)—$C_1$-$C_4$ alkyl, —$C_1$-$C_4$ alkyl-C(O)—$C_3$-$C_5$ cycloalkyl, —$C_2$-$C_6$ alkenyl-C(O)—$C_3$-$C_5$ cycloalkyl, NH—$SO_2$—$C_3$-$C_{10}$heteroaryl, C(O)—$C_2$-$C_6$alkenyl$R^8$,

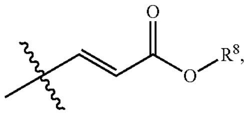,

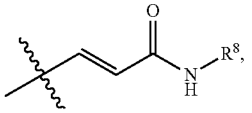,

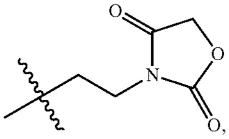,

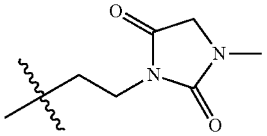,

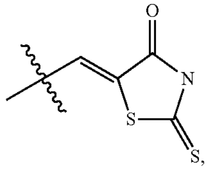,

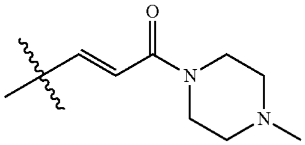,

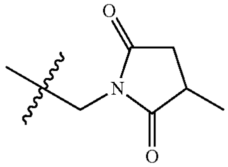,

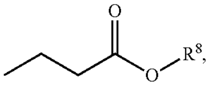,

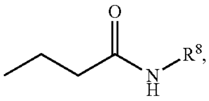,

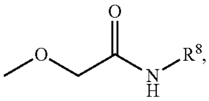,

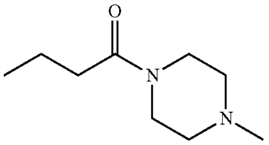,

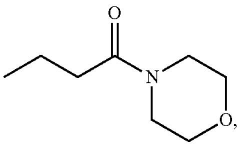,

-continued

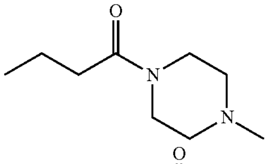

or

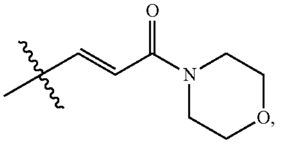

wherein $R^4$ and $R^5$ may be taken together to form a 5-10 membered, saturated, partially unsaturated or fully unsaturated heterocyclyl ring;

$R^6$ is hydrogen or —$C_1$-$C_4$alkoxy;

$R^7$ is -hydrogen or

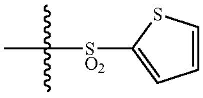

;

$R^8$, if present, is hydrogen, optionally substituted —$C_1$-C4 alkyl, —$C_3$-$C_5$ cycloalkyl or —$C_3$-$C_{10}$ heterocyclyl, wherein the —$C_1$-$C_4$ alkyl may be optionally substituted with —OH, —$C_3$-$C_{10}$heterocycle or —$C_3$-$C_{10}$ heteroaryl; and $R^9$ is optionally substituted $C_3$-$C_{10}$ aryl or optionally substituted $C_3$-$C_{10}$ heteroaryl. In embodiments, the compound or a pharmaceutically acceptable salt or a stereoisomer or a solvate or a polymorph according to Formula II, III or IV is further described herein.

Some embodiments provide pharmaceutical compositions comprising a compound according to an embodiment described herein and a pharmaceutically acceptable carrier or diluent. In embodiments, the compound may be present in a therapeutically effective amount.

Some embodiments provide a method of treating cancer comprising administering a therapeutically effective amount of a compound according to an embodiment described herein.

Some embodiments provide a method of inhibiting CNKSR1 comprising administering a therapeutically effective amount of a compound according to an embodiment described herein.

BRIEF DESCRIPTION OF DRAWINGS

The file of this patent contains at least one photograph or drawing executed in color. Copies of this patent with color drawing(s) or photograph(s) will be provided by the Patent and Trademark Office upon request and payment of necessary fee.

For a fuller understanding of the nature and advantages of the present invention, reference should be had to the following detailed description taken in connection with the accompanying drawings, in which:

FIG. 1 is a scheme illustrating translational modifications of RAS proteins, in accordance with embodiments.

FIG. 2 is a collection of plots illustrating the use of CNKSR1 as a target for inhibition of mut-KRAS growth, in accordance with embodiments.

FIG. 3 is an illustration of the inhibition of 3D growth by siKRas and siCNKSR1, in accordance with embodiments.

FIG. 4 is a collection of photographs depicting CNKSR1 colocalizes with mutant KRas at the plasma membranes, in accordance with embodiments.

FIG. 5 is a collection of photographs and lifetime histograms of Fluorescence lifetime imaging microscopy (FLIM) showing that CNKSR1 binds directly to mut-KRas but not to wt-KRas in cells in accordance with embodiments.

FIG. 13 is the in vitro activity of several CNK1 inhibitors.

DETAILED DESCRIPTION

Figure 6:
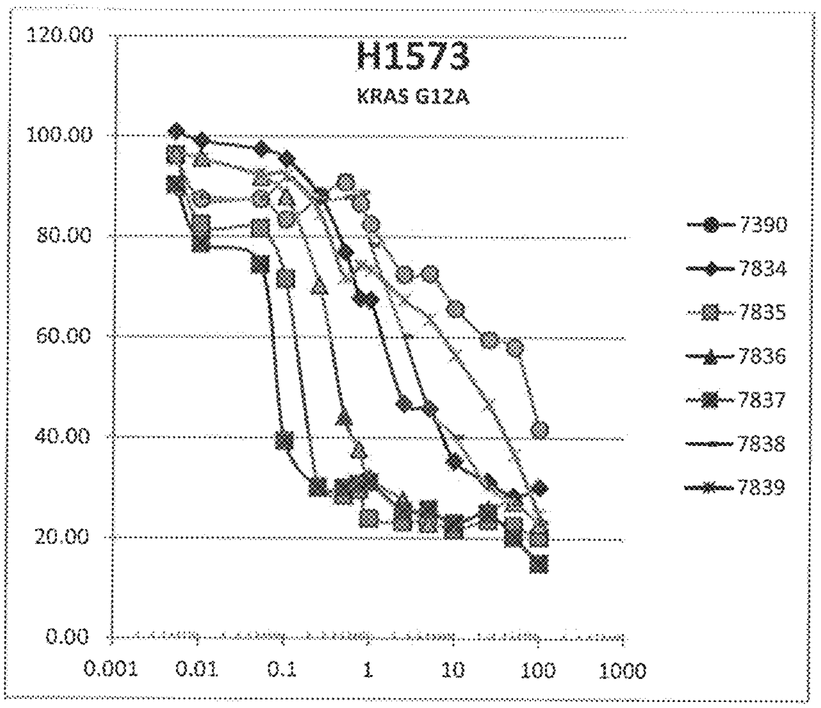
FIG. 6 is a graph depicting KRAS H1573 inhibition by certain compounds of the present application.
Figure 7:
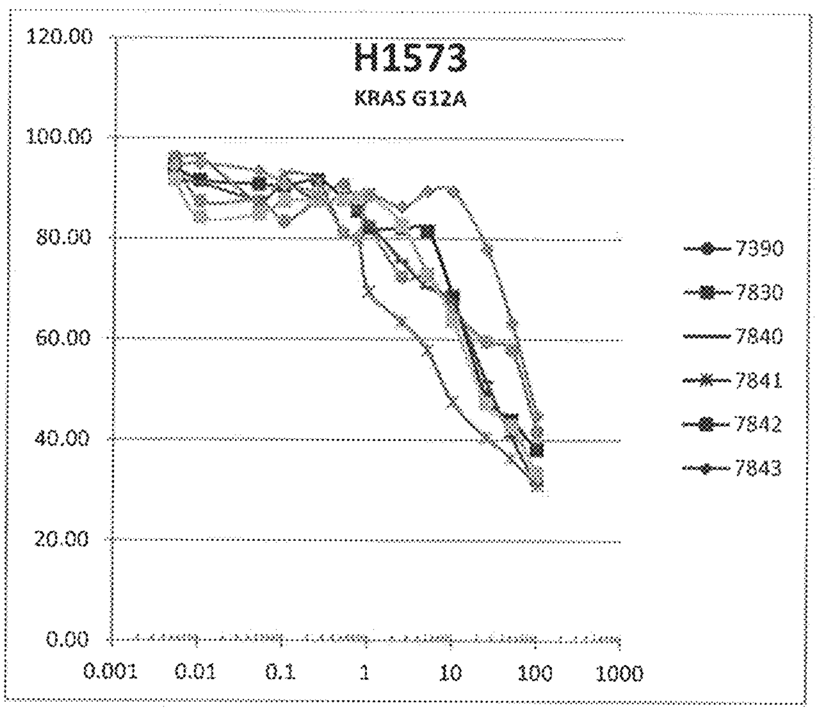
FIG. 7 is a graph depicting KRAS H1573 inhibition by certain compounds of the present application.
Figure 8:
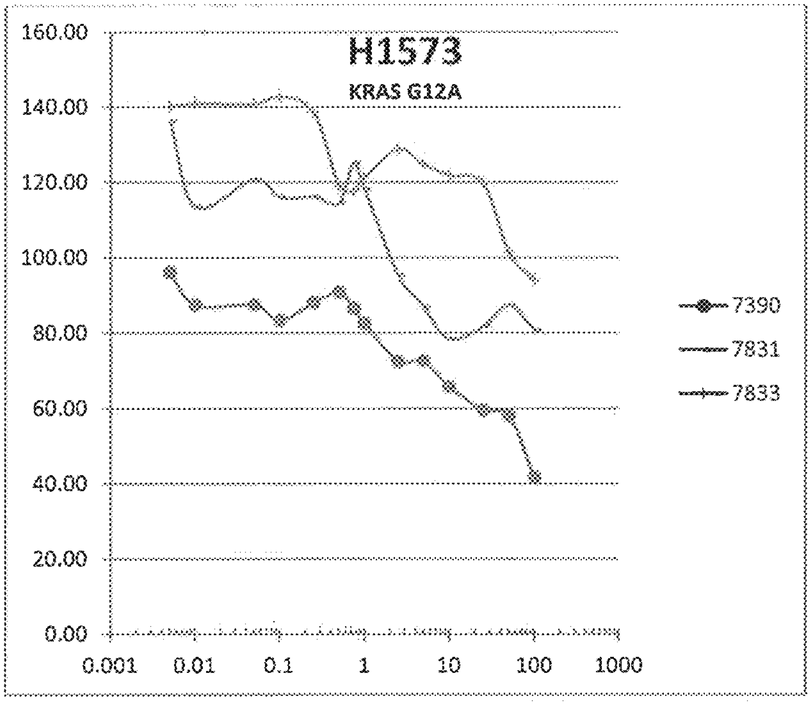
FIG. 8 is a graph depicting KRAS H1573 inhibition by certain compounds of the present application.
Figure 9:
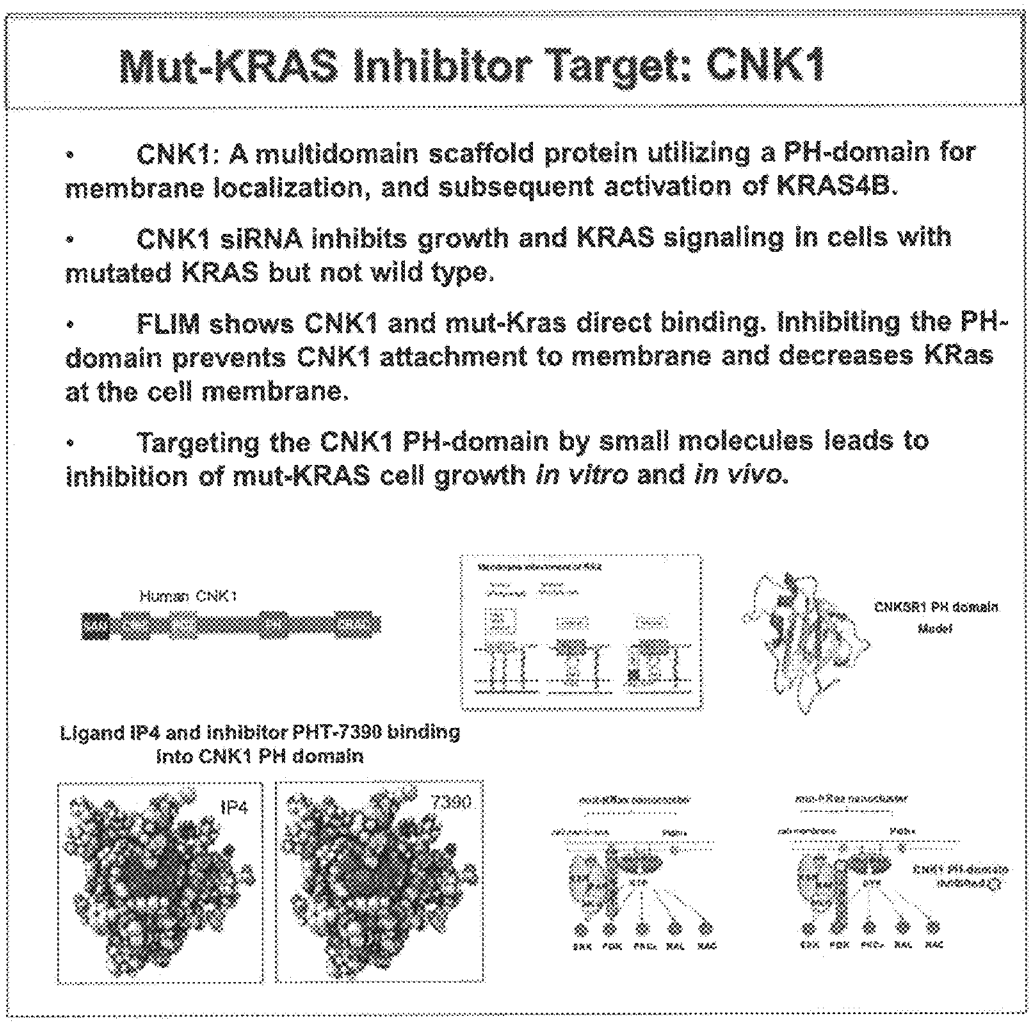
FIG. 9 is a description of the Mut-KRAS Inhibitor Target CNK1.
Figure 10:
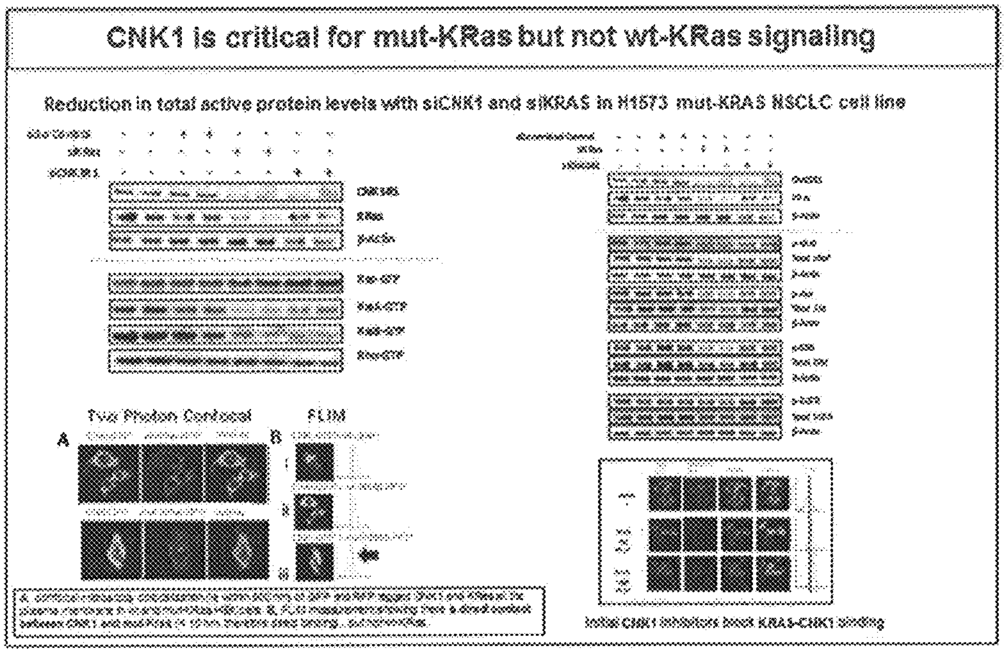
FIG. 10 is a description of why CNK1 is critical for Mut-KRAs targeting.
Figure 11:
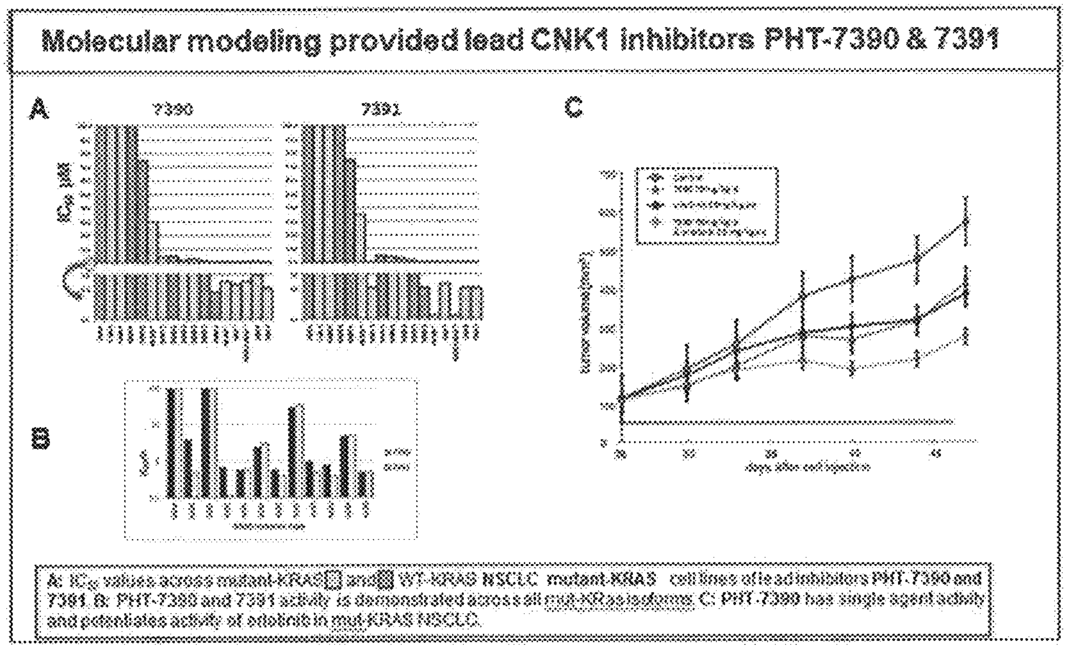
FIG. 11 is an illustration of two CNK1 inhibitors that were discovered through molecular modeling.
Figure 12:
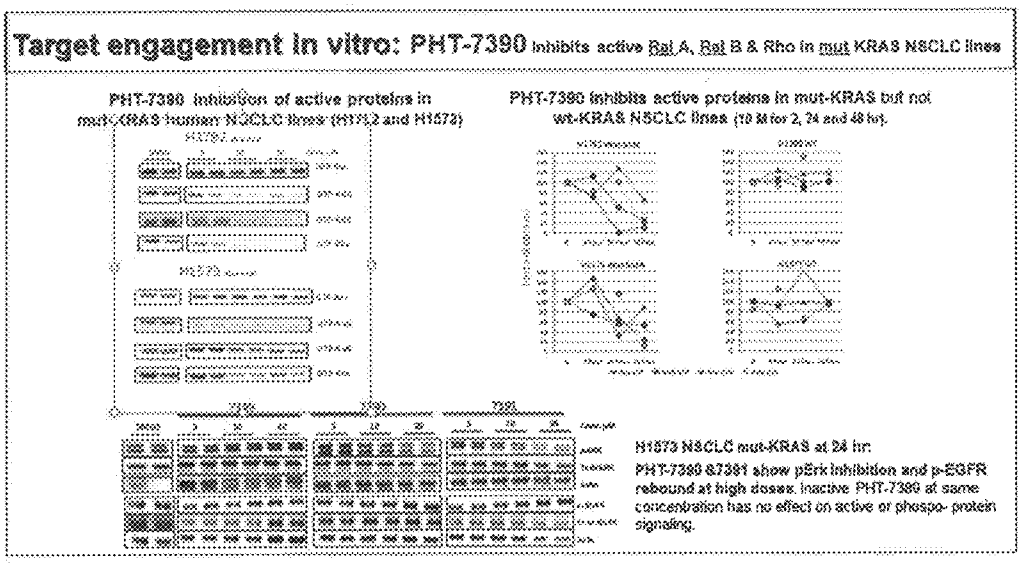
FIG. 12 is an illustration of Mut-KRAS inhibition.
Figure 14:
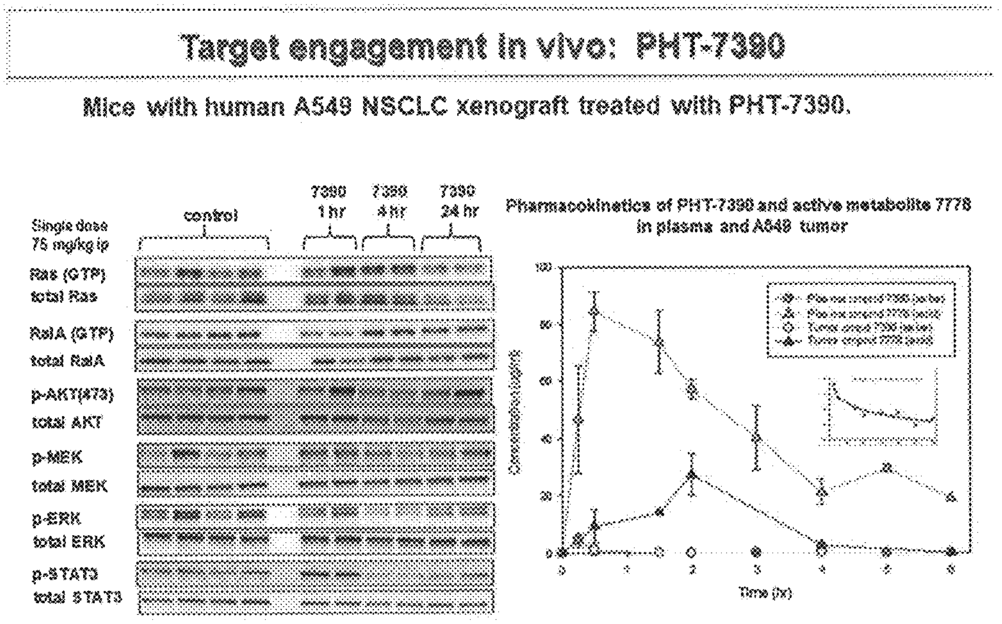
FIG. 14 is an illustration of a CNK1 inhibitor activity against human A549 NSCLC in a mouse model.
Figure 15:
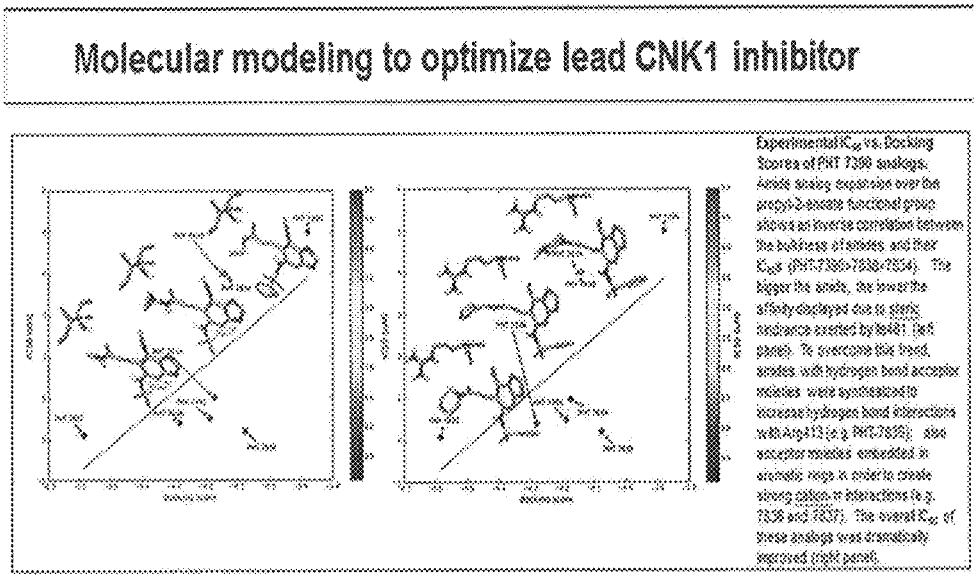
FIG. 15 is molecular modeling of a CNK1 inhibitor to yield further inhibitor candidates.
Figure 16:
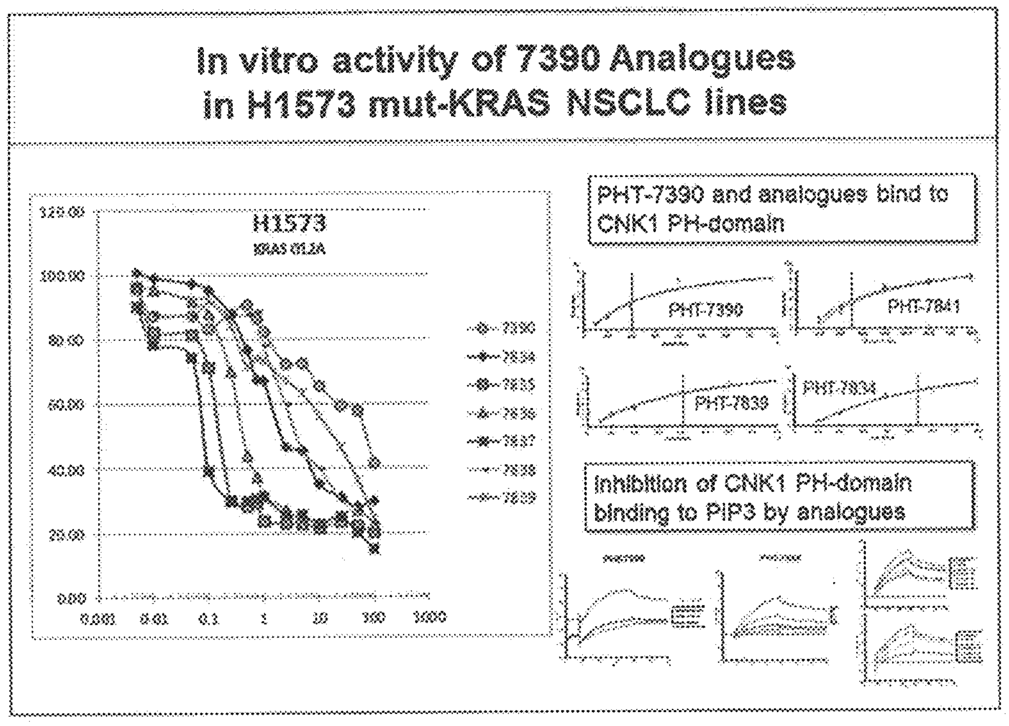
FIG. 16 is an illustration of CNK1 inhibitors against H1573 Mut-KRAS NSCLC in vitro.
Figure 17:
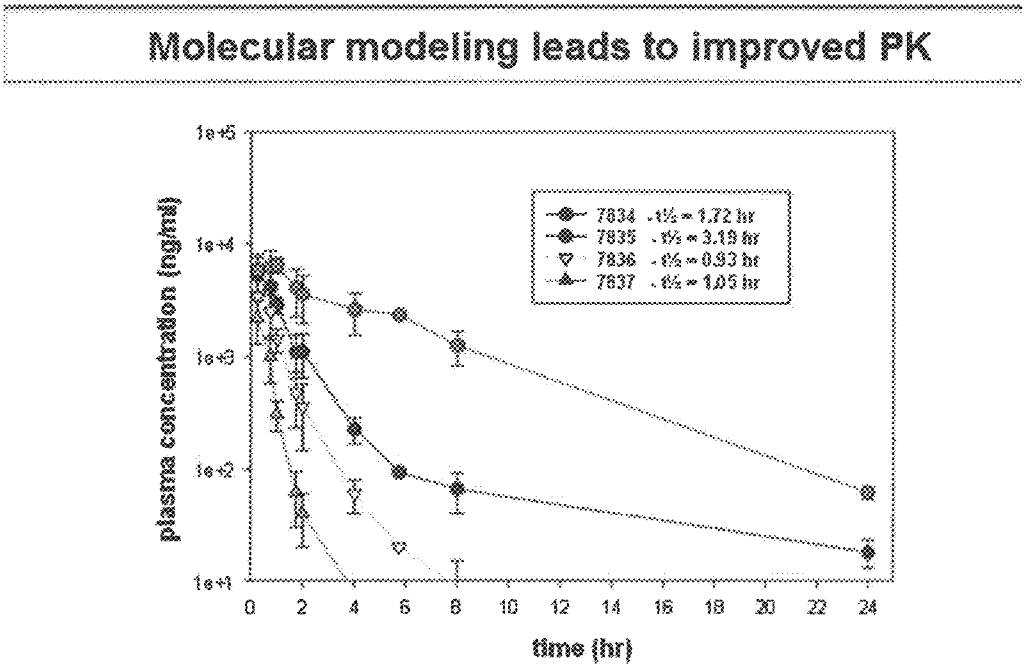
FIG. 17 is an illustration how molecular modeling yielded inhibitors with improved PK.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with a compound, can include, but is not limited to, providing a compound into or onto the target tissue; and/or providing a compound systemically to a patient by, e.g., intravenous injection or oral administration, whereby the therapeutic reaches the target tissue.

The term "animal" as used herein includes, but is not limited to, humans and non-human vertebrates such as wild, domestic and farm animals.

The term "inhibiting" includes the administration of a compound of the present invention to prevent the onset of the symptoms, alleviating the symptoms, or eliminating the disease, condition or disorder.

By "pharmaceutically acceptable", it is meant the carrier, diluent or excipient must be compatible with the other ingredients of the formulation and not deleterious to the recipient thereof.

As used herein, the term "therapeutic" means an agent utilized to treat, combat, ameliorate, prevent or improve an unwanted condition or disease of a patient. In part, embodiments of the present invention are directed to the treatment of cancer or the decrease in proliferation of cells. In some embodiments, the therapeutic may be a compound of embodiments herein, or a pharmaceutical composition comprising a compound of embodiments herein, and a pharmaceutically acceptable excipient.

A "therapeutically effective amount" or "effective amount" of a composition is a predetermined amount calculated to achieve the desired effect, i.e., to inhibit, block, or reverse the activation, migration, or proliferation of cells. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per day will normally fall within the range of from 0.001 to 10 mg/kg, more usually in the range of from 0.01 to 1 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

Single point mutations of at least one of the RAS genes (KRAS, HRAS, and NRAS) are found in many human cancers, particularly in colon, lung and pancreatic cancer. RAS mutations are most commonly found in KRAS (about 85%), less commonly in NRAS (about 12%) and rarely in HRAS (about 3%). KRAS encodes two splice variants, A and B, with divergent C-terminal sequences due to the alternate utilization of exon 4. Mutant KRAS (mut-KRAS) may be present in up to about 25% of all human tumors. Mut-KRAS may play a critical role in driving tumor growth and resistance to therapy. An agent with even a modest effect on mut-KRAS activity, or one that exhibits selective inhibition of a subset of mut-RAS could have a major impact on therapy, and decrease cancer patient suffering and morbidity. Thus, finding new agents that inhibit the growth of mut-KRAS tumors is arguably the most important unmet need in cancer therapy today.

Early attempts to develop GTP-competitive antagonists to RAS protein, analogous to ATP-competitive antagonists of protein-tyrosine kinases, were found to be impractical because of the picomolar binding of GTP to RAS. The next approach, and one that gained considerable traction, was to prevent the membrane binding of RAS by blocking RAS farnesylation using cell permeable CAAX peptidomimetics or small molecule farnesyl transferases (FT) inhibitors. Several potent agents were developed that showed dramatic activity in HRAS cell lines and mouse tumor models. However, it was found that the activity was limited to oncogenic HRAS which is found in only a small portion of human tumors, and that oncogenic NRAS and KRAS were resistant to FT inhibition because of alternative geranylgeranylation. Other efforts to develop antisense or siRNA inhibitors of KRAS, or inhibitors of Rcel and Icmt responsible for CAAX signal processing have so far not provided effective KRAS antitumor agents. The currently favored approach is to block downstream signaling targets activated by KRAS such as PI-3-K, RAF and mitogen activated protein kinase kinase (MEK), and several clinical trials underway with combinations of these inhibitors. However, a limitation of the approach may be that different mut-KRAS amino acid substitutions engage different downstream signaling effectors, and it may be necessary to have a number of inhibitors available for each of the pathways. It may be preferable to have an inhibitor that works with all forms of mut-KRAS and the adopted approach is to identify genes that are activators of mut-KRAS activity to provide molecular targets for the development of selective mut-KRAS inhibitors.

Following the strategy to identify genes that positively regulate mut-KRAS activity, CNKSR1 (connector enhancer of kinase suppressor of RAS 1) has been identified. The CNKSR1 protein is associated with KRAS in the membrane signaling nanocluster, and knockdown of CNKSR1 may cause inhibition of mut-KRAS tumor cell growth and signaling without inhibition of wt-KRAS cell growth. Furthermore, CNKSR1 has a potentially druggable pleckstrin homology (PH) domain.

Some embodiments provide a compound or a pharmaceutically acceptable salt or a stereoisomer or a solvate or a polymorph according to Formula I:

Formula I

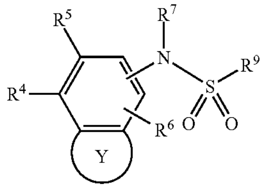

wherein

Y is a 3 to 10 membered optionally substituted heterocycle;

$R^4$ is hydrogen, halogen, hydroxy, —$C_1$-$C_4$ alkyl, —$C_1$-$C_4$ alkoxy, —$C_1$-$C_4$ perfluoroalkyl or optionally substituted $C_3$-$C_{10}$ heterocycle;

$R^5$ is —$C_1$-$C_4$ alkyl-OH, —$C_1$-$C_4$alkyl$R^8$, —$C_2$-$C_6$ alkenyl-OH, $C_1$-$C_4$ alkyl-$CO_2R^8$, $C_1$-$C_4$ alkenyl-$CO_2R^8$, —$C_1$-$C_4$ alkyl-C(O)—$C_1$-$C_4$ alkyl, —$C_2$-$C_6$ alkenyl-C(O)—$C_1$-$C_4$ alkyl, —$C_1$-$C_4$ alkyl-C(O)—$C_3$-$C_5$ cycloalkyl, —$C_2$-$C_6$ alkenyl-C(O)—$C_3$-$C_5$ cycloalkyl, NH—$SO_2$—$C_3$-$C_{10}$heteroaryl, C(O)—$C_2$-$C_6$alkenyl$R^8$,

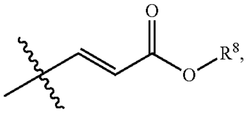

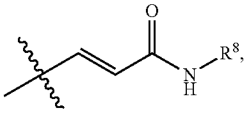

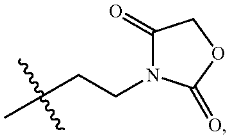

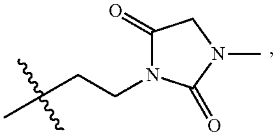

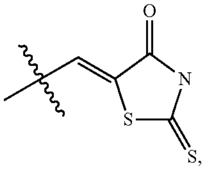

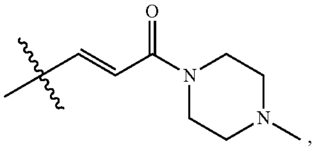

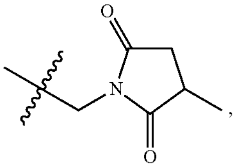

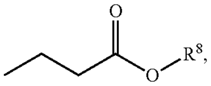

-continued

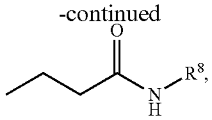

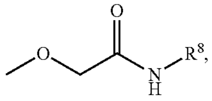

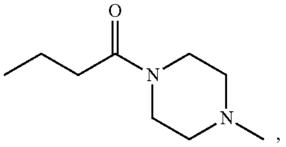

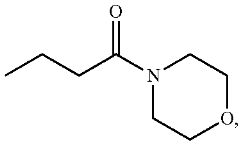

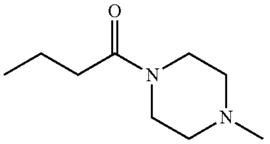

or

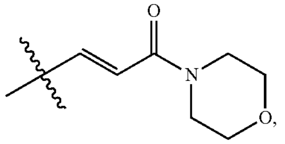

wherein $R^4$ and $R^5$ may be taken together to form a 5-10 membered, saturated, partially unsaturated or fully unsaturated heterocyclyl ring;

$R^6$ is hydrogen or —$C_1$-$C_4$alkoxy;

$R^7$ is -hydrogen or

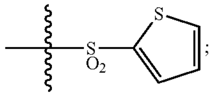 [SMILES: *S(=O)(=O)c1cccs1]

$R^8$, if present, is hydrogen, optionally substituted —$C_1$-C4 alkyl, —$C_3$-$C_5$ cycloalkyl or —$C_3$-$C_{10}$ heterocyclyl, wherein the —$C_1$-$C_4$ alkyl may be optionally substituted with —OH, —$C_3$-$C_{10}$ heterocycle or —$C_3$-$C_{10}$ heteroaryl; and $R^9$ is optionally substituted $C_3$-$C_{10}$ aryl or optionally substituted $C_3$-$C_{10}$ heteroaryl.

Further embodiments provide compounds, wherein $R^8$ is selected from the group consisting of:

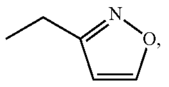

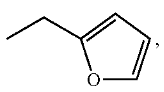

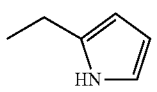

and

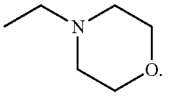

Further embodiments provide compounds according to Formula II:

Formula II

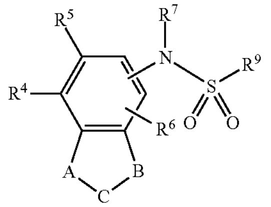

wherein

A and B are each independently —C—, —$CR^2$—, —C(O)—, —O—, —N—, —$NR^1$—, —S—, —S(O)— or —$S(O_2)$—;

C is —C—, —$CR^2$—, —$CR^2R^3$—, —$CR^2R^3$—$CR^2R^3$—, $CR^2$—N—, —C(O)—, —O—, —N—, —$NR^1$—, —S—, —S(O)— or —$S(O_2)$—;

$R^1$, if present, is hydrogen and $C_1$-$C_4$ alkyl;

$R^2$, if present, is hydrogen, halogen and $C_3$-$C_{10}$ heterocycle; and $R^3$, if present, is hydrogen and halogen.

Further embodiments provide compounds of Formula I or II, wherein $R^4$ is fluoro, methoxy or perfluoromethoxy.

Further embodiments provide compounds of Formula I or II, wherein $R^5$ is

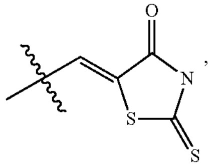, 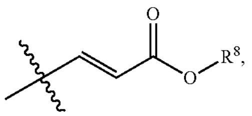

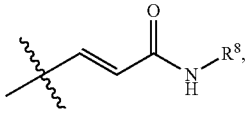

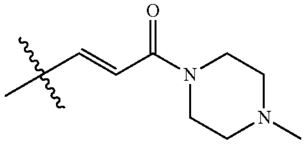, 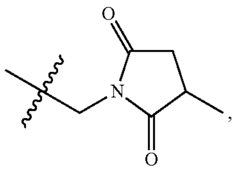,

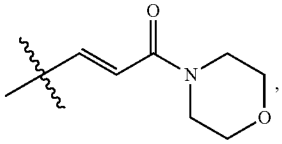, 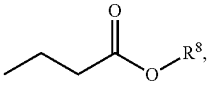

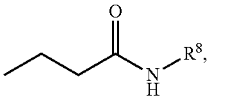 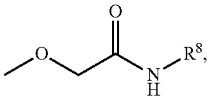

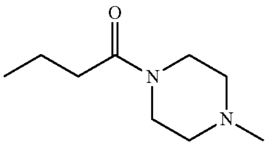, 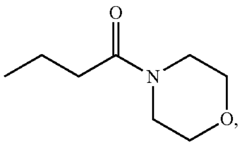

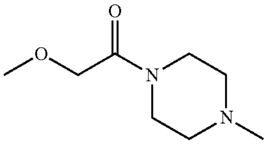,

C(O)—$C_2$-$C_6$alkenyl$R^8$ or —$C_2$-$C_6$ alkenyl-OH, when $R^5$ is

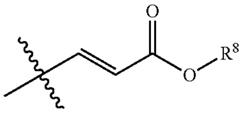

or —$C_2$-$C_6$ alkenyl-OH then A and B are each O and C is $CR^2R^3$.

Further embodiments provide compounds of Formula I or II, wherein $R^4$ and $R^5$ taken together form

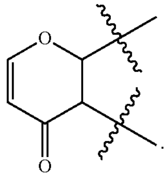 [SMILES: *C1OC=CC(=O)C1*]

Further embodiments provide compounds of Formula I or II, wherein $R^6$ is hydrogen or methoxy.

Further embodiments provide compounds of Formula I or II, wherein $R^7$ is hydrogen.

Further embodiments provide compounds of Formula I or II, wherein $R^8$ is hydrogen, methyl, ethyl, 2-hydroxypropyl, cyclopropyl, furan, methylfuran, methyl pyrrole, methylmorpholine, methylisoxazole, methylisoxazole or methyloxazole.

Further embodiments provide compounds of Formula I or II, wherein $R^9$ is optionally substituted phenyl, pyridine, pyrrole, thiophene, thiazole, oxazole, isoxazole, imidazole, indole or benzofuran.

Further embodiments provide compounds of Formula I or II, wherein A, B and C when taken together with the atoms to which they are attached form the following optionally substituted heterocycles:

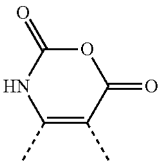, 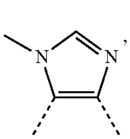, 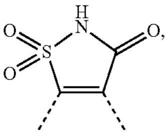

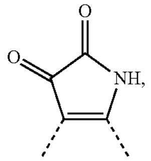 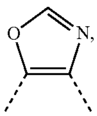 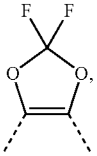

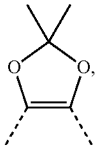 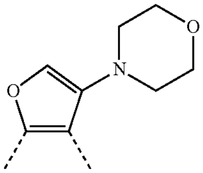, 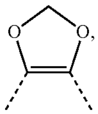

-continued

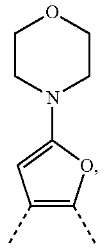

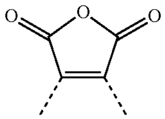

and

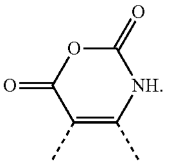

Further embodiments provide compounds according to Formula III:

Formula III

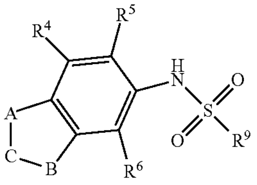

wherein $R^5$ is

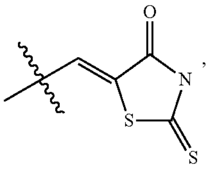,

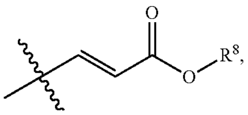

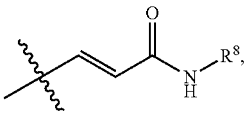

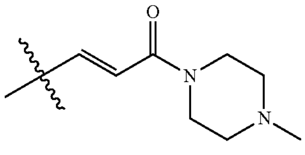,

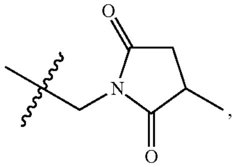,

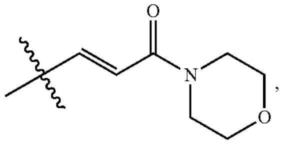,

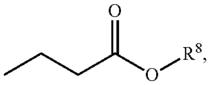

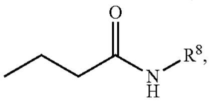

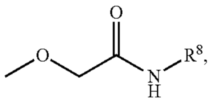

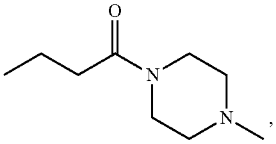,

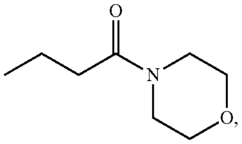

-continued

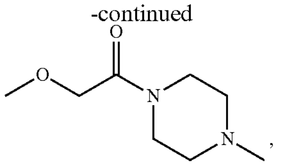,

C(O)—$C_2$-$C_6$alkenyl$R^8$ or —$C_2$-$C_6$ alkenyl-OH, when $R^5$ is

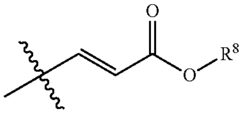

or —$C_2$-$C_6$ alkenyl-OH then A and B are each O and C is $CR^2R^3$.

Further embodiments provide compounds of Formula III, wherein A, B and C when taken together with the atoms to which they are attached form the following optionally substituted heterocycles:

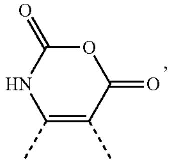,

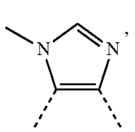,

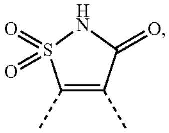

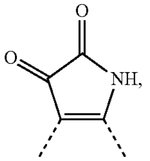

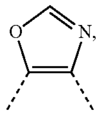

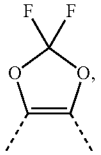

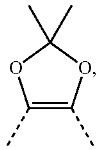

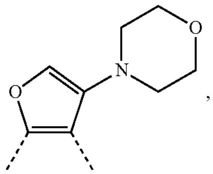,

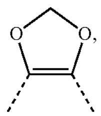

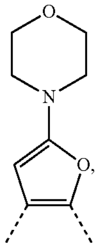

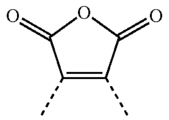

and

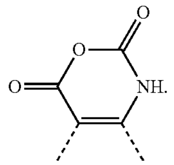

Further embodiments provide compounds of Formula III, wherein $R^4$ is fluoro, methoxy or perfluoromethoxy.

Further embodiments provide compounds of Formula III, wherein $R^4$ and $R^5$ taken together form

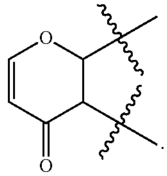 [SMILES: *C1OC=CC(=O)C1*]

Further embodiments provide compounds of Formula III, wherein $R^6$ is hydrogen or methoxy.

Further embodiments provide compounds of Formula III, wherein $R^7$ is hydrogen.

Further embodiments provide compounds of Formula III, wherein $R^8$ is hydrogen, methyl, ethyl, 2-hydroxypropyl, cyclopropyl, furan, methylfuran, methyl pyrrole, methylmorpholine, methylisoxazole or methyloxazole.

Further embodiments provide compounds of Formula III, wherein $R^9$ is optionally substituted phenyl, pyridine, pyrrole, thiophene, thiazole, oxazole, isoxazole, imidazole, indole or benzofuran.

Further embodiments provide compounds, according to Formula IV:

Formula IV

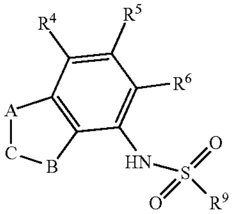

wherein $R^5$ is

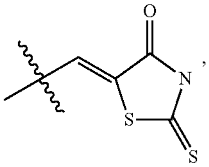,
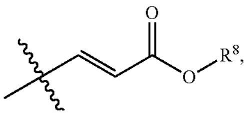,
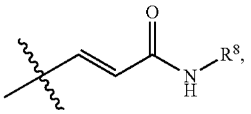,
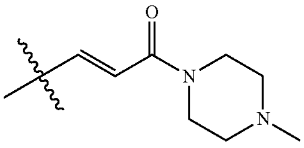,
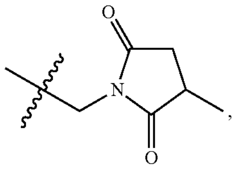,
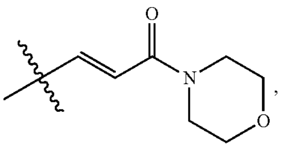,
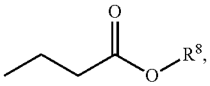,
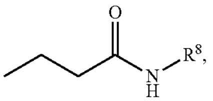,
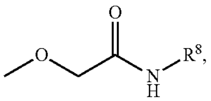, -continued

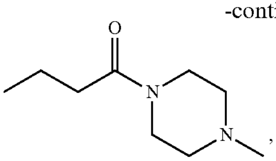,
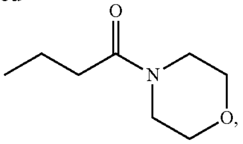,
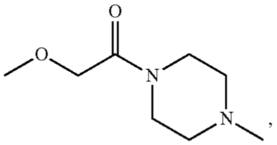,

C(O)—$C_2$-$C_6$alkenyl$R^8$ or $C_2$-$C_6$ alkenyl-OH, when $R^5$ is

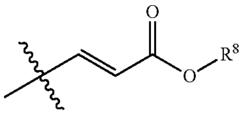

or —$C_2$-$C_6$ alkenyl-OH then A and B are each O and C is $CR^2R^3$.

Further embodiments provide compounds of Formula IV, wherein A, B and C when taken together with the atoms to which they are attached form the following optionally substituted heterocycles:

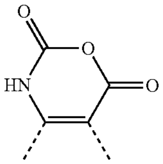,
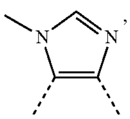,
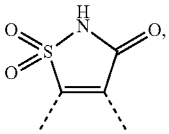,
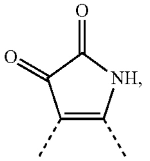,
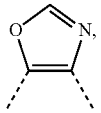,
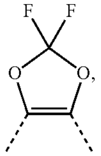,
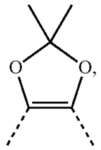,
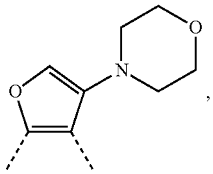,
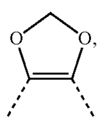,
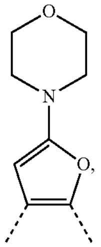,
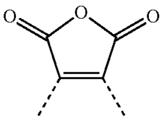

and

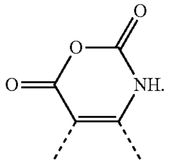.

Further embodiments provide compounds of Formula IV, wherein $R^4$ is fluoro, methoxy or perfluoromethoxy.

Further embodiments provide compounds of Formula IV, wherein $R^4$ and $R^5$ taken together form

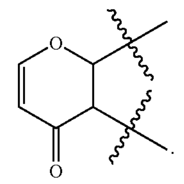 [SMILES: *C1OC=CC(=O)C1*]

Further embodiments provide compounds of Formula IV, wherein $R^6$ is hydrogen or methoxy.

Further embodiments provide compounds of Formula IV, wherein $R^7$ is hydrogen.

Further embodiments provide compounds, wherein $R^8$ is hydrogen, methyl, ethyl, 2-hydroxypropyl, cyclopropyl, furan, methylfuran, methyl pyrrole, methylmorpholine, methylisoxazole or methyl oxazole.

Further embodiments provide compounds of Formula IV, wherein $R^9$ is optionally substituted phenyl, pyridine, pyrrole, thiophene, thiazole, oxazole, isoxazole, imidazole, indole or benzofuran.

Some embodiments provide a compound selected from the group consisting of:

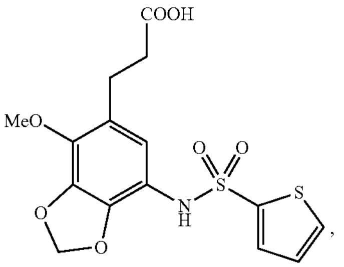

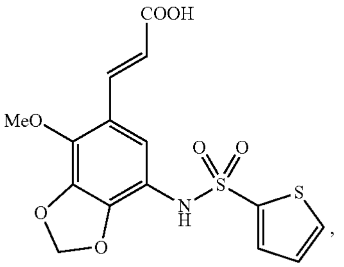

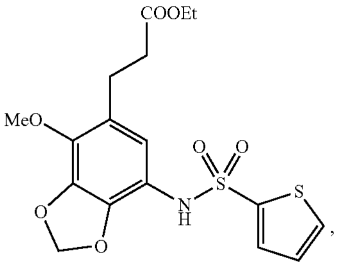

-continued

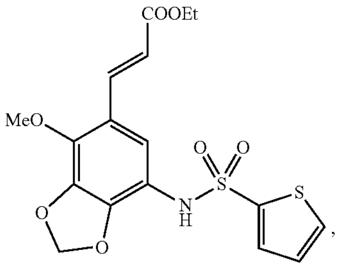

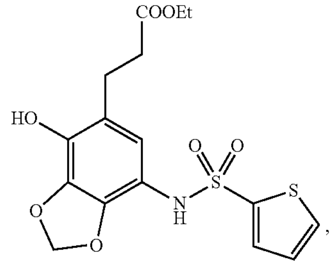

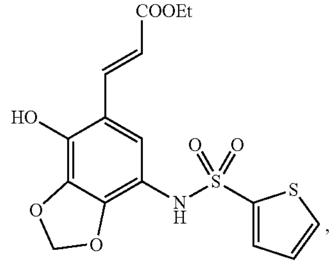

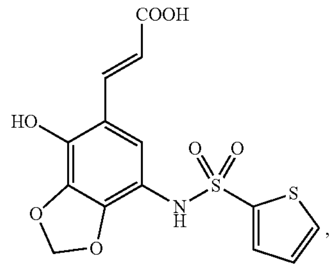

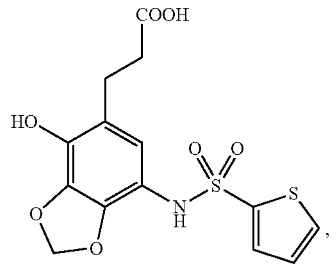

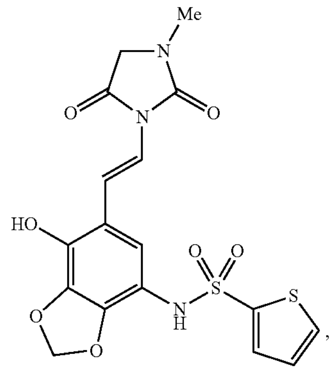

-continued
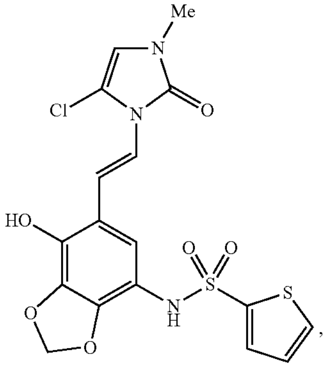
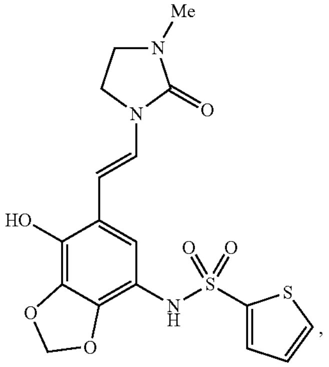
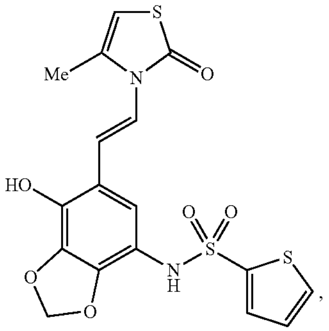
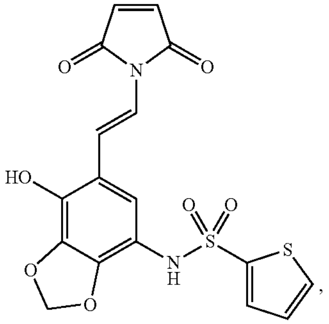
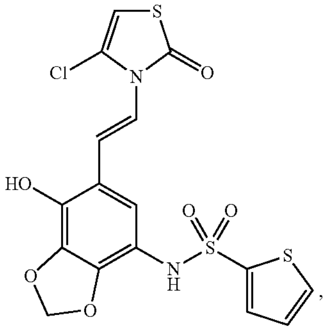
-continued
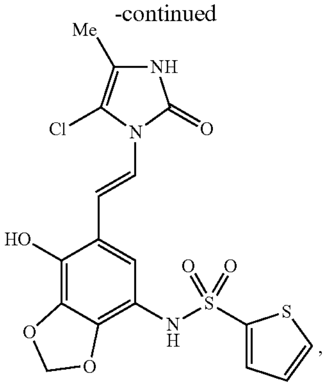
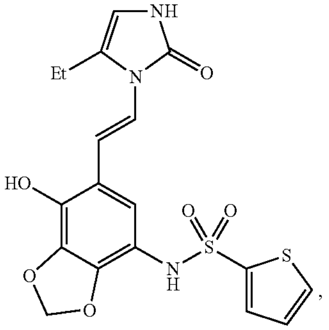
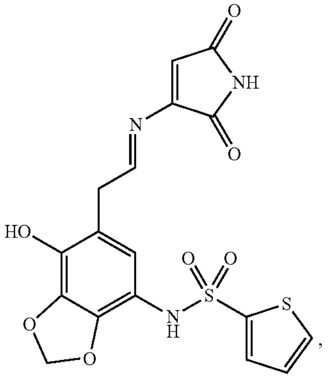
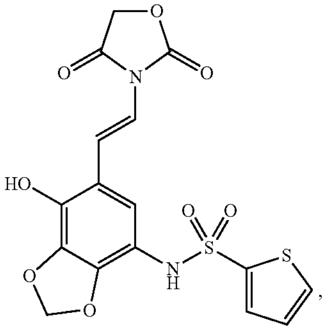
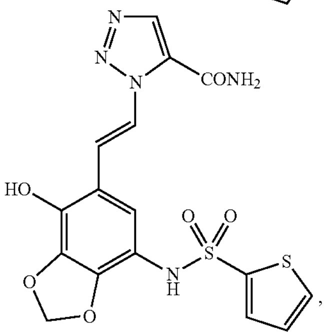

-continued
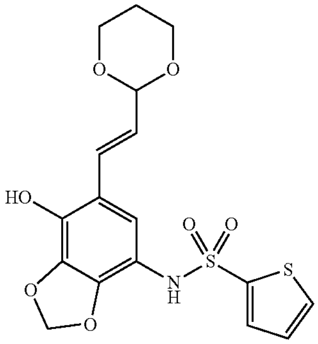
,
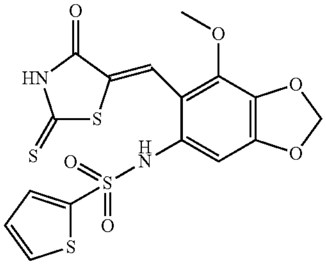
,
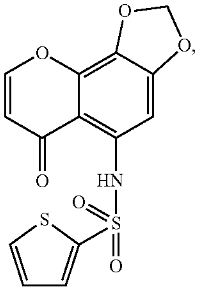
,
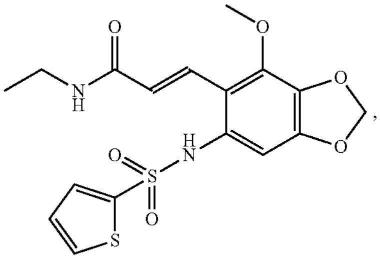
,
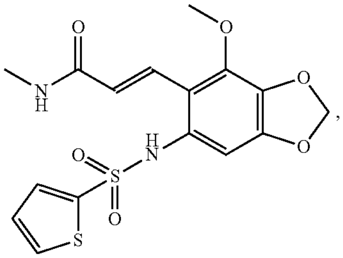
,
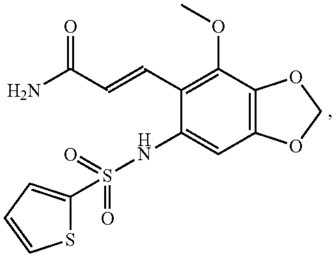
,
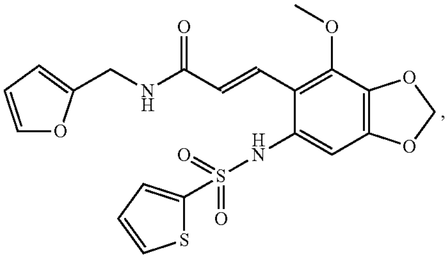
,
-continued
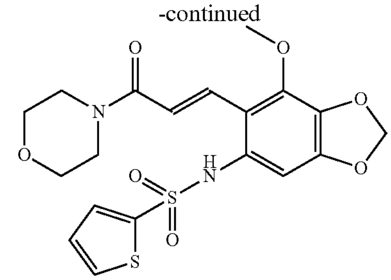
,
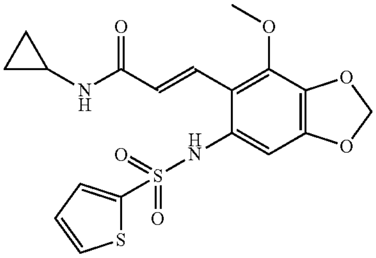
,
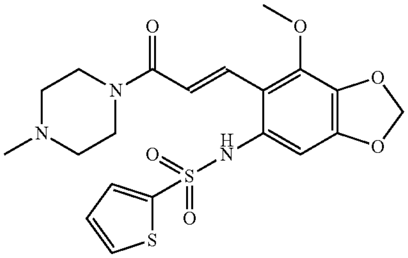
,
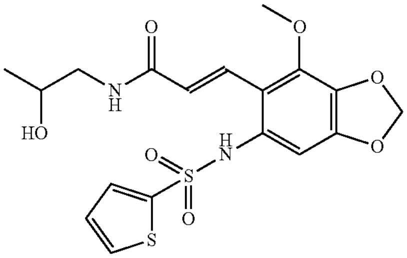
,
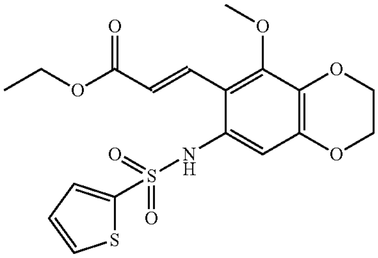
,
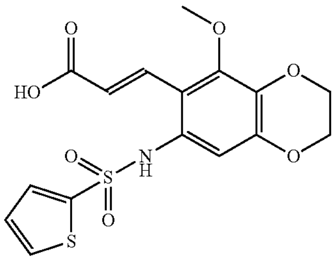
, -continued
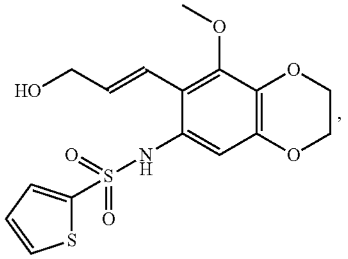
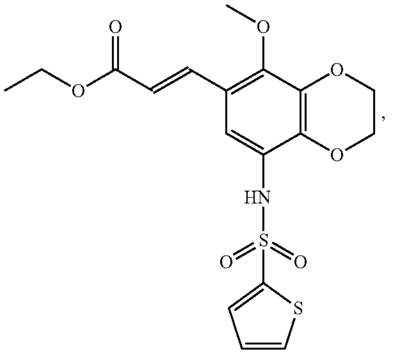
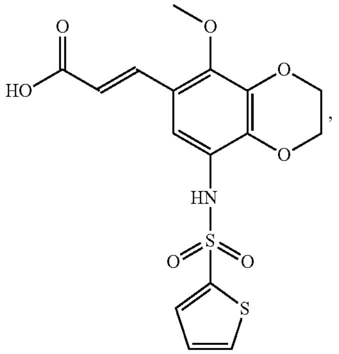
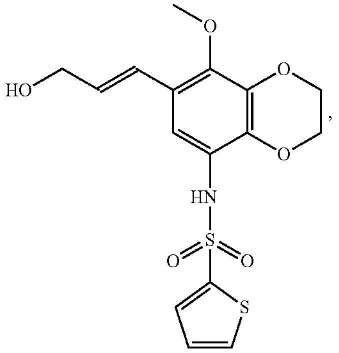
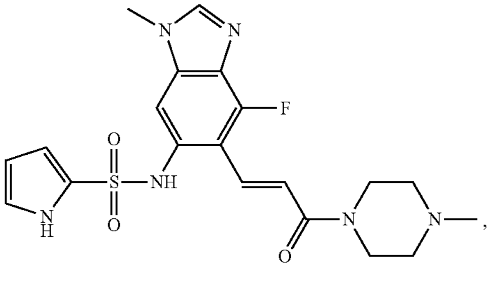
-continued
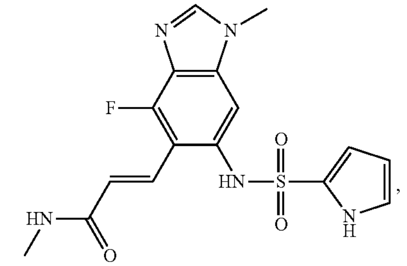
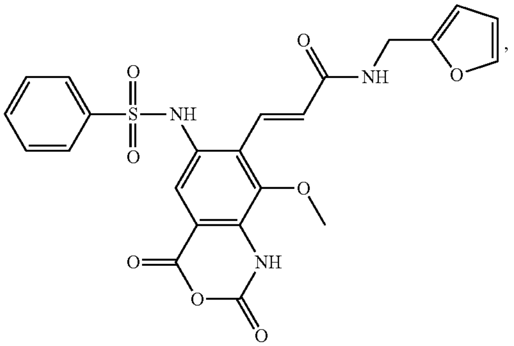
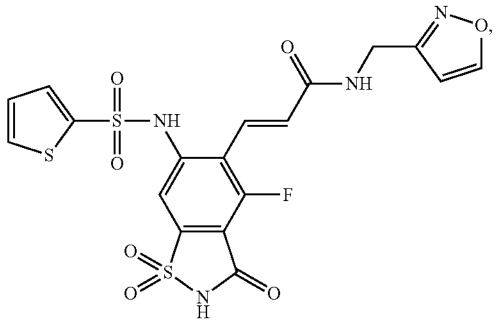
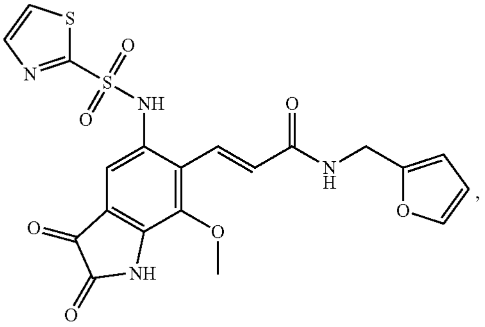
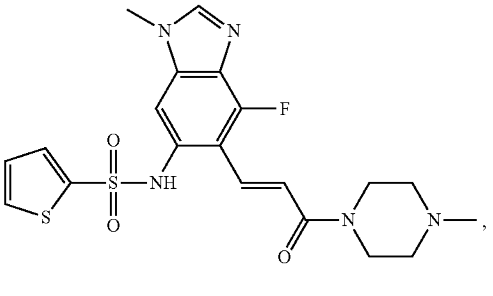

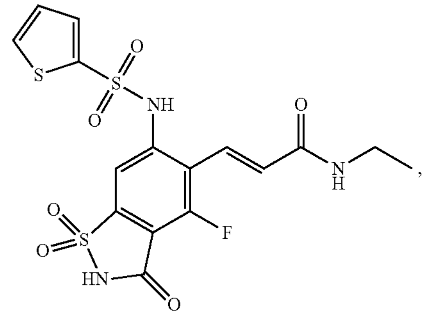
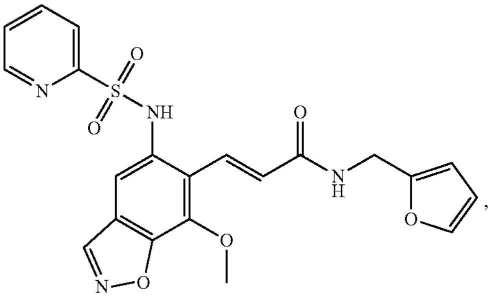
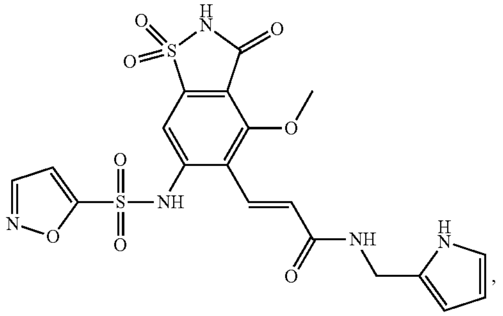
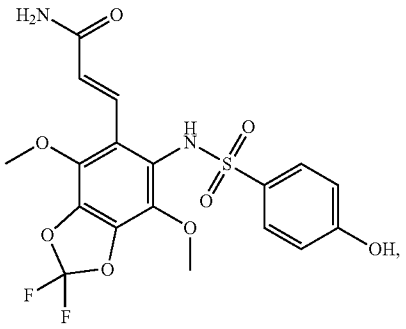
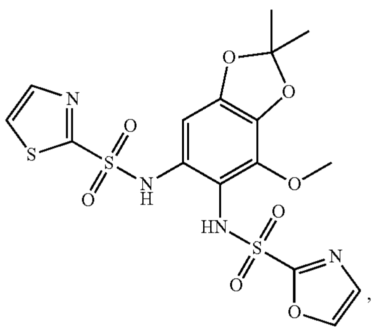
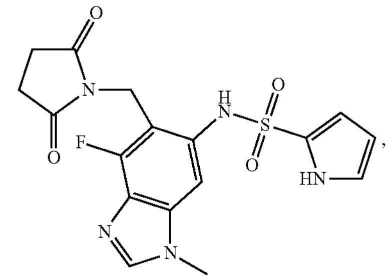
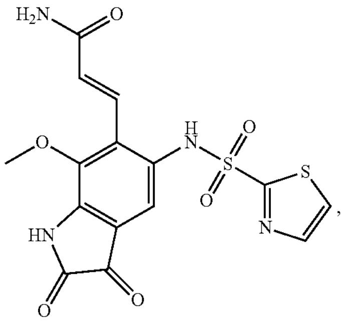
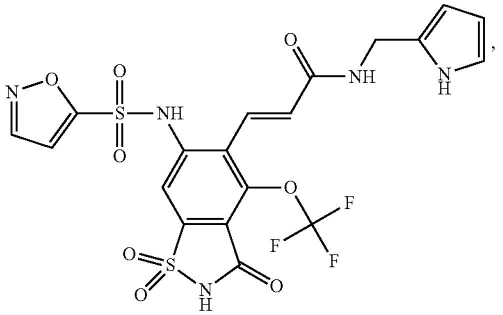
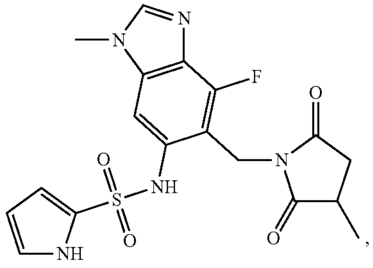
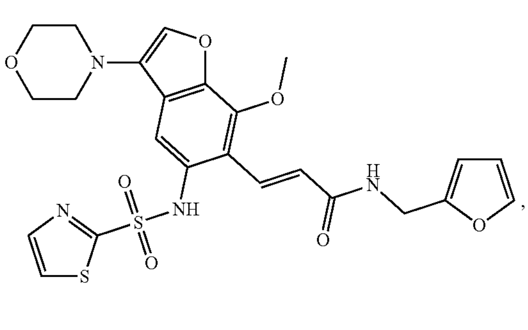

-continued
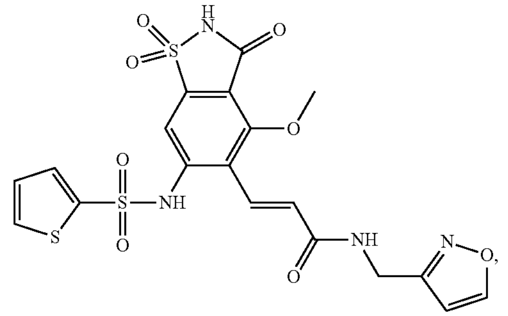
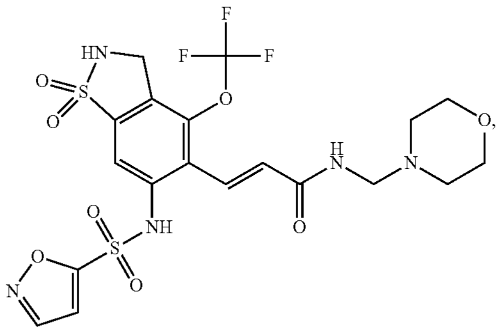
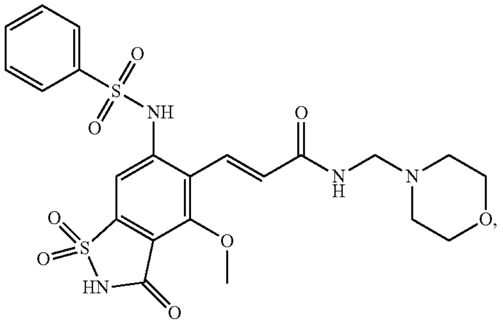
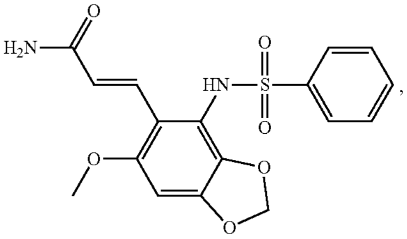
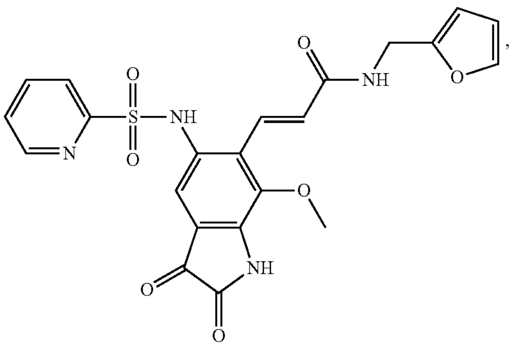
-continued
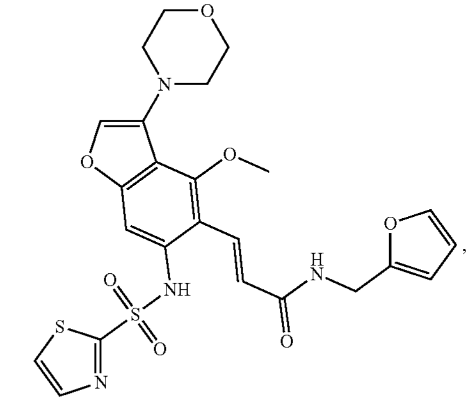
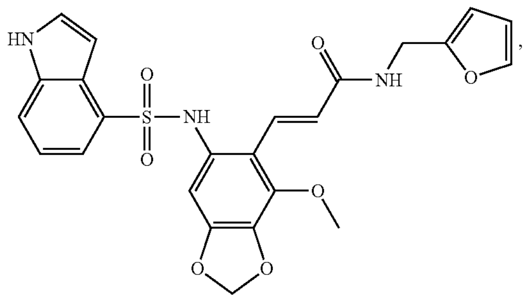
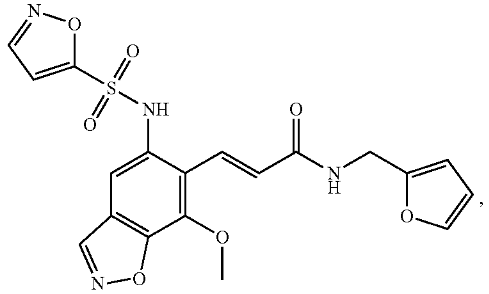
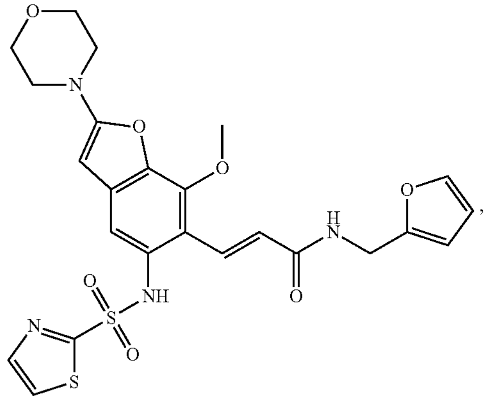
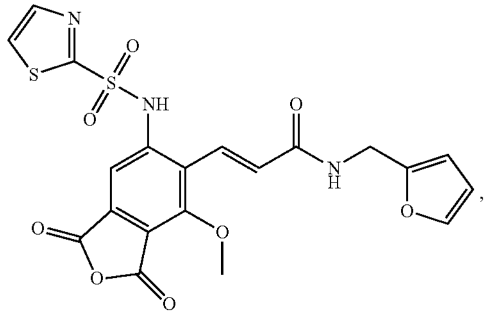

-continued
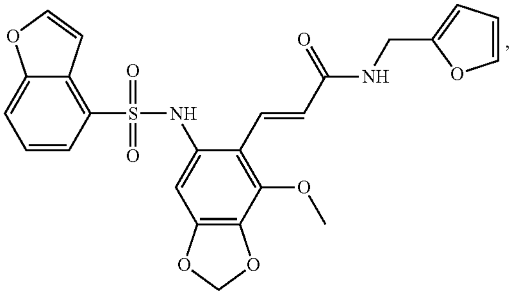
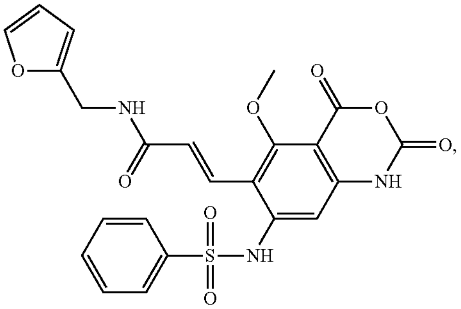
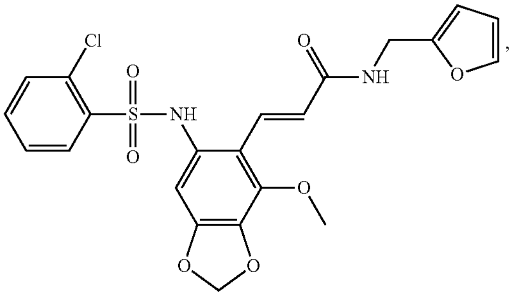
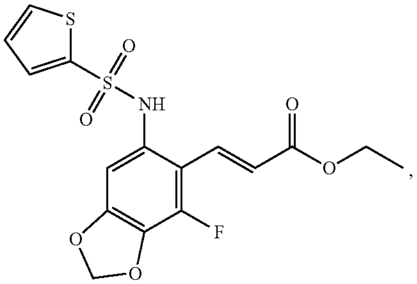
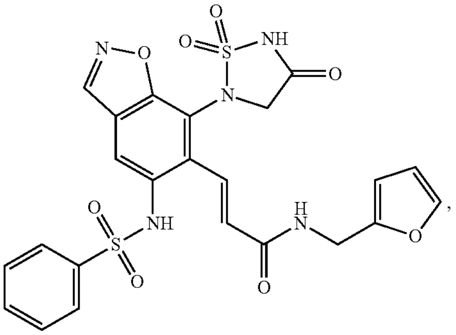
-continued
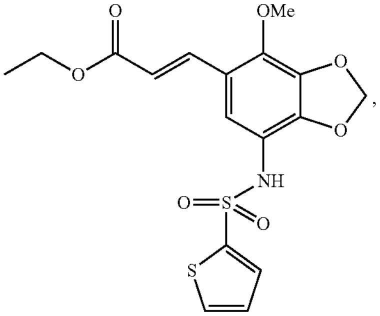
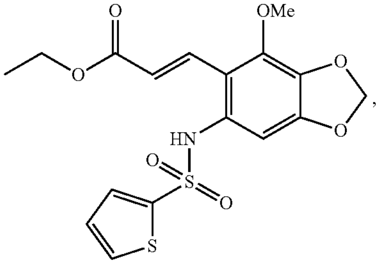
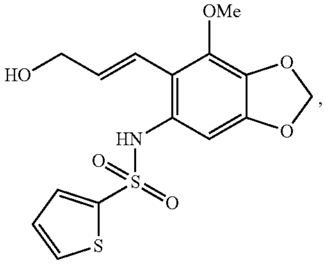
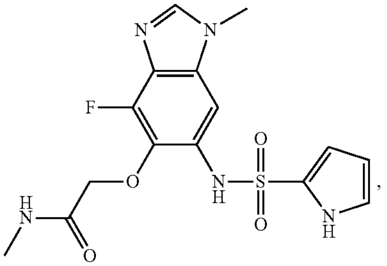
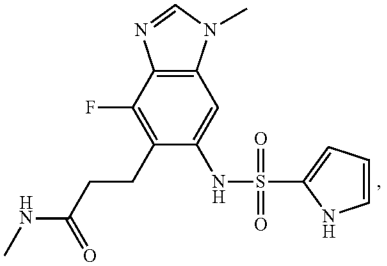
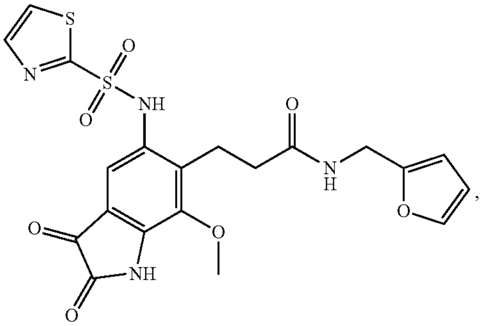

-continued
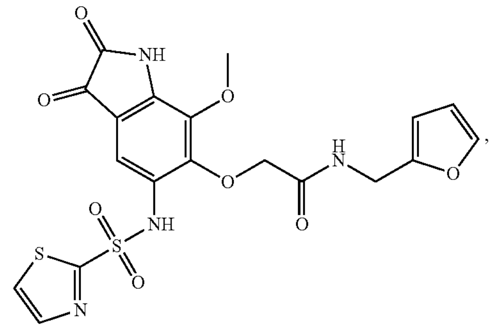
,
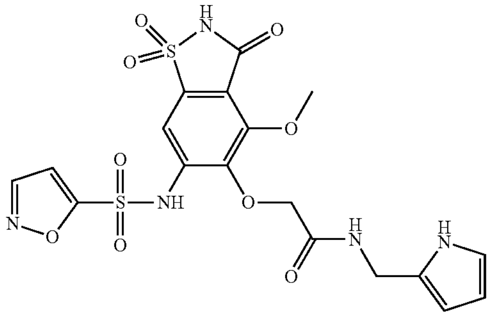
,
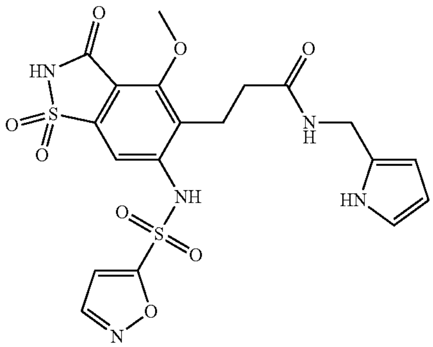
,
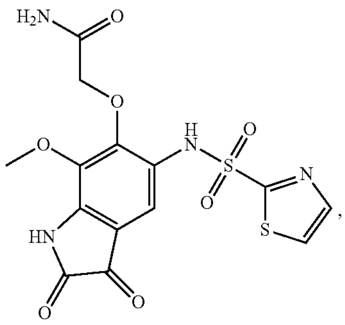
,
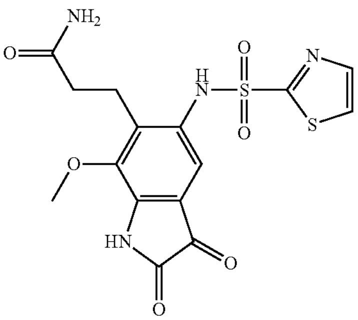
,
-continued
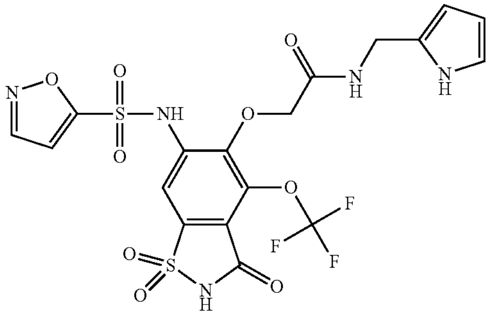
,
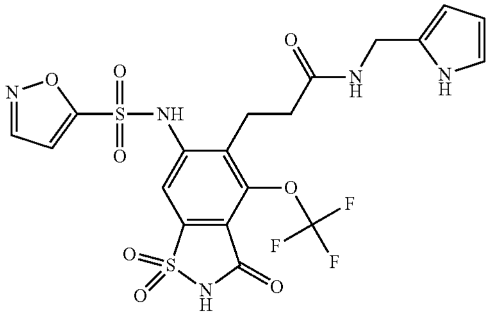
,
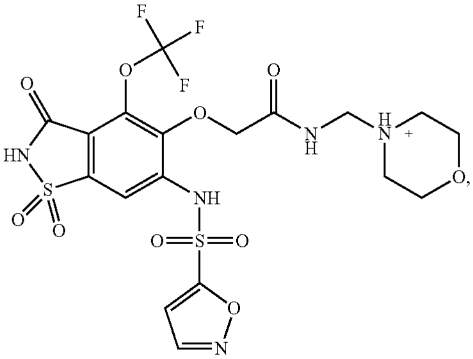
,
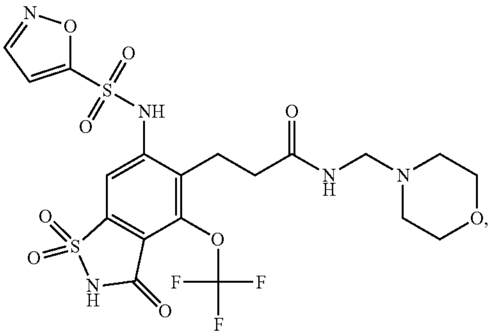
,
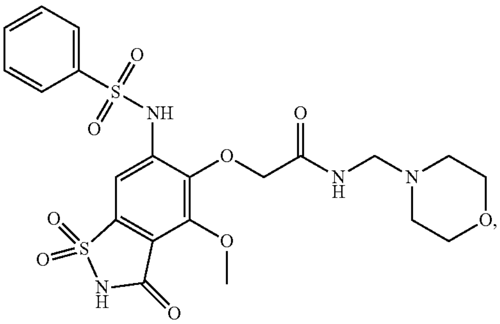
, -continued
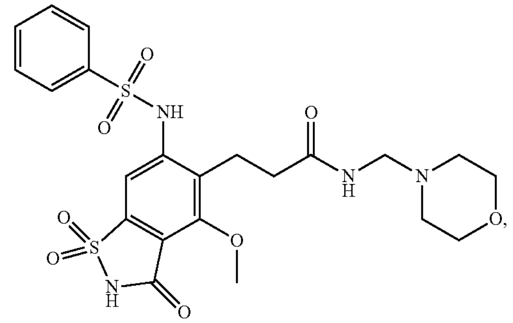
,
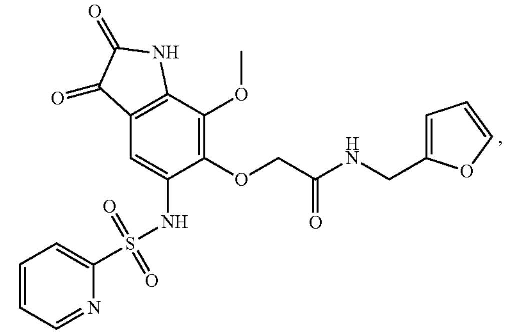
,
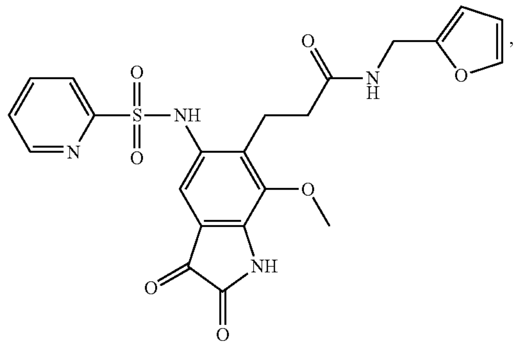
,
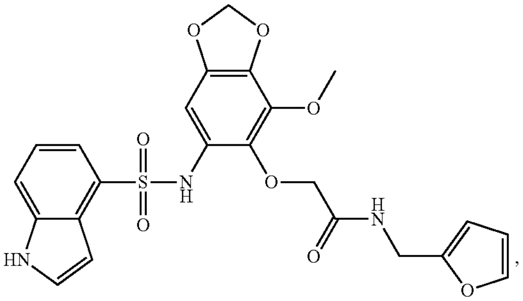
,
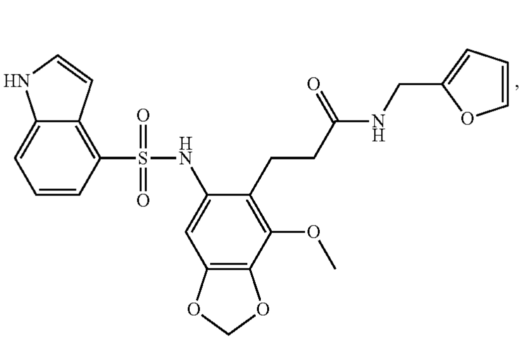
,
-continued
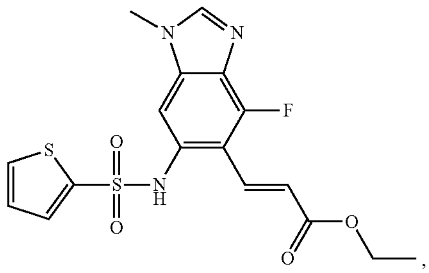
,
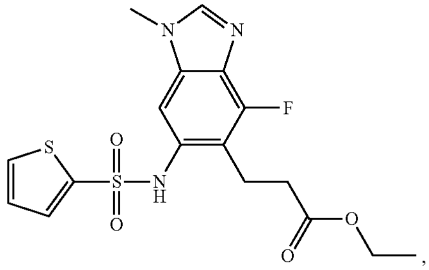
,
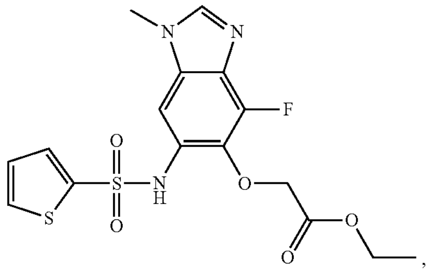
,
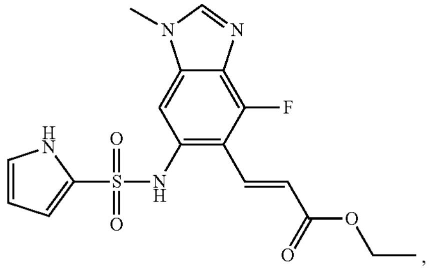
,
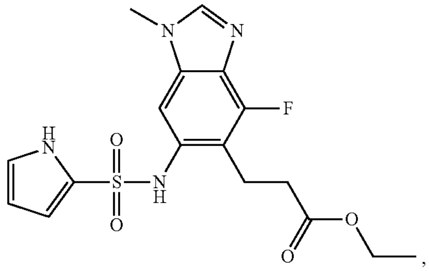
,
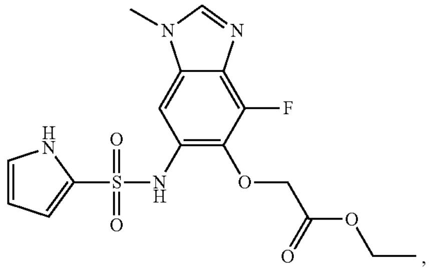
, -continued
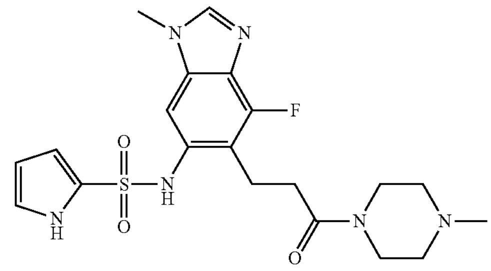
,
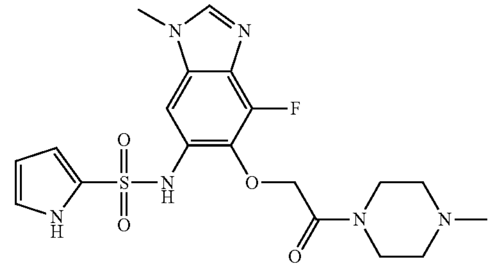
,
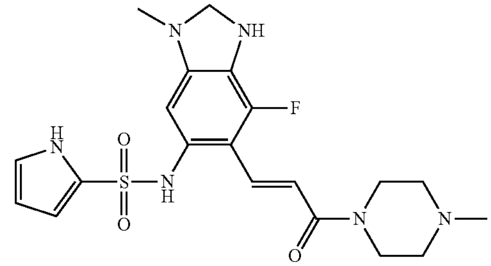
,
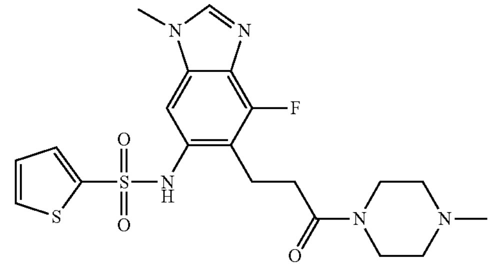
,
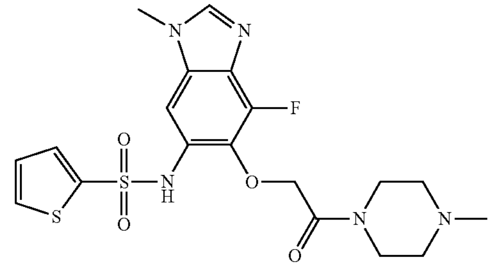
,
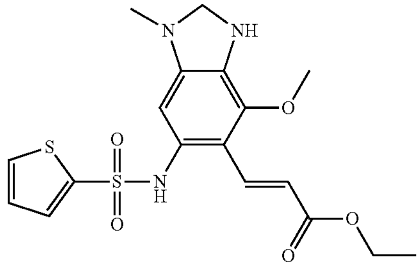
,
-continued
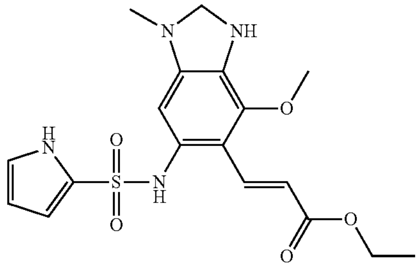
,
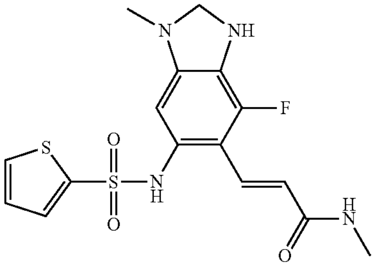
,
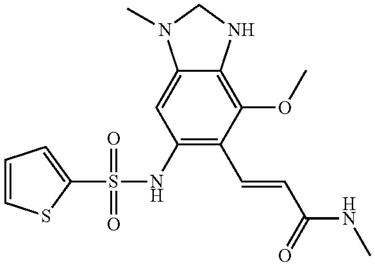
,
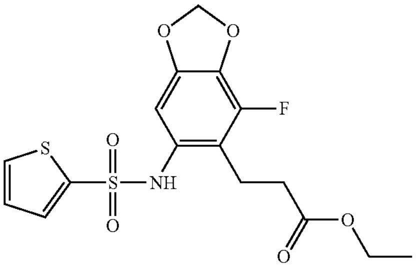
,
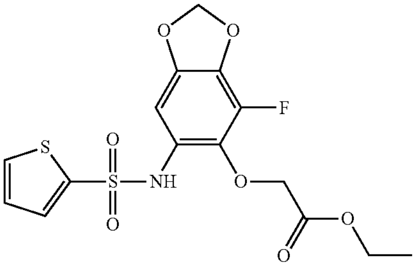
,
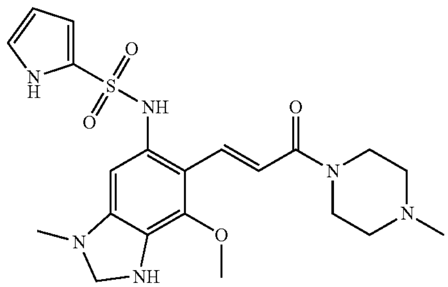
, -continued

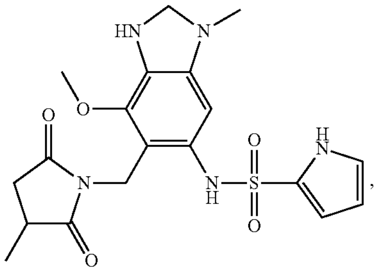

, and

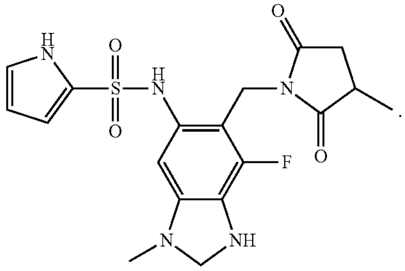

.

Some embodiments provide pharmaceutical compositions, comprising a compound according to an embodiment described herein and a pharmaceutically acceptable carrier or diluent. In embodiments, the compound may be present in a therapeutically effective amount.

Some embodiments provide a method of treating cancer comprising administering a therapeutically effective amount of a compound according to an embodiment described herein.

Further embodiments provide methods, wherein the cancer is selected from adrenocortical carcinoma, anal cancer, bladder cancer, brain tumor, breast cancer, carcinoid tumor, gastrointestinal carcinoma of unknown primary, cervical cancer, colon cancer, endometrial cancer, esophageal cancer, extrahepatic bile duct cancer, Ewing's family of tumors (PNET), extracranial germ cell tumor, eye cancer, intraocular melanoma, gallbladder cancer, gastric cancer (stomach), germ cell tumor, extragonadal, gestational trophoblastic tumor, head and neck cancer, hypopharyngeal cancer, islet cell carcinoma, kidney cancer, laryngeal cancer, leukemia, acute lymphoblastic adult leukemia, acute lymphoblastic, childhood leukemia, lip and oral cavity cancer, liver cancer, lung cancer, lymphoma, aids-related lymphoma, central nervous system (primary) lymphoma, cutaneous T-cell, lymphoma, Hodgkin's disease adult lymphoma, Hodgkin's disease childhood lymphoma, non-Hodgkin's disease, adult lymphoma, non-Hodgkin's disease childhood lymphoma, malignant mesothelioma, melanoma, merkel cell carcinoma, metastatic squamous neck cancer with occult primary, multiple myeloma and other plasma cell neoplasms, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell tumor, pancreatic cancer, exocrine, pancreatic cancer, islet cell carcinoma, paranasal sinus and nasal cavity cancer, parathyroid cancer, penile cancer, pituitary cancer, plasma cell neoplasm, prostate cancer, rhabdomyosarcoma, childhood, rectal cancer, renal cell cancer, renal pelvis and ureter, transitional cell, salivary gland cancer, sezary syndrome, skin cancer, skin cancer, cutaneous T-cell lymphoma, skin cancer, Kaposi's sarcoma, skin cancer, melanoma, small intestine cancer, soft tissue sarcoma, adult, soft tissue sarcoma, child, stomach cancer, testicular cancer, thymoma, malignant, thyroid cancer, urethral cancer, uterine cancer, sarcoma, unusual cancer of childhood, vaginal cancer, vulvar cancer, Wilms' Tumor, and combinations thereof.

Some embodiments provide a method of inhibiting CNKSR1 comprising administering a therapeutically effective amount of a compound according to an embodiment described herein.

For example, some embodiments are directed to a pharmaceutical composition comprising a compound, as defined above, and a pharmaceutically acceptable carrier or diluent, or a therapeutically effective amount of a pharmaceutical composition comprising a compound as defined above.

The compounds described herein may be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the compounds of the present invention (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

Pharmaceutical formulations containing the compounds of the present invention and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics,* 6th Edition, MacMillan Publishing Co., New York (1980) can be consulted.

The compounds of the present invention can be formulated for parenteral administration by injection, e.g., by bolus injection or continuous infusion. The compounds can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present invention can also be formulated in rectal compositions such as suppositories or retention enemas, e.g., containing conventional suppository bases such as cocoa butter or other glycerides.

In addition to the formulations described herein, the compounds of the present invention may also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds of the present invention, for example, can be applied to a plaster, or can be applied by transdermal, therapeutic systems that are consequently supplied to the organism.

Pharmaceutical compositions of the compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The compounds of the present invention can also be administered in combination with other active ingredients, such as, for example, adjuvants, protease inhibitors, or other compatible drugs or compounds where such combination is seen to be desirable or advantageous in achieving the desired effects of the methods described herein.

In some embodiments, the disintegrant component comprises one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

In some embodiments, the optional lubricant component, when present, comprises one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, or sodium chloride.

RAS proteins may self-assemble together with other membrane-associated proteins, effectors and scaffolding proteins into plasma membrane tethered microdomains known as nanoclusters. The nanoclusters may be small (about 6-20 nm diameter), short lived (t1/2 less than about 0.4 s) signaling platforms, and may contain 6 or more proteins. Nanoclusters can differ depending upon the charge and covalent lipid modification of the C-terminal hypervariable (hv) region of the individual RAS isoforms. Downstream signaling effectors may be activated by about 40% of the RAS which is associated in nanoclusters, while the remaining RAS is randomly arrayed over the cell surface.

RAS proteins undergo several steps of translational modification which can determine their membrane localization (FIG. 1). RAS may share a C-terminal CAAX motif that can undergo cysteine residue preneylation (C15 farnesylation or C20 geranylgeranylation) followed by removal of the AAX residues by endoplasmic reticulum (ER) Rcel (RAS and a-factor converting enzyme-1) and carboxylation by Icmt (isoprenylcysteine carboxyl methyltransferase). These CAAX modifications by themselves may not be sufficient for RAS plasma membrane association and a second signal may be required. HRAS, NRAS and KRAS4A can undergo C16 palmitoylation on cysteine residues in their hv regions catalyzed by ER PATs (protein acyltransferases). In KRAS4B, the second membrane localization signal can be provided by a lysine rich polybasic amino acid sequence in its hv region that can facilitate an interaction with the negatively charged head groups of and phosphatidylinositol (PI) on the inner surface of the plasma membrane. PIP3 can be clustered in lipid raft nanodomains together with high levels of PI3K protein, to give regions of high signaling activity. The binding of the CNKSR1 PH-domain to PIP3 could serve to position the KRAS nanocluster in close proximity to the PI3K signaling nanodomain leading to activation of PI3K, a downstream signaling effector for KRAS. Some forms of mut-KRAS can have a higher affinity for binding to PI3K than wt-KRAS, due to a mutation induced change in the structure of the KRAS switch 1 and 2 binding regions that form direct contact with the PI-3-K catalytic domain causing allosteric activation. This could explain the greater sensitivity of mut-KRAS to inhibition by siRNA knockdown of CNKSR1 or PH-domain inhibition, than wt-KRAS.

The PH-domain is an about 100 to about 120 amino acid three dimensional superfold found in over 500 human proteins. The core of each PH-domain consists of seven β-strands and a C-terminal α-helix. While PH-domains may show a highly conserved 3 dimensional organization, the sequence identities among different proteins are only about 7% to about 23%. This is important because with this sequence diversity, selective agents can be identified that will be specific for each protein. PH-domains can bind to phosphotyrosine and polyproline sequences, Gβγ subunits of heterotrimeric G proteins and phosphoinositides (PIs). While for the majority of PH-domain proteins PI binding is weak and non-specific, the PH-domains of many proteins that are components of signal transduction pathways regulating cancer cell growth and survival show high affinity for PIP3 and sometimes PIP2. CNKSR1 is one such protein that has high affinity binding for PIP3. In embodiments, the binding of a small molecule to a PH-domain may inhibit protein function.

In other embodiments, identifying small molecule PH-domain inhibitors using a computational platform may speed identification of potential inhibitors and the decrease the costs of optimizing a drug lead. In such embodiments, the in silico molecular docking of libraries of several million chemical structures using the known crystal or homology model structures of the PH-domain of the protein of interest may be used to identify inhibitors of CNKSR1. Surface plasmon resonance (SPR) spectroscopy can measure the extent of binding of the compounds to the PH-domain of the protein, and in vitro cellular assays can determine biological efficacy. Once active moieties are identified there may be recursive refinement of the model through repeated in silico docking and SPR spectroscopic measurements of binding until lead compounds are obtained. Such embodiments may be used to discover highly specific and potent PH-domain inhibitors of CNKSR1.

This role of CNKSR1 as a molecular target for drug development is shown in FIG. 2A where transfection with siRNA to CNKSR1 (siCNKSR1) may inhibit growth of mut-KRAS MiaPaCa-2 pancreatic cells but not the growth of MiaPaCa-2 cells, where an allele of mut-KRAS has been disrupted by homologous recombination. siCNKSR1 may also inhibit growth of mut-KRAS HCT116 colon cancer cells but not the growth of HKE2 HCT116 cells, where mut-KRAS has been disrupted by homologous recombination. Table 1 shows that the selective inhibition of mut-KRAS cell growth can be validated with a second set of 4 individual siCNKSR1s from a second manufacturer.

TABLE 1

Validated hits with individual siRNAs in mut-KRAS isogenic lines

| | | MiaPaCa-2 Pancreatic | | HCT-116 Colon | |
|---|---|---|---|---|---|
| Gene Symbol | Name | % viability mut-RAS/ wt-KRAS | siRNAs* positive | % viability mut-RAS/ wt-KRAS | siRNAs* positive |
| CNKSR1 | connector enhancer of kinase suppressor of Ras 1 | 43.4 | 3/4 | 52.6 | 3/4 |

*second manufacturers individual siRNAs

The effect of siCNKSR1 is further shown in FIG. 2B where transfection with siCNKSR1 can inhibit the growth of a panel of 10 mut-KRAS non-small cell lung cancer (NSCLC) cell lines but not of 4 NSCLC cell lines with wt-KRAS.

In order to demonstrate whether the pleckstrin homology (PH) domain of CNKSR1 plays a role in facilitating the effect of CNKSR1 on mut-KRAS activity the PH-domain was overexpressed in H1373 mut-KRAS NSCLC cells and it was found that the domain acted as a dominant negative and inhibited cell growth. Without wishing to be bound, it is suggested that the PH-domain fragment competes with the full length CNKSR1 in the cell (FIG. 2C).

In embodiments, a homology model for the PH-domain of CNSKR1 based on known PH-domain crystal structures can be developed. The docking program PHuDock® can be used to identify potential inhibitors of CNKSR1. Using an in silico library of over 3 million compounds, compounds have been identified as potential inhibitors of CNKSR1 and, thus, of mut-KRAS cell lines. The binding of the compounds to the expressed PH-domain of CNKSR1 (KDobs) can be measured by surface plasmon resonance (SPR) spectroscopy.

In embodiments, the binding of identified compounds to the crystal structures of other PH-domain signaling proteins, AKT, PDPK1, Btk, and PLEKHA7 can be predicted. In such embodiments, the Kds exceed about 100 μM. In other embodiments, SPR can measure the binding of identified compounds to the expressed PH-domains of AKT, PDPK1 and PLEKHA7.

In embodiments, a homology model can predict small molecules that bind to the PH-domain of CNKSR1, and identify compounds that exhibit selective inhibition of mut-KRAS cell proliferation. CNKSR1 inhibition of K-RAS signaling can be measured by Western blotting of the down stream target phospho-c-RAF(Ser338) which is specifically phosphorylated by KRAS.

In embodiments, identified compounds may be nontoxic at about 200 mg/day for about 20 days with no weight loss and no observable toxic effects for the animal, and may have antitumor activity Experimental Description Screening of Compounds Against Isogenic Mutant KRAS Lines (FIG. 2).

The isogenic KRAS lines harboring G12D, G12C, and G12V were obtained from Horizon Discovery labs on a one year lease. These cells were cultured in McCoys media with 10% FBS to 80% confluency. Cells were then released from flasks via trypsinization and plated into 96-well plates at an initial density range of 2000 cells per well. Cells were allowed 24 hours to attach, and then the agents were added to the culture media at a range of concentrations from 0-100 μM. Cells were incubated for 72 hours with the drugs, and then viability was assessed using an MTS viability assay. Cells were exposed to MTS reagent (Promega) dissolved in PBS (Hyclone) at a concentration of 200 μL reagent/mL media for 2 hours. Absorbance was then read at 490 nm, and viability was expressed as a percentage normalized between the negative control (no cells plated) and the condition of cells with no drug added (100% viability) normalized as the upper limit of viability.

Screening of Compounds Against NSCLC Cell Line Panel (FIGS. 2 and 3B).

A panel of 30 cell lines and an extensive characterization were obtained from Dr. John Minna (UTSW). All cell lines were cultured in RPMI 1640 with 10% FBS. Cells were treated with concentrations of agents at concentrations 0.01 to 50 μM and evaluated as described above. $IC_{50}$'s were determined using Excelfit.

siRNA Screening

MiaPaCa-2 and M27 were confirmed *mycoplasma* and maintained in DMEM with 10% FBS. Optimization was carried out using in house optimization methods in house. A parallel screen was then carried out with a genome wide siRNA library (Dharmacon).

Individual siRNA and Plasmid Transfection.

For transfection in a six well plate, cells were plated at 100,000 cells per well in 2 mls media and allowed to attach overnight. Per well 5 μl of Dharmafect 2 (Dharmacon) was added to 200 μl OptiMEM (Gibco) and 4 μl of the siCNKSR1 smartpool Dharmacon (M-012217-01-0020) or individual siCNKSR1 siRNAs (Qiagen SIO2665411) was added to 200 μL to OptiMEM in parallel and allowed to sit for 5 minutes. These tubes were mixed and incubated at room temperature for 20 minutes. 1.6 of the appropriate media was then added to this mixture. and then media in the wells removed. This mixture was then added to the cells in a dropwise fashion and the cells were incubated for 48-72 hours. For the GFP control and CNK1 PH-domain plasmids 175,000 cells per well plated in a 6 well plate. Per well 2.5 μl of lipofectamine 2000 (Gibco) and 125 μl of OptiMEM were combined and 2.5 m of the appropriate plasmid and 125 μl of OptiMEM were combined in separate tubes and allowed to incubate at room temperature for 5 minutes. These two tubes were then combined and allowed to incubate for 20 minutes. 200 μl of this mixture was then added to 1 ml of fresh media already in the appropriate well and allowed to incubate for 5 hours. The transfection efficiency was determined through the expression of GFP after 24 hours and the cells were counted with a hemocytometer after 72 hours to determine viability.

Spheroid Formation (FIG. 4)

The plates were optimized for the best cell density and found to be 20,000 cells per mL. The lid was removed from a 96-well Greiner plate and turned upside down. 20 μL of the 20,000 cells per mL suspension was then added directly into the middle of the circles found on the lid of the 96-well plate forming a small drop. 100 μL of media was added into the corresponding wells, used to maintain the temperature of the drops, and the lid was flipped back over carefully placing it back onto the plate without disturbing the drop. The plate was then placed into the incubator for 3 days to allow the cells to migrate to the bottom of the drop due to gravity. After 3 days, 400 μL of media was added to the corresponding wells a SCIVAX 96-well plate. The lid from the Greiner 96-well plate was removed and placed onto the SCIVAX plate allowing the drop to come in contact with the media and placed back into the incubator. After one hour, 200 μL of media was removed from the corresponding wells carefully without disturbing the spheroid and imaged.

Confocal Imaging (FIG. 5)

HEK293T cells were co-transfected with CNK and either wild type or G12D mutant KRAS. Twenty-four hours post-transfection, cells were seeded on glass coverslips and allowed to grow a further 24 h and then serum deprived overnight. Cells were fixed with 4% (w/v) paraformaldehyde pH 8.0 for 20 min at room temperature. Following 6-7 washes with PBS (pH 8.0) the coverslip was mounted onto a slide with mounting medium (0.1% p-phenylenediamine/75% glycerol in PBS at pH 7.5-8.0). Confocal laser scanning microscopy was performed with a Leica SP5 confocal microscope system with 63× oil-immersion objective (numerical aperture NA=1.4), a line scan speed of 600 Hz, with image size of 1024×1024 pixels. GFP was excited with an argon-visible light laser tuned to 488 nm, mRFP were excited with a krypton laser tuned to 543 nm. GFP and RFP fluorescence emissions were collected using a photomultiplier tube via 514/10 nm and 595/10 nm band selections respectively.

Fluorescence Lifetime Imaging Microscopy (FLIM)

FLIM experiments were carried out using a Leica TCP SP5 inverted advanced confocal microscope system with internal photomultiplier tube (PMT) detector for TCSPC (time-correlated single-photon counting). The sample was excited with a tunable femtosecond (fs) titanium-sapphire laser with repetition rate of 80 MHz and pulse width less then 80 fs (Spectral Physics, Mai Tai BB). The wavelength used for two-photon excitation was 930 nm and the fluorescence was detected through a 525±25 nm interference filter. Images were obtained with oil-immersion objective (numerical aperture NA=1.4), a line scan speed of 400 Hz, with image size of 512×512 pixels. For FLIM analysis the pixels were reduced to 256×256. FLIM data was collected using Becker & Hickl SPC830 data and image acquisition card for TCSPC. The fluorescence decays were fitted with a single exponential decay model using Becker and Hickl's SPCImage software and the GFP fluorescence lifetimes were displayed in a false colour map.

Surface Plasmon Resonance Spectroscopy Binding Assays (Binding Scores for all Agents)

All interaction analyses were done with a Biacore T200 Control Software v3.2, and BIAevaluation v2.0 analysis software (Biacore). The PH-domain His-fusion proteins (CNK1 and AKT1) were expressed and immobilized on a NTA chip to a level of 10,000 response units or less. Small molecule analytes at concentrations ranging from 50 μM to 0.010 μM were injected at a high flow rate (30 μL/min). DMSO concentrations in all samples and running buffer were 1-5% (v/v) (30 μL/min). DMSO concentrations in all samples and running buffer were 1-5% (v/v).

The plekstrin homology domain of CNK and PLEKHA7 expressed with GST at the N-terminus, CNK(PH)-GST were immobilized on a CM5 chip. Analysis of potential small molecule drug binding was done using a Biacore T200. Immobilization of antibody was run at 37° C. and a flow rate of 5 μL/min. A freshly prepared mixture of aqueous 0.4M 1-ethyl-3-(3-dimethylaminopropyl)carbodiimide hydrochloride (EDC) and aqueous 0.1M N-hydroxysuccinamide (NETS), (0.2M/0.05M EDC/NHS solution) is injected for 480 seconds over a conditioned (Tanious, et al doi:10.1016/50091-679X(07)84003-9) CM5 chip flow cell. The activated surface is then injected at 37° C., flow rate of 5 μL/min for 480 sec with 30 μg/mL anti-GST antibody, freshly suspended in pH 5.0 10 mM acetate buffer. Expected capture is 12000-20000 response units (RU). The remaining active surface is deactivated with 480 sec injections of 0.1M ethylenediamine in borate buffer (GE Healthcare) and then 1M ethanolamine pH 8.5 to provide 10000-18000 RU of covalently linked antibody on the flow cell. An upstream reference flow cell (Fc1) and a downstream working flow cell (Fc2) are prepared in this manner. A TBS-P20-DMSO solution running buffer (TRIS buffered saline solution with 0.05% (w/v) Polysorbate 20 and 1% (v/v) DMSO) was used for capture of fusion protein and all drug binding studies. CNK(PH)-GST or PLEKHA7(PH)-GST in running buffer (20 μg/mL) was captured onto Fc2 at 37° C. with a flow rate of 5 μL/min for 300 sec. rGST in running buffer (5 μg/mL) was captured onto Fc1 at 37° C., flow rate of 5 μL/min for 180 sec. All drug stock solutions were prepared in anhydrous DMSO to a concentration of 10 mM. Dilutions by into a DMSO-free running buffer provided a 100 μM drug solution in running buffer suitable for dilutions as needed for steady-state affinity studies (range 1 to 80 μM). At a flow rate of 10 μL/min, each solution was injected for 6 minutes. Binding responses were determined 4 seconds prior to the conclusion of the injection. Surface regeneration was achieved by allowing for dissociation in running buffer for 10 minutes after injection.

Immunoblots and Immunoprecipitations

Cells were washed twice with ice-cold PBS and lysis buffer containing 50 mmol/L HEPES (pH 7.5), 50 mmol/L NaCl, 0.2 mmol/L NaF, 0.2 mmol/L sodium orthovanadate, 1 mmol/L phenylmethylsulfonyl fluoride, 20 μg/mL aprotinin, 20 μg/mL leupeptin, 1% NP40, and 0.25% sodium deoxycholate. Protein concentration was determined by bicinchoninic acid assay (Pierce Biotechnology) and 50 μg of cell lysate protein were boiled for 5 min with denaturing buffer containing 0.25 mol/L Tris (pH 6.8), 35% glycerol, 8% SDS, and 10% 2-mercaptoethanol, loaded on a 10% acrylamide/bisacrylamide gel, and separated by electrophoresis at 150 V for 40 min. Proteins were electrophoretically transferred to a nitrocellulose membrane; preincubated with a blocking buffer of 137 mmol/L NaCl, 2.7 mmol/L KCl, 897 mmol/L CaCl2, 491 mmol/L MgCl2, 3.4 mmol/L Na2HPO4, 593 mmol/L KH2PO4, and 5% bovine serum albumin; and incubated overnight with anti-phosphorylated Thr308-Akt, Ser473-Akt, anti-CRaf Ser 338 Mapk Thr202/Tyr204, p70 S6K Thr389 or anti-Akt. (Cell Signaling 1:1000), anti-CNKSR1 (Signal Transduction labs) anti-lamin A/C and anti-β-actin (Santa Cruz Biotechnology 1:2000Donkey anti-rabbit IgG peroxidase-coupled secondary antibody (GE Healthcare) was used for detection). For measurement of active RalA and RalB, Ral and RalB activation kits were used (Biorad). Band density was measured using the Renaissance chemiluminescence system on Kodak X-Omat Blue ML films (Eastman Kodak).

A commercially available docking package GLIDE was chosen as the docking algorithm used to select and optimize compounds, providing a GlideScore as a rough estimate of binding affinity that was used to rank and select the best compounds. Additionally, ligand-based approaches provided an alternative to structure based drug discovery. Ligand-based virtual screening methodologies can take into account shape and electrostatics and the pharmacophoric features (acceptor, donor, hydrophobic, aromatic, etc.) of its functional groups. Inositol tetraphosphate (IP4) binding to the PH-domain of CNKSR1 provided a good starting point for shape screening. Both structure-based and ligand-based approaches were used to find novel compounds and to refine and improve lead compounds (Tables 2, 3 and 4). SPR interaction analyses for the compounds were performed with a Biacore T200, using BiacoreT200 Control Software v3.2 and BIAevaluation v2.0analysis software (Biacore). Data fitting plotting RU response versus concentration, was done using an unconstrained model, Req=Rmax/(1+(KD/c)) When conc=KD, then Req=0.5*Rmax.

Synthetic Scheme I
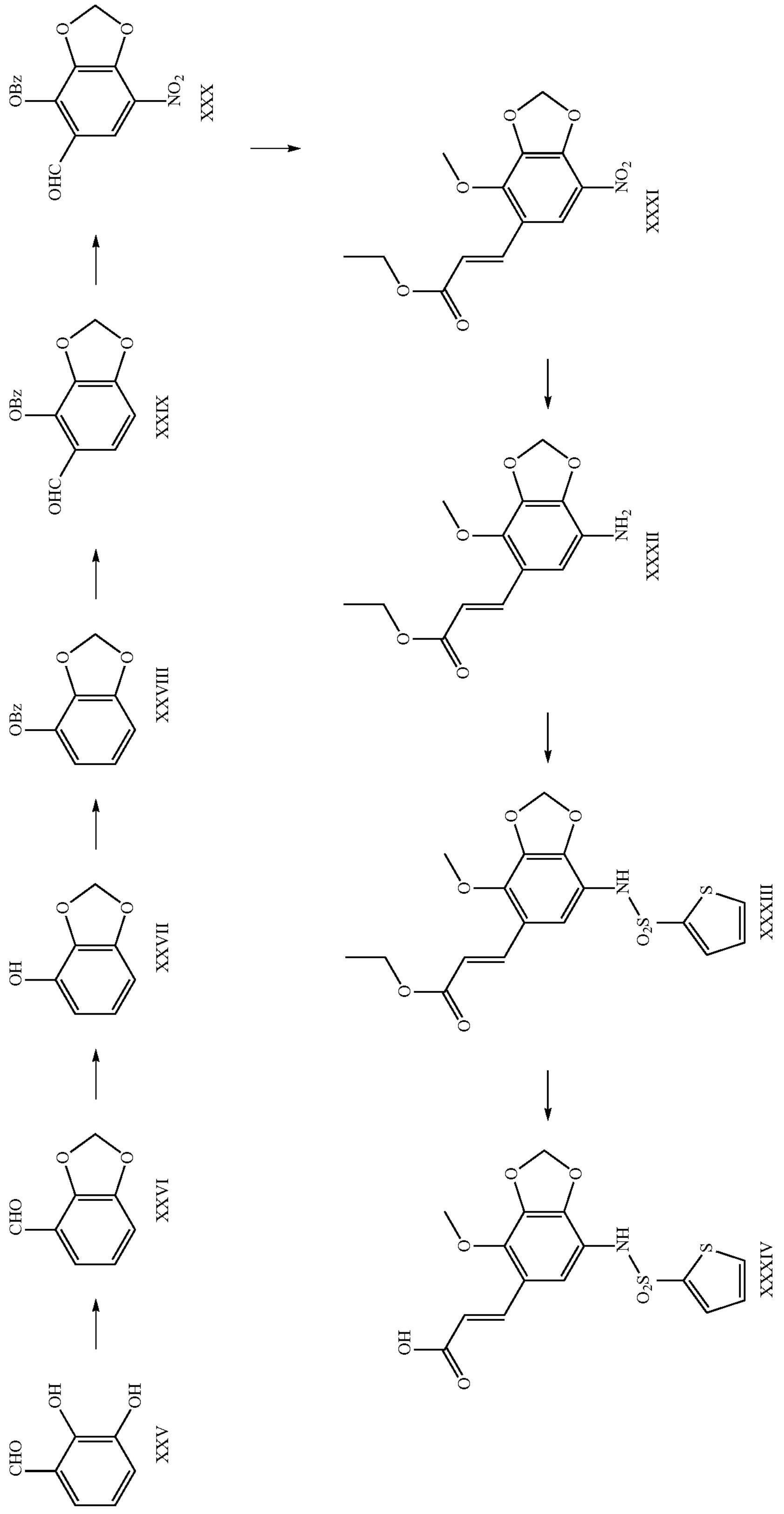
XXV XXVI XXVII XXVIII XXIX XXX XXXI XXXII XXXIII XXXIV Compounds in accordance with embodiments may be produced as shown in Synthetic Scheme I. 2,3-Dihydroxybenzaldehyde XXV was ketalized with formaldehyde to give the aryl dioxole XXVI, and the aldehyde oxidized to give the phenol XXVII. Acylation of the benzyl protected phenol with a formate equivalent gave the benzaldehyde XXIX, which was nitrated to give the nitrobenzaldehyde XXX. The aldehyde was conjugated to give the unsaturated ester XXXI, and reduced to the anilino ester XXII. Sulfonylation gave the thioamide XXXIII (compound 85), which was saponified to the carboxylic acid XXXIV (compound 83). Similarly, analogs 80-90 may be prepared by a person of skill in the art of organic synthesis. A person of skill in the art of organic synthesis can readily prepare other claimed compounds by processes similar to those in Scheme I.

Compounds in accordance with embodiments may be produced as shown in Synthetic Scheme II. Benzo[d][1,3]dioxole-5-carbaldehyde XXXV was reacted with cyclohexyl amine to yield imine XXXVI that was oxidized and subsequently protected to yield benzaldehyde XXXVIII. Benzaldehyde XXXVIII was nitrated to yield nitrobenzaldehyde XXXIX. Nitrobenzaldehyde XXXIX was conjugated to give the unsaturated ester XL that was reduced to the aniline ester XLI. Sulfonylation gave the thioamide XLII, which was saponified to the carboxylic acid XLIII Carboxylic acid XLIII was converted into acid chloride XLIV that was converted into amide XLV (compounds 105 to 112).

Synthetic Scheme II

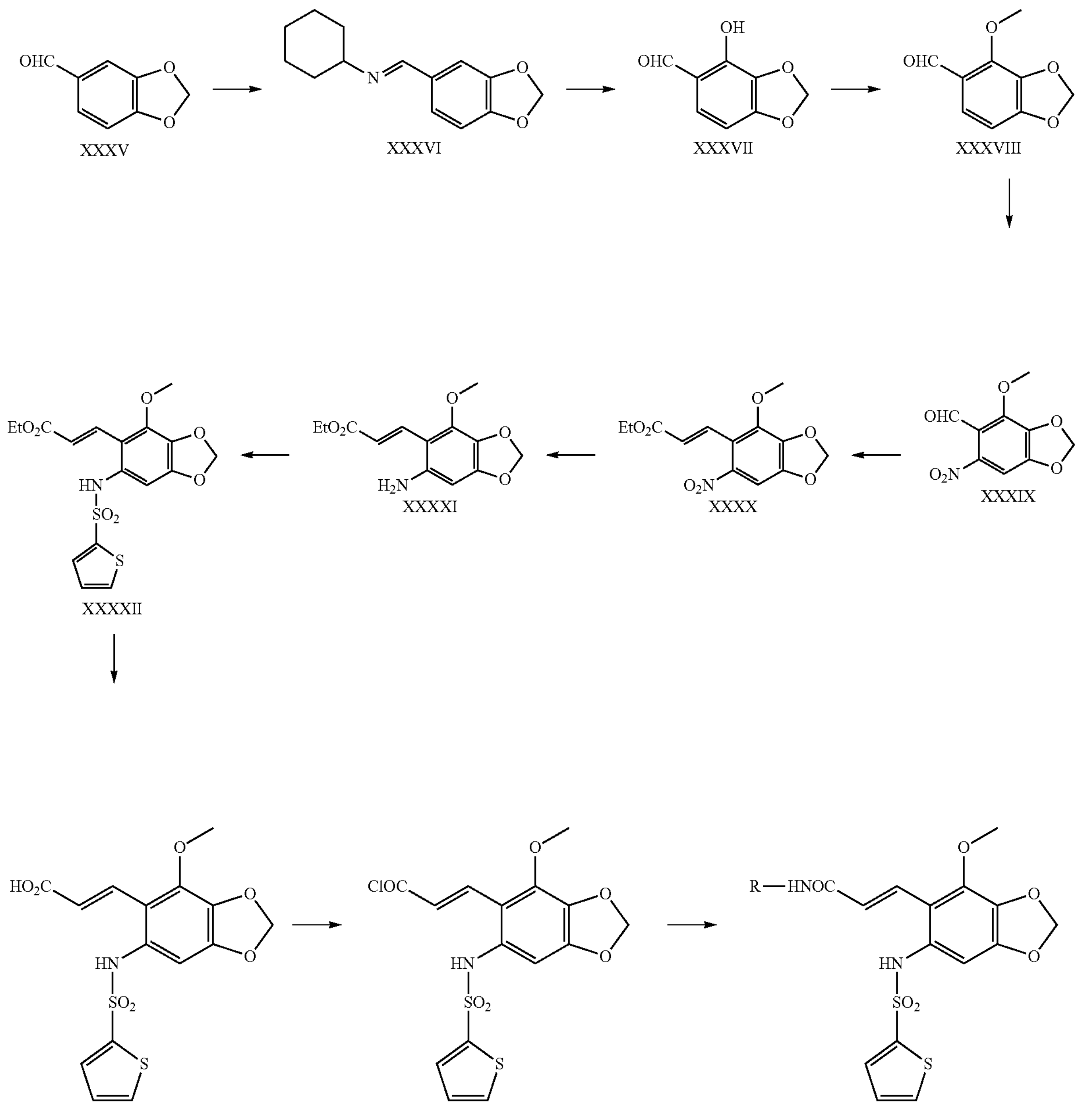

XXXV XXXVI XXXVII XXXVIII

XXXXII XXXXI XXXX XXXIX

XXXXIII XXXXIV XXXXV

TABLE 2

Analogs modeled from Second Series Hits

| Structure | CV No | Mol WT | CNK $K_D$ (μM) | PLEK $K_D$ (μM) | AKT $K_D$ (μM) | IUPAC Name |
|---|---|---|---|---|---|---|
| 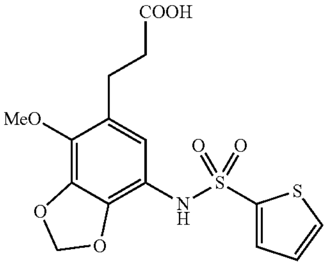 [SMILES: COc1c(CCC(=O)O)cc(NS(=O)(=O)c2cccs2)c2c1OCO2] | 83 | 385 | na | na | na | 3-(4-methoxy-7-(thiophene-2-sulfonamido)benzo[d][1,3]dioxol-5-yl)propanoic acid |
| 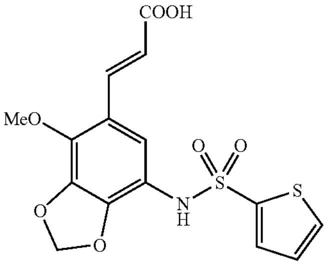 [SMILES: COc1c(/C=C/C(=O)O)cc(NS(=O)(=O)c2cccs2)c2c1OCO2] | 84 | 383 | ND | na | No binding | (E)-3-(4-methoxy-7-(thiophene-2-sulfonamido)benzo[d][1,3]dioxol-5-yl)acrylic acid |
| 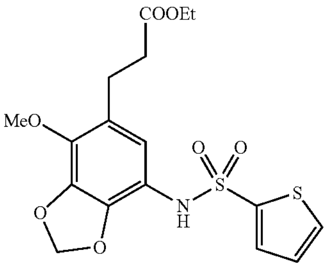 | 85 | 413 | >500 | na | >500 | ethyl 3-(4-methoxy-7-(thiophene-2-sulfonamido)benzo[d][1,3]dioxol-5-yl)propanoate |
| 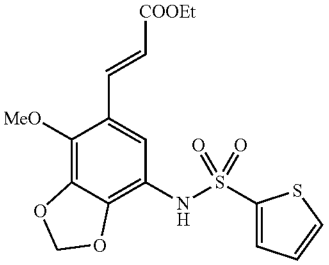 | 86 | 411 | 123 | na | >500 | (E)-ethyl 3-(4-methoxy-7-(thiophene-2-sulfonamido)benzo[d][1,3]dioxol-5-yl)acrylate |
| 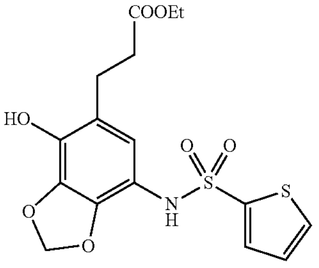 | 87 | 399 | na | na | na | ethyl 3-(4-hydroxy-7-(thiophene-2-sulfonamido)benzo[d][1,3]dioxol-5-yl)propanoate |

TABLE 2-continued

| Analogs modeled from Second Series Hits | | | | | | |
|---|---|---|---|---|---|---|
| Structure | CV No | Mol WT | CNK $K_D$ (μM) | PLEK $K_D$ (μM) | AKT $K_D$ (μM) | IUPAC Name |
| 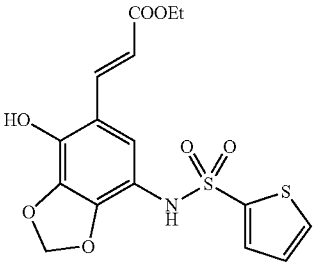 [SMILES: CCOC(=O)/C=C/c1cc(NS(=O)(=O)c2cccs2)c2c(c1O)OCO2] | 88 | 397 | 0.186 | 261.3 | 75.2 | (E)-ethyl 3-(4-hydroxy-7-(thiophene-2-sulfonamido)benzo[d][1,3]dioxol-5-yl)acrylate |
| 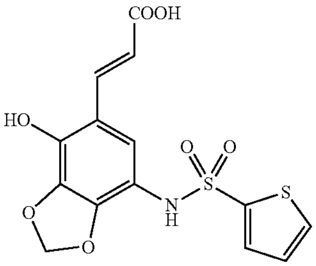 [SMILES: O=C(O)/C=C/c1cc(NS(=O)(=O)c2cccs2)c2c(c1O)OCO2] | 89 | 369 | 3.37 | na | ND | (E)-3-(4-hydroxy-7-(thiophene-2-sulfonamido)benzo[d][1,3]dioxol-5-yl)acrylic acid |
| 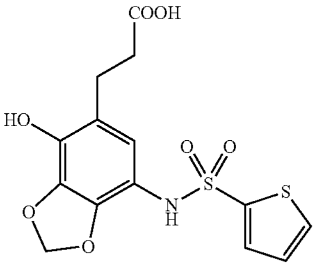 [SMILES: O=C(O)CCc1cc(NS(=O)(=O)c2cccs2)c2c(c1O)OCO2] | 90 | 371 | ND | na | ND | 3-(4-hydroxy-7-(thiophene-2-sulfonamido)benzo[d][1,3]dioxol-5-yl)propanoic acid |
| 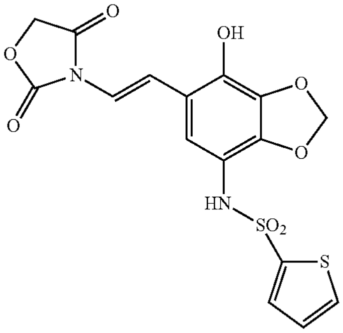 [SMILES: O=C1COC(=O)N1/C=C/c1cc(NS(=O)(=O)c2cccs2)c2c(c1O)OCO2] | 100 | 424 | | | | |

na = not analyzed;

ND = no binding determined

TABLE 3

| Analogs modeled from Second Series Hits | | | | | | |
|---|---|---|---|---|---|---|
| Cpd | | Mol WT | Log P | r_qp_Q PlogHERG | r_qp_QPPCaco | r_qp_% Human Oral Absorption |
| 91 | 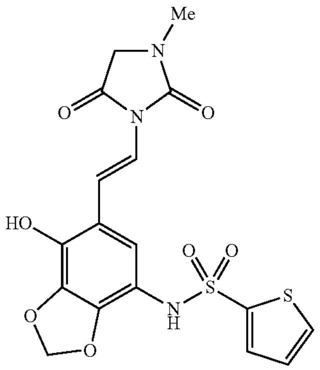 [SMILES: CN1CC(=O)N(/C=C/c2cc(NS(=O)(=O)c3cccs3)c3c(c2O)OCO3)C1=O] (E)-N-(7-hydroxy-6-(2-(3-methyl-2,5-dioxoimidazolidin-1-yl)vinyl)benzo[d][1,3]dioxol-4-yl)thiophene-2-sulfonamide | 436.45 | 0.85 | −5.26 | 74.60 | 66.54 |
| 92 | 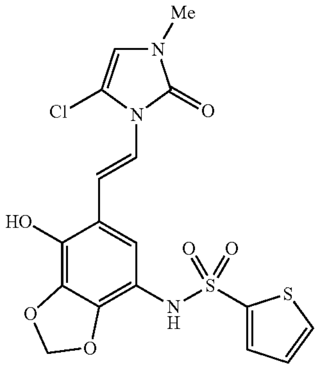 [SMILES: Cn1cc(Cl)n(/C=C/c2cc(NS(=O)(=O)c3cccs3)c3c(c2O)OCO3)c1=O] (E)-N-(6-(2-(5-chloro-3-methyl-2-oxo-2,3 dihydro-1H-imidazol-1-yl)vinyl)-7-hydroxybenzo[d][1,3]dioxol-4-yl)thiophene-2-sulfonamide | 454.89 | 2.44 | −5.48 | 203.24 | 81.64 |
| 93 | 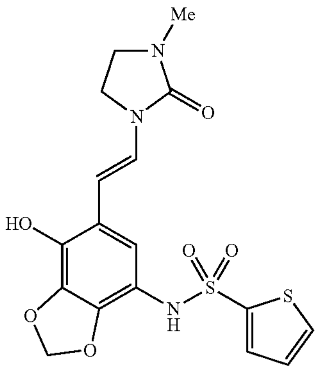 [SMILES: CN1CCN(/C=C/c2cc(NS(=O)(=O)c3cccs3)c3c(c2O)OCO3)C1=O] (E)-N-(7-hydroxy-6-(2-(3-methyl-2-oxoimidazolidin-1-yl)vinyl)benzo[d][1,3]dioxol-4-yl)thiophene-2-sulfonamide | 422.46 | 1.02 | −5.19 | 242.80 | 80.98 |

TABLE 3-continued

| Analogs modeled from Second Series Hits | | | | | | |
|---|---|---|---|---|---|---|
| Cpd | | Mol WT | Log P | r_qp_Q PlogHE RG | r_qp_QP PCaco | r_qp_% Human Oral Absorption |
| 94 | 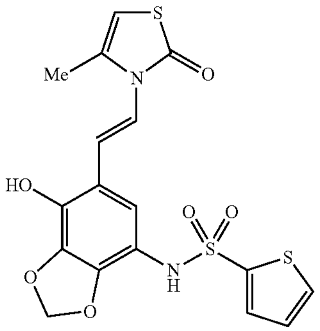 [SMILES: Cc1csc(=O)n1/C=C/c1cc(NS(=O)(=O)c2cccs2)c2c(c1O)OCO2] (E)-N-(7-hydroxy-6-(2-(4-methyl-2-oxothiazol-3(2H)-yl)vinyl)benzo[d][1,3]dioxol-4-yl)thiophene-2-sulfonamide | 437.5 | 2.44 | −5.07 | 222.80 | 80.30 |
| 95 | 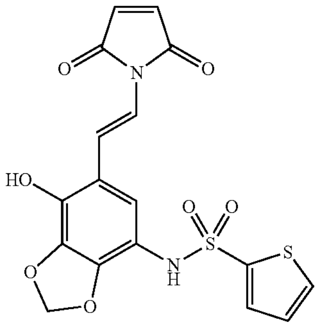 [SMILES: O=C1C=CC(=O)N1/C=C/c1cc(NS(=O)(=O)c2cccs2)c2c(c1O)OCO2] (E)-N-(6-(2-(2,5-dioxo-2,5-dihydro-1H-pyrrol-1-yl)vinyl)-7-hydroxybenzo[d][1,3]dioxol-4-yl)thiophene-2-sulfonamide | 419.41 | 1.53 | −5.30 | 62.10 | 64.54 |
| 96 | 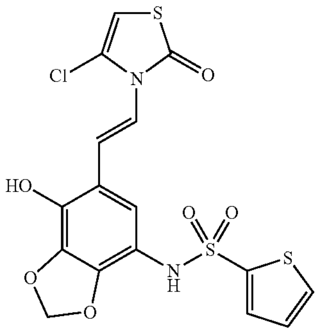 [SMILES: O=c1scc(Cl)n1/C=C/c1cc(NS(=O)(=O)c2cccs2)c2c(c1O)OCO2] (E)-N-(6-(2-(4-chloro-2-oxothiazol-3(2H)-yl)vinyl)-7-hydroxybenzo[d][1,3]dioxol-4-yl)thiophene-2-sulfonamide | 457.92 | 3.19 | −5.16 | 219.25 | 81.09 |

TABLE 3-continued

| Analogs modeled from Second Series Hits | | | | | | |
|---|---|---|---|---|---|---|
| Cpd | | Mol WT | Log P | r_qp_Q PlogHERG | r_qp_QP PCaco | r_qp_% Human Oral Absorption |
| 97 | 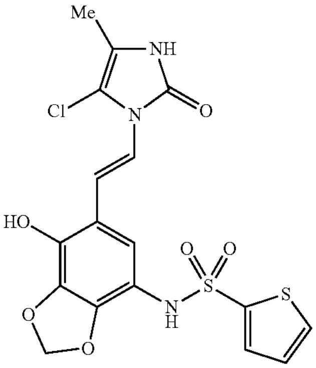 [SMILES: Cc1[nH]c(=O)n(/C=C/c2cc(NS(=O)(=O)c3cccs3)c3c(c2O)OCO3)c1Cl] (E)-N-(6-(2-(5-chloro-4-methyl-2-oxo-2,3-dihydro-1H-imidazol-1-yl)vinyl)-7-hydroxybenzo[d][1,3]dioxol-4-yl)thiophene-2-sulfonamide | 454.89 | 2.52 | −5.19 | 134.92 | 76.65 |
| 98 | 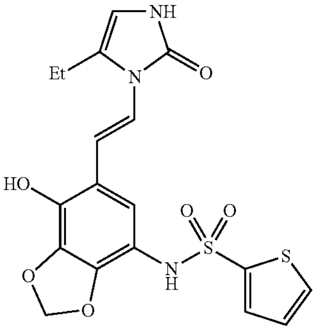 [SMILES: CCc1c[nH]c(=O)n1/C=C/c1cc(NS(=O)(=O)c2cccs2)c2c(c1O)OCO2] (E)-N-(6-(2-(5-ethyl-2-oxo-2,3-dihydro-1H-imidazol-1-yl)vinyl)-7-hydroxybenzo[d][1,3]dioxol-4-yl)thiophene-2-sulfonamide | 434.47 | 1.88 | −5.44 | 97.28 | 72.29 |
| 99 | 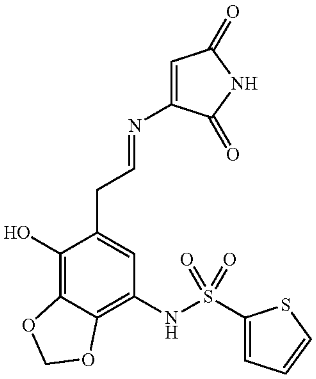 [SMILES: O=C1C=C(/N=C/Cc2cc(NS(=O)(=O)c3cccs3)c3c(c2O)OCO3)C(=O)N1] (E)-N-(6-(2-(2,5-dioxo-2,5-dihydro-1H-pyrrol-3-ylimino)ethyl)-7-hydroxybenzo[d][1,3]dioxol-4-yl)thiophene-2-sulfonamide | 434.43 | 0.56 | −4.34 | 21.39 | 51.02 |

TABLE 3-continued

| Analogs modeled from Second Series Hits | | | | | | |
|---|---|---|---|---|---|---|
| Cpd | | Mol WT | Log P | r_qp_Q PlogHE RG | r_qp_QP PCaco | r_qp_% Human Oral Absorption |
| 100 | 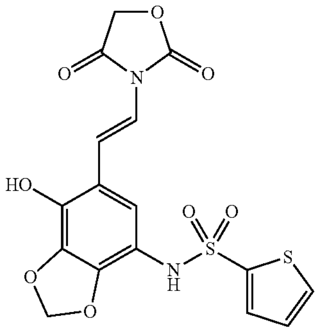 [SMILES: O=C1COC(=O)N1/C=C/c1cc(NS(=O)(=O)c2cccs2)c2c(c1O)OCO2]<br>(E)-N-(6-(2-(2,4-dioxooxazolidin-3-yl)vinyl)-7-hydroxybenzo[d][1,3]dioxol-4-yl)thiophene-2-sulfonamide | 423.4 | 1.1 | −4.64 | 60.93 | 59.71 |
| 101 | 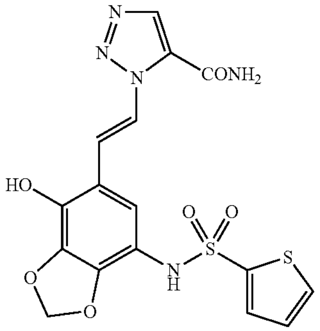 [SMILES: NC(=O)c1cnnn1/C=C/c1cc(NS(=O)(=O)c2cccs2)c2c(c1O)OCO2]<br>(E)-1-(2-(4-hydroxy-7-(thiophene-2-sulfonamido)benzo[d][1,3]dioxol-5-yl)vinyl)-1H-1,2,3-triazole-5-carboxamide | 434.43 | 0.17 | −5.46 | 14.91 | 34.24 |
| 102 | 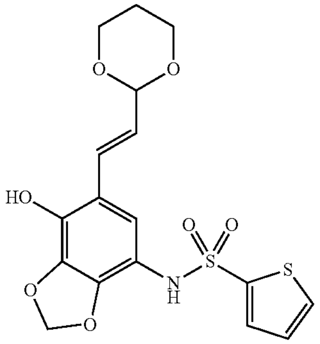 [SMILES: O=S(=O)(Nc1cc(/C=C/C2OCCCO2)c(O)c2c1OCO2)c1cccs1]<br>(E)-N-(6-(2-(1,3-dioxan-2-yl)vinyl)-7-hydroxybenzo[d][1,3]dioxol-4-yl)thiophene-2-sulfonamide | 410.44 | | | | |

TABLE 4
| Structure | Cpd. No. | Molecular Wt./Mass | SPR Competition Percent inhibition of CNK1 binding to PIP3 at 50 μM X = none. | Ave $IC_{50}$ mut-KRAS μM | Ave $IC_{50}$ wt-KRAS μM |
|---|---|---|---|---|---|
| Analogs modeled from Second Series Hits | | | | | |
| 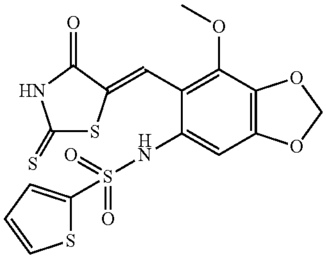 [SMILES: COc1c(/C=C2\SC(=S)NC2=O)c(NS(=O)(=O)c2cccs2)cc2c1OCO2] | 103 | Molecular wt: 456.54 Exact Mass: 455.96 | ND | 14.7 | 95 |
| 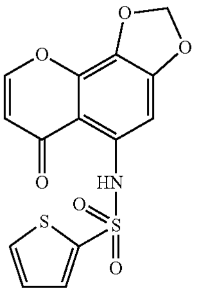 [SMILES: O=c1ccoc2c3c(cc(NS(=O)(=O)c4cccs4)c12)OCO3] | 104 | Molecular wt: 381.42 Exact Mass: 381.03 | X | 16.6 | 100 |
| 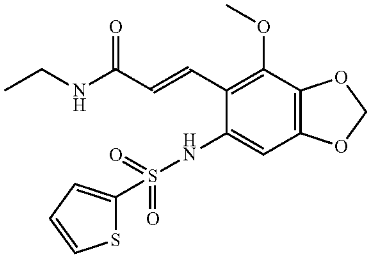 [SMILES: CCNC(=O)/C=C/c1c(NS(=O)(=O)c2cccs2)cc2c(c1OC)OCO2] | 105 | Molecular wt: 410.46 Exact Mass: 410.06 | 30 | 10 | 100 |
| 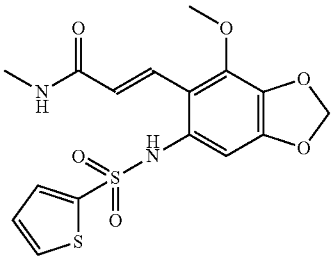 [SMILES: CNC(=O)/C=C/c1c(NS(=O)(=O)c2cccs2)cc2c(c1OC)OCO2] | 106 | Molecular wt: 396.44 Exact Mass: 396.04 | 50 | 8.4 | 68.0 |
| 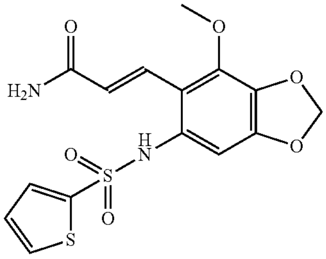 [SMILES: COc1c(/C=C/C(N)=O)c(NS(=O)(=O)c2cccs2)cc2c1OCO2] | 107 | Molecular wt: 382.41 Exact Mass: 382.03 | 45 | 1.5 | 100.0 |

TABLE 4-continued
Analogs modeled from Second Series Hits
| Structure | Cpd. No. | Molecular Wt./Mass | SPR Competition Percent inhibition of CNK1 binding to PIP3 at 50 µM X = none. | Ave $IC_{50}$ mut-KRAS µM | Ave $IC_{50}$ wt-KRAS µM |
|---|---|---|---|---|---|
| 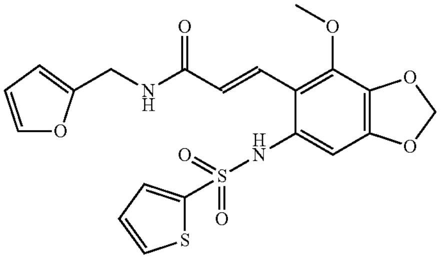 [SMILES: COc1c(/C=C/C(=O)NCc2ccco2)c(NS(=O)(=O)c2cccs2)cc2c1OCO2] | 108 | Molecular wt: 462.50 Exact Mass: 462.06 | 30 | 5.2 | 100 |
| 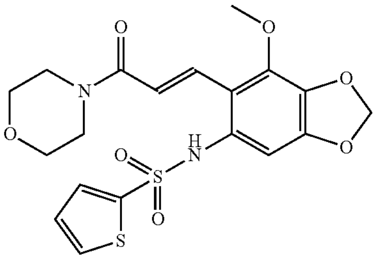 [SMILES: COc1c(/C=C/C(=O)N2CCOCC2)c(NS(=O)(=O)c2cccs2)cc2c1OCO2] | 109 | Molecular wt: 452.50 Exact Mass: 452.07 | 25 | 6.5 | 100 |
| 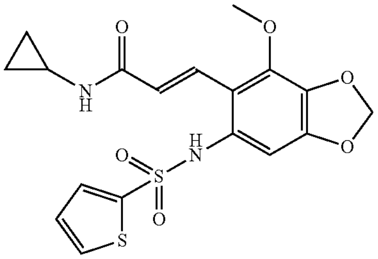 [SMILES: COc1c(/C=C/C(=O)NC2CC2)c(NS(=O)(=O)c2cccs2)cc2c1OCO2] | 110 | Molecular wt: 422.48 Exact Mass: 422.06 | X | 1.2 | 35.7 |
| 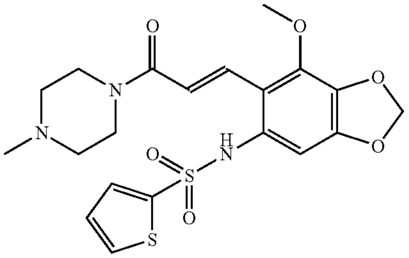 [SMILES: COc1c(/C=C/C(=O)N2CCN(C)CC2)c(NS(=O)(=O)c2cccs2)cc2c1OCO2] | 111 | Molecular wt: 465.54 Exact Mass: 465.10 | 85 | 4.1 | 33.7 |
| 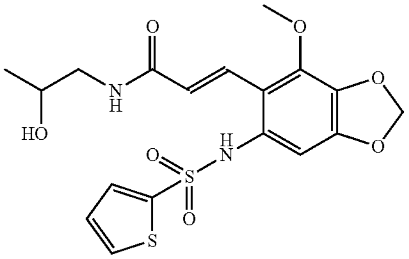 [SMILES: COc1c(/C=C/C(=O)NCC(C)O)c(NS(=O)(=O)c2cccs2)cc2c1OCO2] | 112 | Molecular wt: 440.49 Exact Mass: 440.07 | 50 | 25 | 100 |

TABLE 4-continued
| Analogs modeled from Second Series Hits | | | | | |
|---|---|---|---|---|---|
| Structure | Cpd. No. | Molecular Wt./Mass | SPR Competition Percent inhibition of CNK1 binding to PIP3 at 50 μM X = none. | Ave $IC_{50}$ mut-KRAS μM | Ave $IC_{50}$ wt-KRAS μM |
| 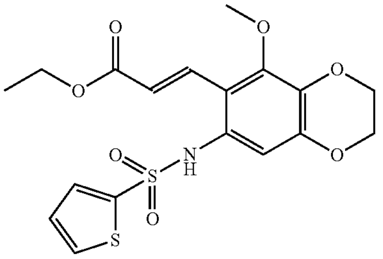 [SMILES: CCOC(=O)/C=C/c1c(NS(=O)(=O)c2cccs2)cc2c(c1OC)OCCO2] | 113 | Molecular wt: 425.48 Exact Mass: 425.06 | 15 | 55.1 | 100 |
| 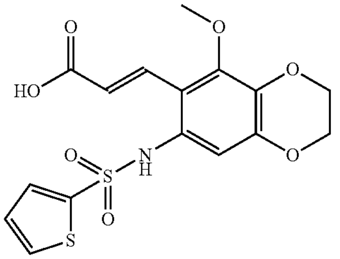 [SMILES: COc1c(/C=C/C(=O)O)c(NS(=O)(=O)c2cccs2)cc2c1OCCO2] | 114 | Molecular wt: 397.42 Exact Mass: 397.03 | 10 | 85 | 100 |
| 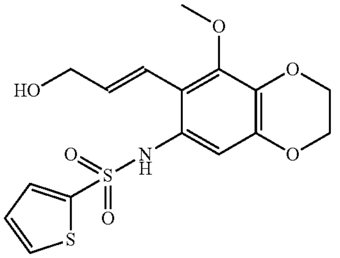 [SMILES: COc1c(/C=C/CO)c(NS(=O)(=O)c2cccs2)cc2c1OCCO2] | 115 | Molecular wt: 383.44 Exact Mass: 383.05 | 50 | 39.1 | 100 |
| 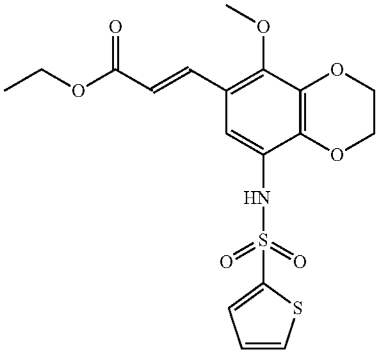 [SMILES: CCOC(=O)/C=C/c1cc(NS(=O)(=O)c2cccs2)c2c(c1OC)OCCO2] | 116 | Molecular wt: 425.48 Exact Mass: 425.06 | ND | 100 | ND |

TABLE 4-continued

| Analogs modeled from Second Series Hits | | | | | | |
|---|---|---|---|---|---|---|
| Structure | Cpd. No. | Molecular Wt./Mass | SPR Competition Percent inhibition of CNK1 binding to PIP3 at 50 μM X = none. | Ave $IC_{50}$ mut-KRAS μM | Ave $IC_{50}$ wt-KRAS μM |
| 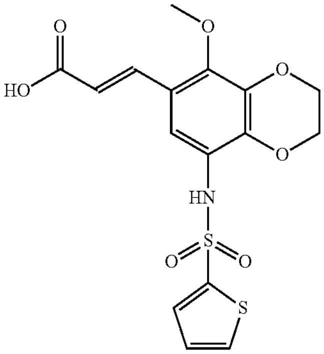 [SMILES: COc1c(/C=C/C(=O)O)cc(NS(=O)(=O)c2cccs2)c2c1OCCO2] | 117 | Molecular wt: 397.42 Exact Mass: 397.03 | ND | ND | ND |
| 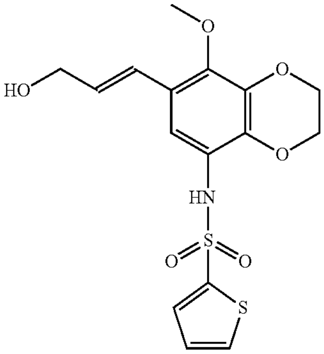 [SMILES: COc1c(/C=C/CO)cc(NS(=O)(=O)c2cccs2)c2c1OCCO2] | 118 | Molecular wt: 383.44 Exact Mass: 383.05 | ND | ND | ND |

TABLE 5

| Analogs modeled from Second Series Hits | | | |
|---|---|---|---|
| Compound Structure | Cmpd. No. | IUPAC Name | MW |
| 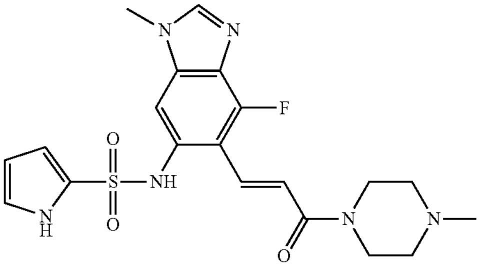 | 119 | N-{4-fluoro-1-methyl-5-[(1E)-3-(4-methylpiperazin-1-yl)-3-oxoprop-1-en-1-yl]-1H-1,3-benzodiazol-6-yl}-1H-pyrrole-2-sulfonamide | 446.51 |

TABLE 5-continued

Analogs modeled from Second Series Hits

| Compound Structure | Cmpd. No. | IUPAC Name | MW |
|---|---|---|---|
| 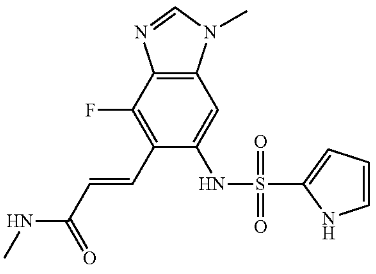 [SMILES: CNC(=O)/C=C/c1c(NS(=O)(=O)c2ccc[nH]2)cc2c(ncn2C)c1F] | 120 | (2E)-3-[4-fluoro-1-methyl-6-(1H-pyrrole-2-sulfonamido)-1H-1,3-benzodiazol-5-yl]-N-methylprop-2-enamide | 377.40 |
| 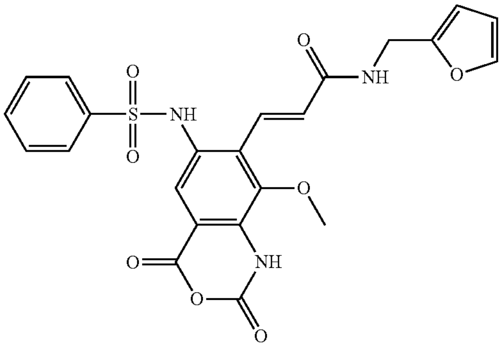 [SMILES: COc1c(/C=C/C(=O)NCc2ccco2)c(NS(=O)(=O)c2ccccc2)cc2c(=O)oc(=O)[nH]c12] | 121 | (2E)-3-(6-benzenesulfonamido-8-methoxy-2,4-dioxo-2,4-dihydro-1H-3,1-benzoxazin-7-yl)-N-(furan-2-ylmethyl)prop-2-enamide | 497.48 |
| 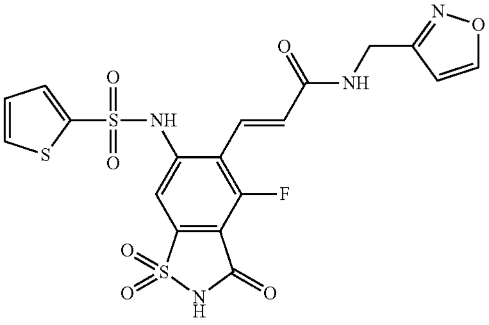 [SMILES: O=C(/C=C/c1c(NS(=O)(=O)c2cccs2)cc2c(c1F)C(=O)NS2(=O)=O)NCc1ccon1] | 122 | (2E)-3-[4-fluoro-1,1,3-trioxo-6-(thiophene-2-sulfonamido)-2,3-dihydro-1λ$^6$, 2-benzothiazol-5-yl]-N-(1,2-oxazol-3-ylmethyl)prop-2-enamide | 510.50 |
| 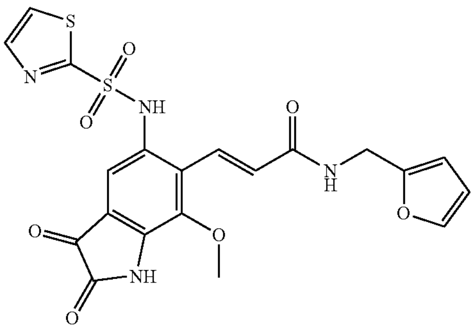 [SMILES: COc1c(/C=C/C(=O)NCc2ccco2)c(NS(=O)(=O)c2nccs2)cc2c1NC(=O)C2=O] | 123 | (2E)-N-(furan-2-ylmethyl)-3-[7-methoxy-2,3-dioxo-5-(1,3-thiazole-2-sulfonamido)-2,3-dihydro-1H-indol-6-yl]prop-2-enamide | 486.48 |

TABLE 5-continued

| Analogs modeled from Second Series Hits | | | |
|---|---|---|---|
| Compound Structure | Cmpd. No. | IUPAC Name | MW |
| 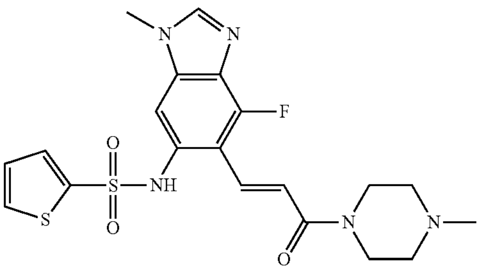 [SMILES: CN1CCN(C(=O)/C=C/c2c(NS(=O)(=O)c3cccs3)cc3c(ncn3C)c2F)CC1] | 124 | N-{4-fluoro-1-methyl-5-[(1E)-3-(4-methylpiperazin-1-yl)-3-oxoprop-1-en-1-yl]-1H-1,3-benzodiazol-6-yl}thiophene-2-sulfonamide | 462.55 |
| 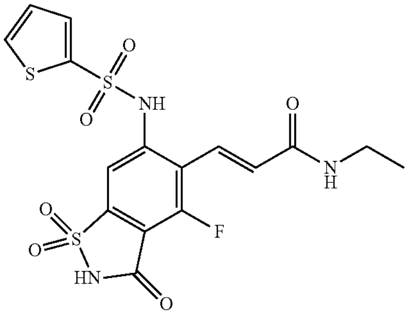 [SMILES: CCNC(=O)/C=C/c1c(NS(=O)(=O)c2cccs2)cc2c(c1F)C(=O)NS2(=O)=O] | 125 | (2E)-N-ethyl-3-[4-fluoro-1,1,3-trioxo-6-(thiophene-2-sulfonamido)-2,3-dihydro-1λ$^6$, 2-benzothiazol-5-yl]prop-2-enamide | 457.48 |
| 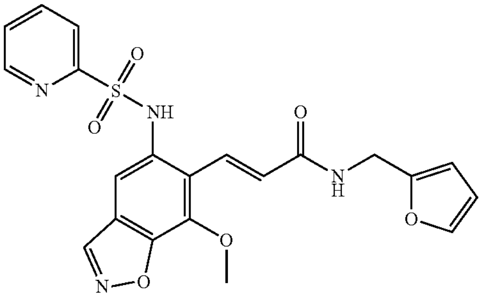 [SMILES: COc1c(/C=C/C(=O)NCc2ccco2)c(NS(=O)(=O)c2ccccn2)cc2cnoc12] | 126 | (2E)-N-(furan-2-ylmethyl)-3-[7-methoxy-5-(pyridine-2-sulfonamido)-1,2-benzoxazol-6-yl]prop-2-enamide | 453.45 |
| 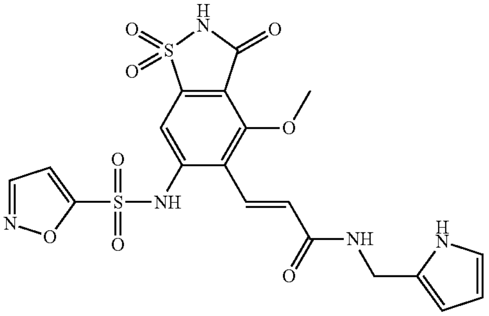 [SMILES: COc1c(/C=C/C(=O)NCc2ccc[nH]2)c(NS(=O)(=O)c2ccno2)cc2c1C(=O)NS2(=O)=O] | 127 | (2E)-3-[4-methoxy-6-(1,2-oxazole-5-sulfonamido)-1,1,3-trioxo-2,3-dihydro-1λ$^6$, 2-benzothiazol-5-yl]-N-(1H-pyrrol-2-ylmethyl)prop-2-enamide | 505.48 |
| 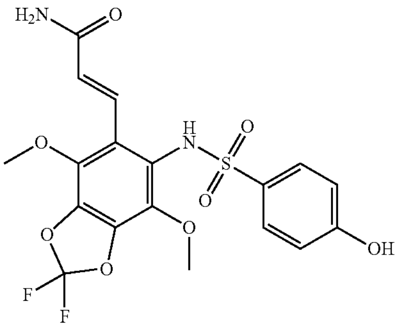 [SMILES: COc1c(/C=C/C(N)=O)c(NS(=O)(=O)c2ccc(O)cc2)c(OC)c2c1OC(F)(F)O2] | 128 | (2E)-3-[2,2-difluoro-6-(4-hydroxybenzenesulfonamido)-4,7-dimethoxy-2H-1,3-benzodioxol-5-yl]prop-2-enamide | 458.39 |

TABLE 5-continued

| Compound Structure | Cmpd. No. | IUPAC Name | MW |
|---|---|---|---|
| Analogs modeled from Second Series Hits | | | |
| 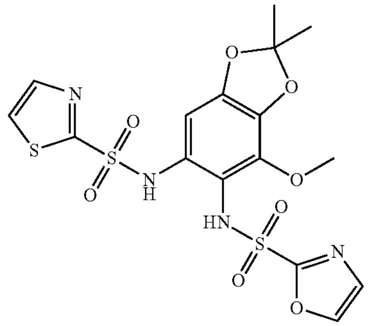 [SMILES: COc1c(NS(=O)(=O)c2ncco2)c(NS(=O)(=O)c2nccs2)cc2c1OC(C)(C)O2] | 129 | N-[4-methoxy-2,2-dimethyl-6-(1,3-thiazole-2-sulfonamido)-2H-1,3-benzodioxol-5-yl]-1,3-oxazole-2-sulfonamide | 487.51 |
| 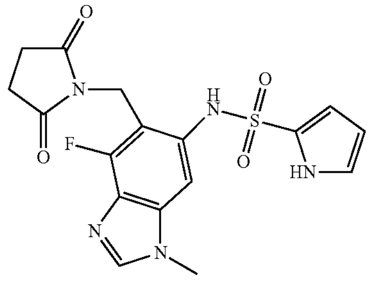 [SMILES: Cn1cnc2c(F)c(CN3C(=O)CCC3=O)c(NS(=O)(=O)c3ccc[nH]3)cc21] | 130 | N-{5-[(2,5-dioxopyrrolidin-1-yl)methyl]-4-fluoro-1-methyl-1H-1,3-benzodiazol-6-yl}-1H-pyrrole-2-sulfonamide | 404.40 |
| 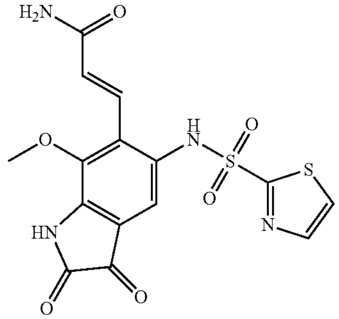 [SMILES: COc1c(/C=C/C(N)=O)c(NS(=O)(=O)c2nccs2)cc2c1NC(=O)C2=O] | 131 | (2E)-3-[7-methoxy-2,3-dioxo-5-(1,3-thiazole-2-sulfonamido)-2,3-dihydro-1H-indol-6-yl]prop-2-enamide | 406.40 |
| 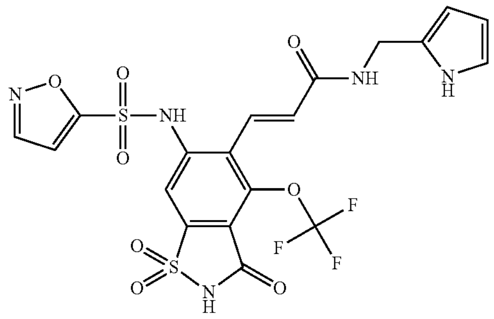 [SMILES: O=C(/C=C/c1c(NS(=O)(=O)c2ccno2)cc2c(c1OC(F)(F)F)C(=O)NS2(=O)=O)NCc1ccc[nH]1] | 132 | (2E)-3-[6-(1,2-oxazole-5-sulfonamido)-1,1,3-trioxo-4-(trifluoromethoxy)-2,3-dihydro-1λ$^6$, 2-benzothiazol-5-yl]-N-(1H-pyrrol-2-ylmethyl)prop-2-enamide | 560.47 |
| 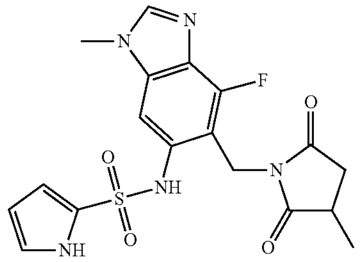 [SMILES: CC1CC(=O)N(Cc2c(NS(=O)(=O)c3ccc[nH]3)cc3c(ncn3C)c2F)C1=O] | 133 | N-{4-fluoro-1-methyl-5-[(3-methyl-2,5-dioxopyrrolidin-1-yl)methyl]-1H-1,3-benzodiazol-6-yl}-1H-pyrrole-2-sulfonamide | 419.44 |

TABLE 5-continued

Analogs modeled from Second Series Hits

| Compound Structure | Cmpd. No. | IUPAC Name | MW |
|---|---|---|---|
| 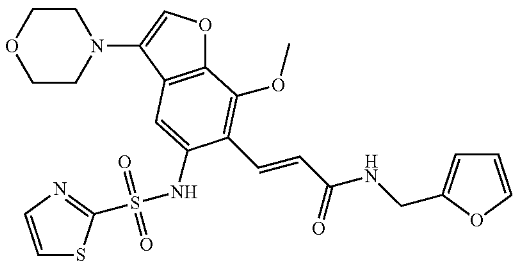 [SMILES: COc1c(/C=C/C(=O)NCc2ccco2)c(NS(=O)(=O)c2nccs2)cc2c(N3CCOCC3)coc12] | 134 | (2E)-N-(furan-2-ylmethyl)-3-[7-methoxy-3-(morpholin-4-yl)-5-(1,3-thiazole-2-sulfonamido)-1-benzofuran-6-yl]prop-2-enamide | 543.60 |
| 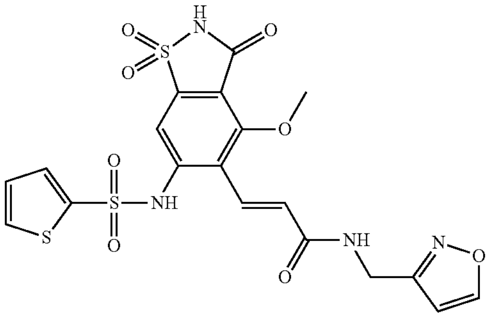 [SMILES: COc1c(/C=C/C(=O)NCc2ccon2)c(NS(=O)(=O)c2cccs2)cc2c1C(=O)NS2(=O)=O] | 135 | (2E)-3-[4-methoxy-1,1,3-trioxo-6-(thiophene-2-sulfonamido)-2,3-dihydro-1$\lambda^6$, 2-benzothiazol-5-yl]-N-(1,2-oxazol-3-ylmethyl)prop-2-enamide | 523.55 |
| 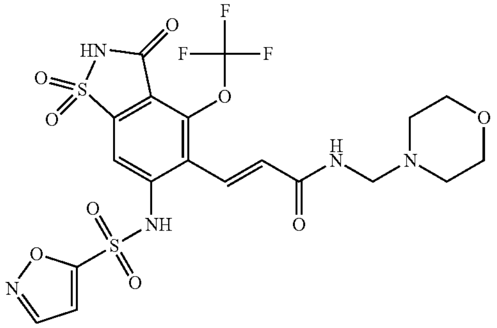 [SMILES: O=C(/C=C/c1c(NS(=O)(=O)c2ccno2)cc2c(c1OC(F)(F)F)C(=O)NS2(=O)=O)NCN1CCOCC1] | 136 | (2E)-N-(morpholin-4-ylmethyl)-3-[6-(1,2-oxazole-5-sulfonamido)-1,1,3-trioxo-4-(trifluoromethoxy)-2,3-dihydro-1$\lambda^6$, 2-benzothiazol-5-yl]prop-2-enamide | 580.50 |
| 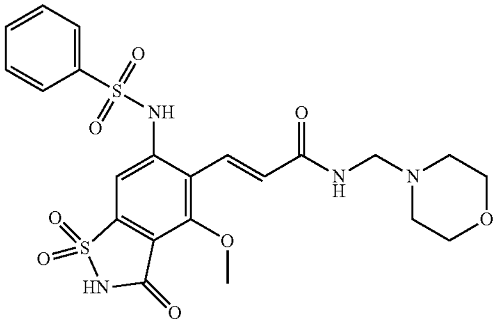 [SMILES: COc1c(/C=C/C(=O)NCN2CCOCC2)c(NS(=O)(=O)c2ccccc2)cc2c1C(=O)NS2(=O)=O] | 137 | (2E)-3-(6-benzenesulfonamido-4-methoxy-1,1,3-trioxo-2,3-dihydro-1$\lambda^6$, 2-benzothiazol-5-yl)-N-(morpholin-4-ylmethyl)prop-2-enamide | 535.58 |
| 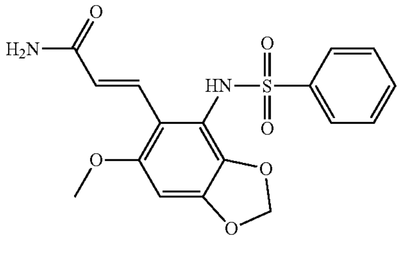 [SMILES: COc1cc2c(c(NS(=O)(=O)c3ccccc3)c1/C=C/C(N)=O)OCO2] | 138 | (2E)-3-(4-benzenesulfonamido-6-methoxy-2H-1,3-benzodioxol-5-yl)prop-2-enamide | 376.39 |

TABLE 5-continued

| Analogs modeled from Second Series Hits | | | |
|---|---|---|---|
| Compound Structure | Cmpd. No. | IUPAC Name | MW |
| 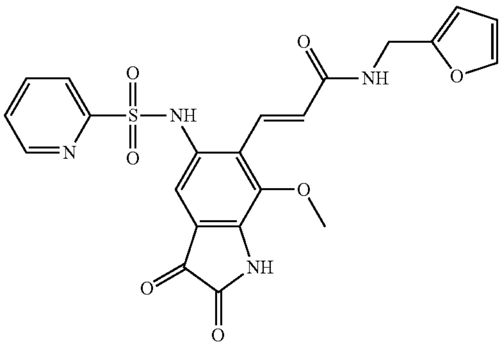 [SMILES: COc1c(/C=C/C(=O)NCc2ccco2)c(NS(=O)(=O)c2ccccn2)cc2c1NC(=O)C2=O] | 139 | (2E)-N-(furan-2-ylmethyl)-3-[7-methoxy-2,3-dioxo-5-(pyridine-2-sulfonamido)-2,3-dihydro-1H-indol-6-yl]prop-2-enamide | 481.47 |
| 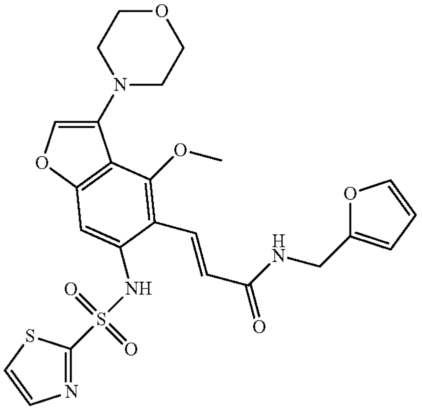 [SMILES: COc1c(/C=C/C(=O)NCc2ccco2)c(NS(=O)(=O)c2nccs2)cc2occ(N3CCOCC3)c12] | 140 | (2E)-N-(furan-2-ylmethyl)-3-[4-methoxy-3-(morpholin-4-yl)-6-(1,3-thiazole-2-sulfonamido)-1-benzofuran-5-yl]prop-2-enamide | 543.60 |
| 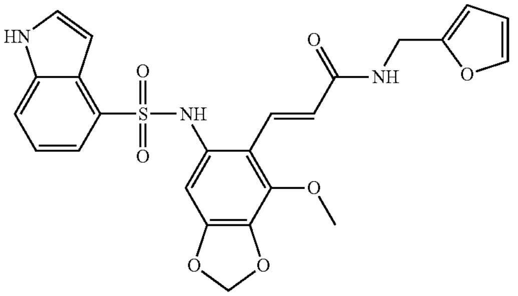 [SMILES: COc1c(/C=C/C(=O)NCc2ccco2)c(NS(=O)(=O)c2cccc3[nH]ccc23)cc2c1OCO2] | 141 | (2E)-N-(furan-2-ylmethyl)-3-[6-(1H-indole-4-sulfonamido)-4-methoxy-2H-1,3-benzodioxol-5-yl]prop-2-enamide | 495.51 |
| 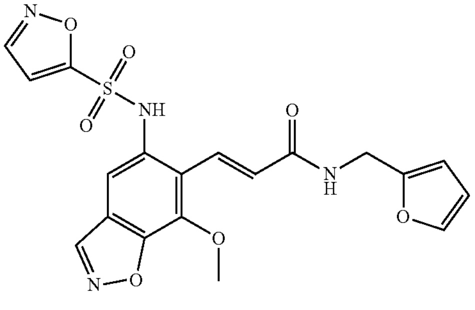 [SMILES: COc1c(/C=C/C(=O)NCc2ccco2)c(NS(=O)(=O)c2ccno2)cc2cnoc12] | 142 | (2E)-N-(furan-2-ylmethyl)-3-[7-methoxy-5-(1,2-oxazole-5-sulfonamido)-1,2-benzoxazol-6-yl]prop-2-enamide | 444.42 |

TABLE 5-continued

Analogs modeled from Second Series Hits

| Compound Structure | Cmpd. No. | IUPAC Name | MW |
|---|---|---|---|
| 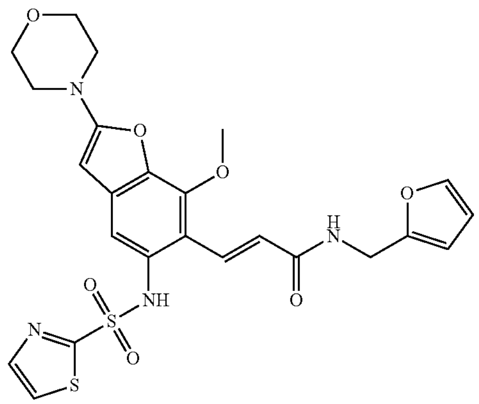 [SMILES: COc1c(/C=C/C(=O)NCc2ccco2)c(NS(=O)(=O)c2nccs2)cc2cc(N3CCOCC3)oc12] | 143 | (2E)-N-(furan-2-ylmethyl)-3-[7-methoxy-2-(morpholin-4-yl)-5-(1,3-thiazole-2-sulfonamido)-1-benzofuran-6-yl]prop-2-enamide | 543.60 |
| 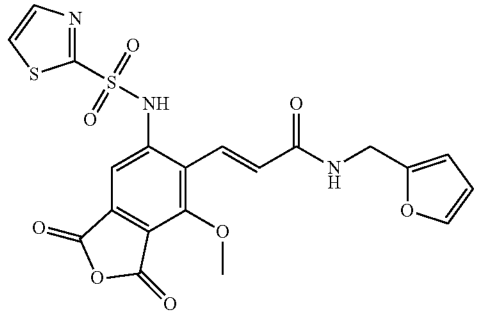 [SMILES: COc1c(/C=C/C(=O)NCc2ccco2)c(NS(=O)(=O)c2nccs2)cc2c1C(=O)OC2=O] | 144 | (2E)-N-(furan-2-ylmethyl)-3-[4-methoxy-1,3-dioxo-6-(1,3-thiazole-2-sulfonamido)-1,3-dihydro-2-benzofuran-5-yl]prop-2-enamide | 488.48 |
| 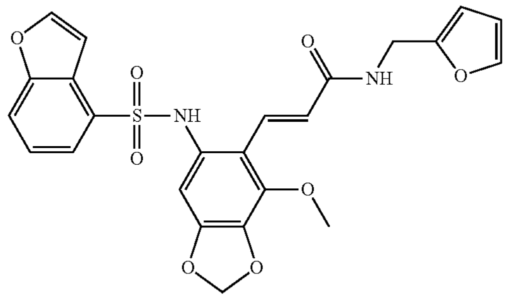 [SMILES: COc1c(/C=C/C(=O)NCc2ccco2)c(NS(=O)(=O)c2cccc3occc23)cc2c1OCO2] | 145 | (2E)-3-[6-(1-benzofuran-4-sulfonamido)-4-methoxy-2H-1,3-benzodioxol-5-yl]-N-(furan-2-ylmethyl)prop-2-enamide | 495.498 |
| 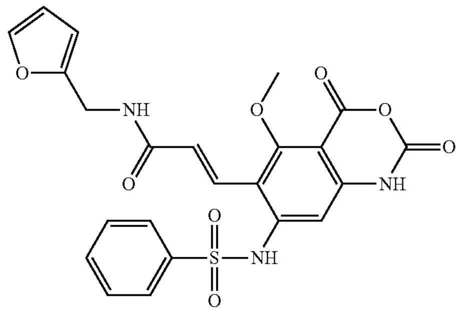 [SMILES: COc1c(/C=C/C(=O)NCc2ccco2)c(NS(=O)(=O)c2ccccc2)cc2[nH]c(=O)oc(=O)c12] | 146 | (2E)-3-(7-benzenesulfonamido-5-methoxy-2,4-dioxo-2,4-dihydro-1H-3,1-benzoxazin-6-yl)-N-(furan-2-ylmethyl)prop-2-enamide | 496.48 |

TABLE 5-continued

| Analogs modeled from Second Series Hits | | | |
|---|---|---|---|
| Compound Structure | Cmpd. No. | IUPAC Name | MW |
| 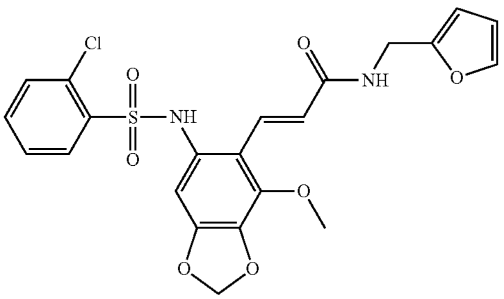 [SMILES: COc1c(/C=C/C(=O)NCc2ccco2)c(NS(=O)(=O)c2ccccc2Cl)cc2c1OCO2] | 147 | (2E)-3-[6-(2-chlorobenzenesulfonamido)-4-methoxy-2H-1,3-benzodioxol-5-yl]-N-(furan-2-ylmethyl)prop-2-enamide | 490.92 |
| 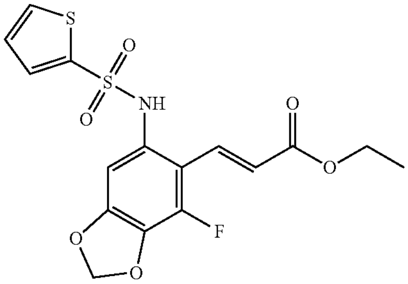 [SMILES: CCOC(=O)/C=C/c1c(NS(=O)(=O)c2cccs2)cc2c(c1F)OCO2] | 148 | ethyl (2E)-3-[4-fluoro-6-(thiophene-2-sulfonamido)-2H-1,3-benzodioxol-5-yl]prop-2-enoate | 399.42 |
| 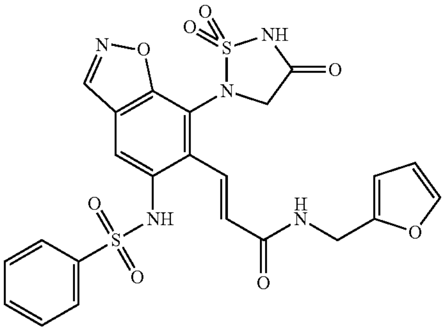 [SMILES: O=C(/C=C/c1c(NS(=O)(=O)c2ccccc2)cc2cnoc2c1N1CC(=O)NS1(=O)=O)NCc1ccco1] | 149 | (2E)-3-[5-benzenesulfonamido-7-(1,1,4-trioxo-1λ$^6$, 2,5-thiadiazolidin-2-yl)-1,2-benzoxazol-6-yl]-N-(furan-2-ylmethyl)prop-2-enamide | 557.56 |
| 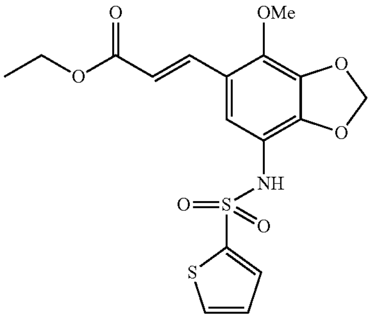 [SMILES: CCOC(=O)/C=C/c1cc(NS(=O)(=O)c2cccs2)c2c(c1OC)OCO2] | 150 | ethyl (2E)-3-[4-methoxy-7-(thiophene-2-sulfonamido)-2H-1,3-benzodioxol-5-yl]prop-2-enoate | 411 |
| 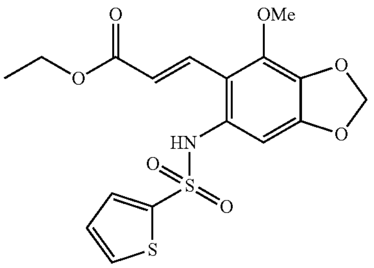 [SMILES: CCOC(=O)/C=C/c1c(NS(=O)(=O)c2cccs2)cc2c(c1OC)OCO2] | 151 | ethyl 3-[4-methoxy-6-(thiophene-2-sulfonamido)-2H-1,3-benzodioxol-5-yl]prop-2-enoate | 411 |

TABLE 5-continued

| Analogs modeled from Second Series Hits | | | |
|---|---|---|---|
| Compound Structure | Cmpd. No. | IUPAC Name | MW |
| 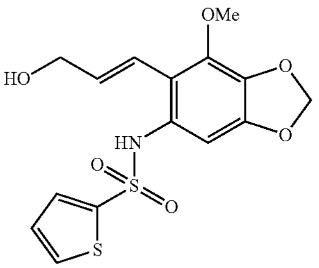 [SMILES: COc1c(/C=C/CO)c(NS(=O)(=O)c2cccs2)cc2c1OCO2] | 152 | N-{6-[(1E)-3-hydroxyprop-1-en-1-yl]-7-methoxy-2H-1,3-benzodioxol-5-yl}thiophene-2-sulfonamide | 369 |
| 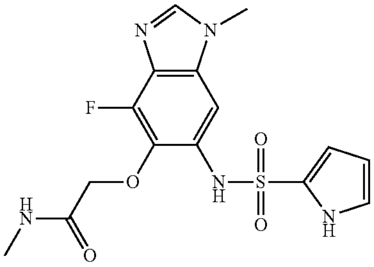 [SMILES: CNC(=O)COc1c(NS(=O)(=O)c2ccc[nH]2)cc2c(ncn2C)c1F] | 153 | 2-{[4-fluoro-1-methyl-6-(1H-pyrrole-2-sulfonamido)-1H-1,3-benzodiazol-5-yl]oxy}-N-methylacetamide | 381.39 |
| 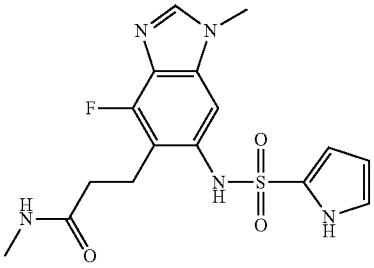 | 154 | 3-[4-fluoro-1-methyl-6-(1H-pyrrole-2-sulfonamido)-1H-1,3-benzodiazol-5-yl]-N-methylpropanamide | 379.42 |
| 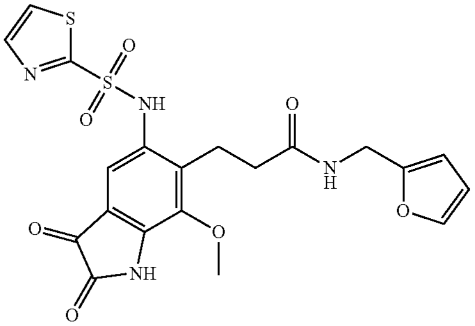 [SMILES: COc1c(CCC(=O)NCc2ccco2)c(NS(=O)(=O)c2nccs2)cc2c1NC(=O)C2=O] | 155 | N-(furan-2-ylmethyl)-3-[7-methoxy-2,3-dioxo-5-(1,3-thiazole-2-sulfonamido)-2,3-dihydro-1H-indol-6-yl]propanamide | 490.52 |
| 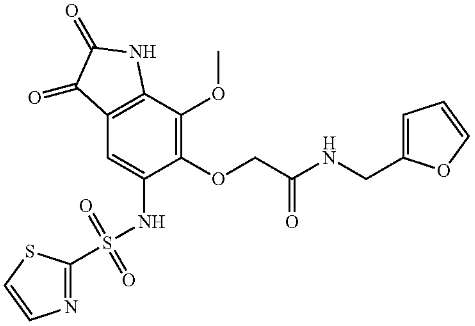 [SMILES: COc1c2c(cc(NS(=O)(=O)c3nccs3)c1OCC(=O)NCc1ccco1)C(=O)C(=O)N2] | 156 | N-(furan-2-ylmethyl)-2-{[7-methoxy-2,3-dioxo-5-(1,3-thiazole-2-sulfonamido)-2,3-dihydro-1H-indol-6-yl]oxy}acetamide | 492.49 |

TABLE 5-continued

Analogs modeled from Second Series Hits

| Compound Structure | Cmpd. No. | IUPAC Name | MW |
|---|---|---|---|
| 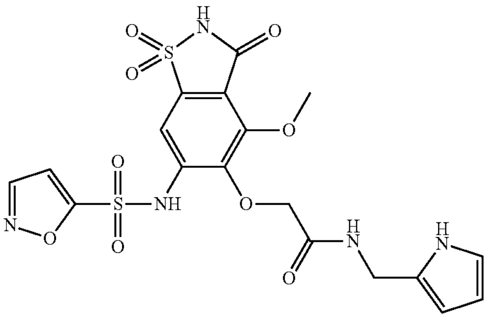 [SMILES: COc1c(OCC(=O)NCc2ccc[nH]2)c(NS(=O)(=O)c2ccno2)cc2c1C(=O)NS2(=O)=O] | 157 | 2-{[4-methoxy-6-(1,2-oxazole-5-sulfonamido)-1,1,3-trioxo-2,3-dihydro-1$\lambda^6$, 2-benzothiazol-5-yl]oxy}-N-(1H-pyrrol-2-ylmethyl)acetamide | 511.49 |
| 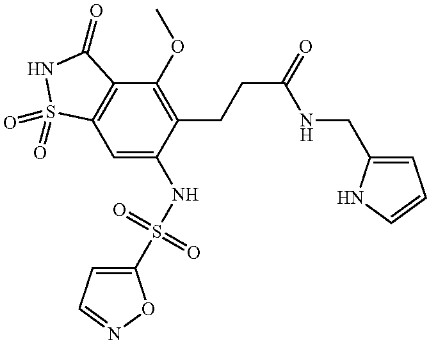 [SMILES: COc1c(CCC(=O)NCc2ccc[nH]2)c(NS(=O)(=O)c2ccno2)cc2c1C(=O)NS2(=O)=O] | 158 | 3-[4-methoxy-6-(1,2-oxazole-5-sulfonamido)-1,1,3-trioxo-2,3-dihydro-1$\lambda^6$, 2-benzothiazol-5-yl]-N-(1H-pyrrol-2-ylmethyl)propanamide | 509.52 |
| 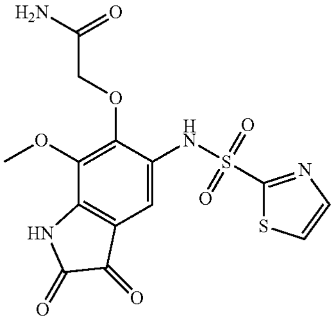 [SMILES: COc1c2c(cc(NS(=O)(=O)c3nccs3)c1OCC(N)=O)C(=O)C(=O)N2] | 159 | 2-{[7-methoxy-2,3-dioxo-5-(1,3-thiazole-2-sulfonamido)-2,3-dihydro-1H-indol-6-yl]oxy}acetamide | 412.40 |
| 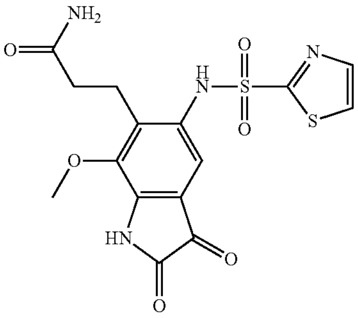 [SMILES: COc1c(CCC(N)=O)c(NS(=O)(=O)c2nccs2)cc2c1NC(=O)C2=O] | 160 | 3-[7-methoxy-2,3-dioxo-5-(1,3-thiazole-2-sulfonamido)-2,3-dihydro-1H-indol-6-yl]propanamide | 410.43 |

TABLE 5-continued

Analogs modeled from Second Series Hits

| Compound Structure | Cmpd. No. | IUPAC Name | MW |
|---|---|---|---|
| 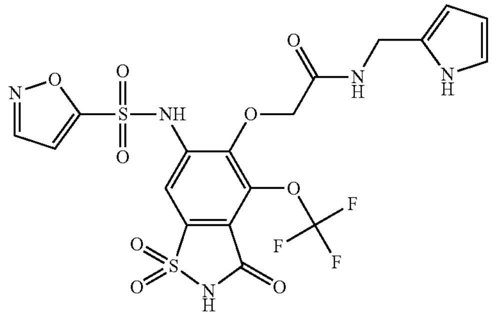 [SMILES: O=C(COc1c(NS(=O)(=O)c2ccno2)cc2c(c1OC(F)(F)F)C(=O)NS2(=O)=O)NCc1ccc[nH]1] | 161 | 2-{[6-(1,2-oxazole-5-sulfonamido)-1,1,3-trioxo-4-(trifluoromethoxy)-2,3-dihydro-1λ$^6$, 2-benzothiazol-5-yl]oxy}-N-(1H-pyrrol-2-ylmethyl)acetamide | 565.46 |
| 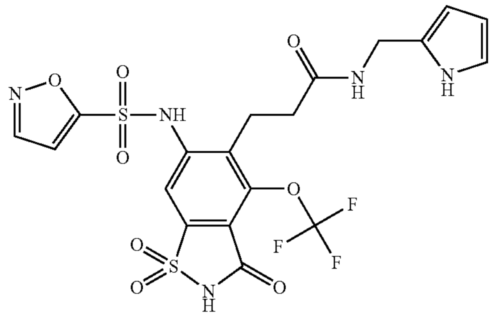 [SMILES: O=C(CCc1c(NS(=O)(=O)c2ccno2)cc2c(c1OC(F)(F)F)C(=O)NS2(=O)=O)NCc1ccc[nH]1] | 162 | 3-[6-(1,2-oxazole-5-sulfonamido)-1,1,3-trioxo-4-(trifluoromethoxy)-2,3-dihydro-1λ$^6$, 2-benzothiazol-5-yl]-N-(1H-pyrrol-2-ylmethyl)propanamide | 563.49 |
| 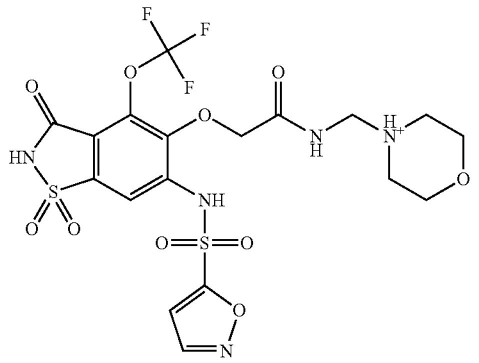 | 163 | N-(morpholin-4-ylmethyl)-2-{[6-(1,2-oxazole-5-sulfonamido)-1,1,3-trioxo-4-(trifluoromethoxy)-2,3-dihydro-1λ$^6$, 2-benzothiazol-5-yl]oxy}acetamide | 586.50 |
| 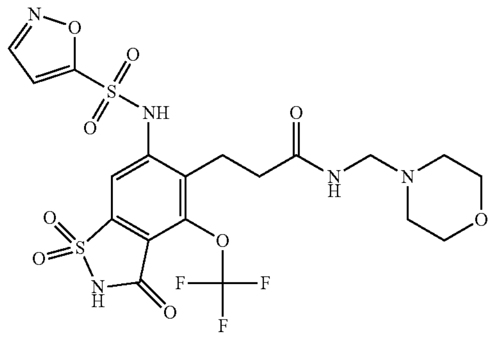 [SMILES: O=C(CCc1c(NS(=O)(=O)c2ccno2)cc2c(c1OC(F)(F)F)C(=O)NS2(=O)=O)NCN1CCOCC1] | 164 | N-(morpholin-4-ylmethyl)-3-[6-(1,2-oxazole-5-sulfonamido)-1,1,3-trioxo-4-(trifluoromethoxy)-2,3-dihydro-1λ$^6$, 2-benzothiazol-5-yl]propanamide | 583.52 |

TABLE 5-continued

| Analogs modeled from Second Series Hits | | | |
|---|---|---|---|
| Compound Structure | Cmpd. No. | IUPAC Name | MW |
| 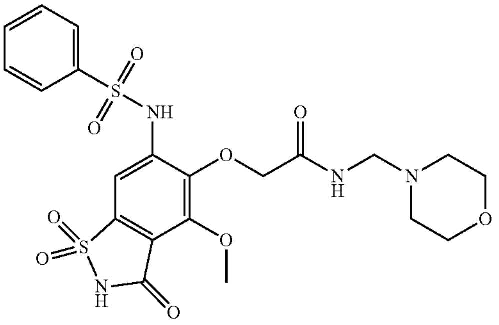 [SMILES: COc1c(OCC(=O)NCN2CCOCC2)c(NS(=O)(=O)c2ccccc2)cc2c1C(=O)NS2(=O)=O] | 165 | 2-[(6-benzenesulfonamido-4-methoxy-1,1,3-trioxo-2,3-dihydro-1λ[6], 2-benzothiazol-5-yl)oxy]-N-(morpholin-4-ylmethyl)acetamide | 540.57 |
| 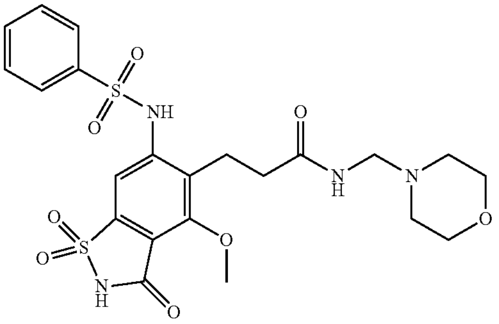 [SMILES: COc1c(CCC(=O)NCN2CCOCC2)c(NS(=O)(=O)c2ccccc2)cc2c1C(=O)NS2(=O)=O] | 166 | 3-(6-benzenesulfonamido-4-methoxy-1,1,3-trioxo-2,3-dihydro-1λ[6], 2-benzothiazol-5-yl)-N-(morpholin-4-ylmethyl)propanamide | 538.60 |
| 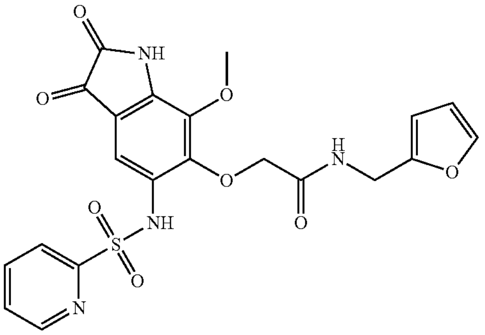 [SMILES: COc1c2c(cc(NS(=O)(=O)c3ccccn3)c1OCC(=O)NCc1ccco1)C(=O)C(=O)N2] | 167 | N-(furan-2-ylmethyl)-2-{[7-methoxy-2,3-dioxo-5-(pyridine-2-sulfonamido)-2,3-dihydro-1H-indol-6-yl]oxy}acetamide | 486.46 |
| 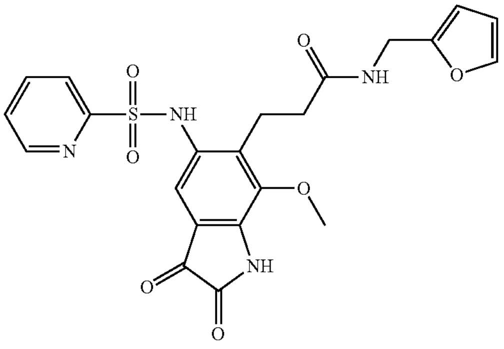 [SMILES: COc1c(CCC(=O)NCc2ccco2)c(NS(=O)(=O)c2ccccn2)cc2c1NC(=O)C2=O] | 168 | N-(furan-2-ylmethyl)-3-[7-methoxy-2,3-dioxo-5-(pyridine-2-sulfonamido)-2,3-dihydro-1H-indol-6-yl]propanamide | 484.49 |

TABLE 5-continued

| Analogs modeled from Second Series Hits | | | |
|---|---|---|---|
| Compound Structure | Cmpd. No. | IUPAC Name | MW |
| 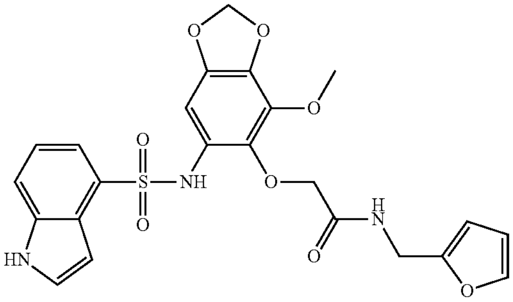 [SMILES: COc1c(OCC(=O)NCc2ccco2)c(NS(=O)(=O)c2cccc3[nH]ccc23)cc2c1OCO2] | 169 | N-(furan-2-ylmethyl)-2-{[6-(1H-indole-4-sulfonamido)-4-methoxy-2H-1,3-benzodioxol-5-yl]oxy}acetamide | 499.5 |
| 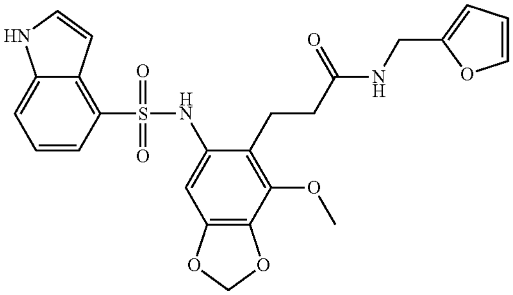 [SMILES: COc1c(CCC(=O)NCc2ccco2)c(NS(=O)(=O)c2cccc3[nH]ccc23)cc2c1OCO2] | 170 | N-(furan-2-ylmethyl)-3-[6-(1H-indole-4-sulfonamido)-4-methoxy-2H-1,3-benzodioxol-5-yl]propanamide | 497.53 |
| 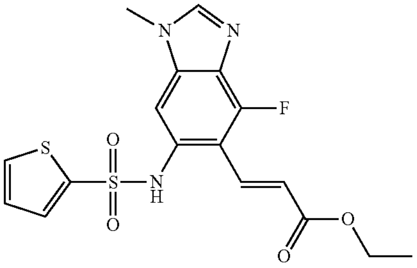 [SMILES: CCOC(=O)/C=C/c1c(NS(=O)(=O)c2cccs2)cc2c(ncn2C)c1F] | 171 | ethyl (2E)-3-[4-fluoro-1-methyl-6-(thiophene-2-sulfonamido)-1H-1,3-benzodiazol-5-yl]prop-2-enoate | 409.46 |
| 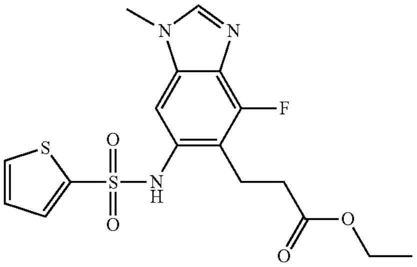 [SMILES: CCOC(=O)CCc1c(NS(=O)(=O)c2cccs2)cc2c(ncn2C)c1F] | 172 | ethyl 3-[4-fluoro-1-methyl-6-(thiophene-2-sulfonamido)-1H-1,3-benzodiazol-5-yl]propanoate | 411.47 |
| 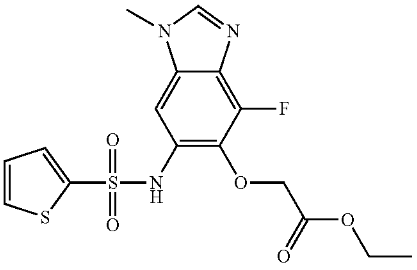 [SMILES: CCOC(=O)COc1c(NS(=O)(=O)c2cccs2)cc2c(ncn2C)c1F] | 173 | ethyl 2-{[4-fluoro-1-methyl-6-(thiophene-2-sulfonamido)-1H-1,3-benzodiazol-5-yl]oxy}acetate | 413.45 |

TABLE 5-continued

Analogs modeled from Second Series Hits

| Compound Structure | Cmpd. No. | IUPAC Name | MW |
|---|---|---|---|
| 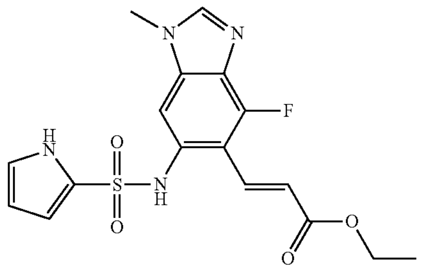 | 174 | ethyl (2E)-3-[4-fluoro-1-methyl-6-(1H-pyrrole-2-sulfonamido)-1H-1,3-benzodiazol-5-yl]prop-2-enoate | 392.41 |
| 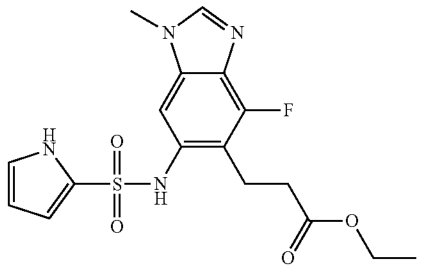 | 175 | ethyl 3-[4-fluoro-1-methyl-6-(1H-pyrrole-2-sulfonamido)-1H-1,3-benzodiazol-5-yl]propanoate | 394.42 |
| 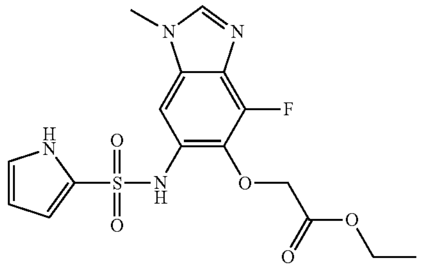 [SMILES: CCOC(=O)CCc1c(NS(=O)(=O)c2ccc[nH]2)cc2c(ncn2C)c1F] | 176 | ethyl 2-{[4-fluoro-1-methyl-6-(1H-pyrrole-2-sulfonamido)-1H-1,3-benzodiazol-5-yl]oxy}acetate | 396.39 |
| 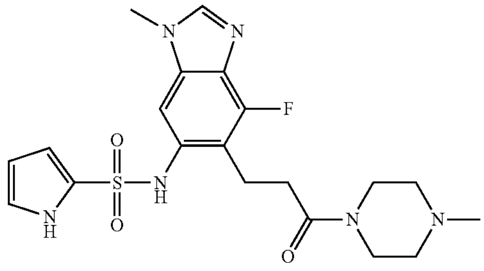 [SMILES: CN1CCN(C(=O)CCc2c(NS(=O)(=O)c3ccc[nH]3)cc3c(ncn3C)c2F)CC1] | 177 | N-{4-fluoro-1-methyl-5-[3-(4-methylpiperazin-1-yl)-3-oxopropyl]-1H-1,3-benzodiazol-6-yl}-1H-pyrrole-2-sulfonamide | 448.17 |
| 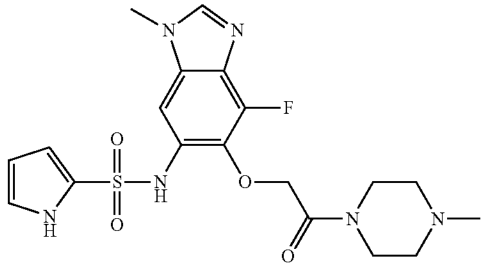 [SMILES: CN1CCN(C(=O)COc2c(NS(=O)(=O)c3ccc[nH]3)cc3c(ncn3C)c2F)CC1] | 178 | N-{4-fluoro-1-methyl-5-[2-(4-methylpiperazin-1-yl)-2-oxoethoxy]-1H-1,3-benzodiazol-6-yl}-1H-pyrrole-2-sulfonamide | 450.49 |

TABLE 5-continued

| Analogs modeled from Second Series Hits | | | |
|---|---|---|---|
| Compound Structure | Cmpd. No. | IUPAC Name | MW |
| 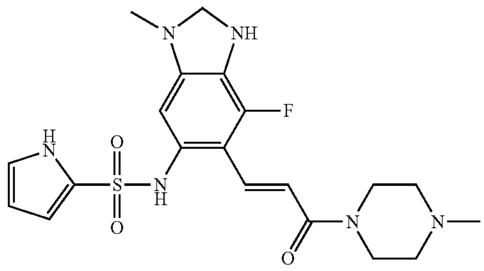 [SMILES: CN1CCN(C(=O)/C=C/c2c(NS(=O)(=O)c3ccc[nH]3)cc3c(c2F)NCN3C)CC1] | 179 | N-{7-fluoro-3-methyl-6-[(1E)-3-(4-methylpiperazin-1-yl)-3-oxoprop-1-en-1-yl]-2,3-dihydro-1H-1,3-benzodiazol-5-yl}-1H-pyrrole-2-sulfonamide | 448.52 |
| 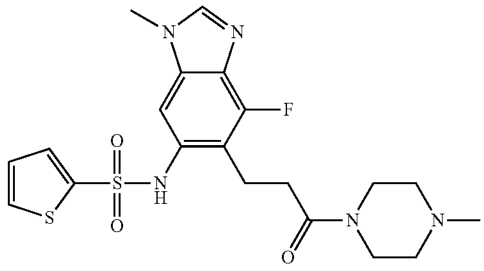 [SMILES: CN1CCN(C(=O)CCc2c(NS(=O)(=O)c3cccs3)cc3c(ncn3C)c2F)CC1] | 180 | N-{4-fluoro-1-methyl-5-[3-(4-methylpiperazin-1-yl)-3-oxopropyl]-1H-1,3-benzodiazol-6-yl}thiophene-2-sulfonamide | 465.57 |
| 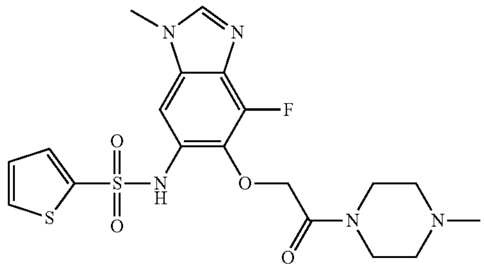 [SMILES: CN1CCN(C(=O)COc2c(NS(=O)(=O)c3cccs3)cc3c(ncn3C)c2F)CC1] | 181 | N-{4-fluoro-1-methyl-5-[2-(4-methylpiperazin-1-yl)-2-oxoethoxy]-1H-1,3-benzodiazol-6-yl}thiophene-2-sulfonamide | 467.55 |
| 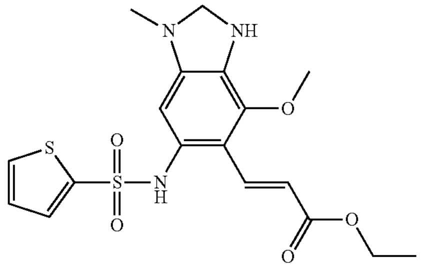 [SMILES: CCOC(=O)/C=C/c1c(NS(=O)(=O)c2cccs2)cc2c(c1OC)NCN2C] | 182 | ethyl (2E)-3-[4-methoxy-1-methyl-6-(thiophene-2-sulfonamido)-2,3-dihydro-1H-1,3-benzodiazol-5-yl]prop-2-enoate | 423.51 |
| 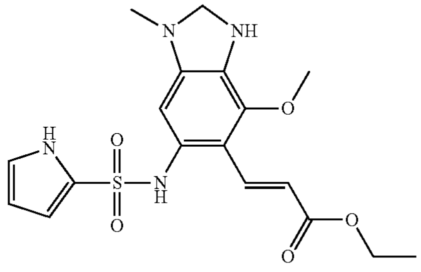 | 183 | ethyl (2E)-3-[4-methoxy-1-methyl-6-(1H-pyrrole-2-sulfonamido)-2,3-dihydro-1H-1,3-benzodiazol-5-yl]prop-2-enoate | 406.46298 |

TABLE 5-continued

| Analogs modeled from Second Series Hits | | | |
|---|---|---|---|
| Compound Structure | Cmpd. No. | IUPAC Name | MW |
| 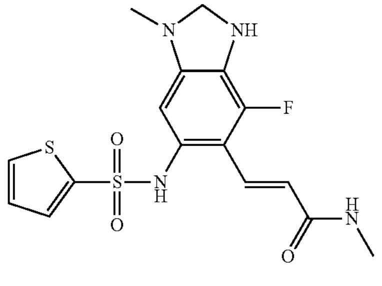 [SMILES: CNC(=O)/C=C/c1c(NS(=O)(=O)c2cccs2)cc2c(c1F)NCN2C] | 184 | (2E)-3-[4-fluoro-1-methyl-6-(thiophene-2-sulfonamido)-2,3-dihydro-1H-1,3-benzodiazol-5-yl]-N-methylprop-2-enamide | 396.47 |
| 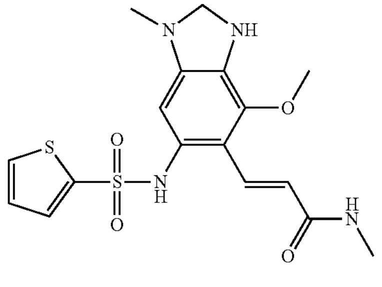 [SMILES: CNC(=O)/C=C/c1c(NS(=O)(=O)c2cccs2)cc2c(c1OC)NCN2C] | 185 | (2E)-3-[4-methoxy-1-methyl-6-(thiophene-2-sulfonamido)-2,3-dihydro-1H-1,3-benzodiazol-5-yl]-N-methylprop-2-enamide | 408.50 |
| 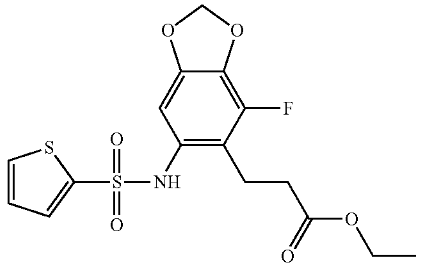 [SMILES: CCOC(=O)CCc1c(NS(=O)(=O)c2cccs2)cc2c(c1F)OCO2] | 186 | ethyl 3-[4-fluoro-6-(thiophene-2-sulfonamido)-2H-1,3-benzodioxol-5-yl]propanoate | 401.44 |
| 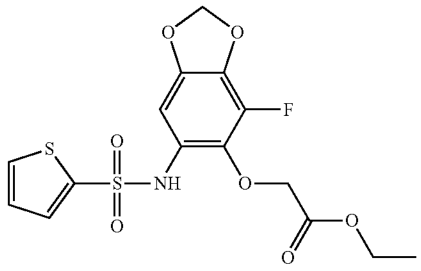 | 187 | ethyl 2-{[4-fluoro-6-(thiophene-2-sulfonamido)-2H-1,3-benzodioxol-5-yl]oxy}acetate | 403.41 |
| 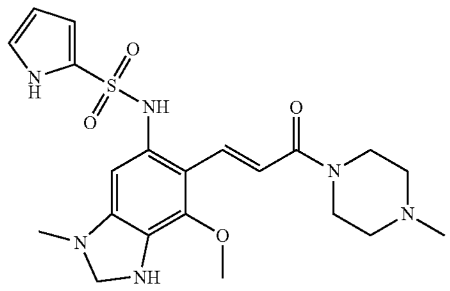 [SMILES: COc1c(/C=C/C(=O)N2CCN(C)CC2)c(NS(=O)(=O)c2ccc[nH]2)cc2c1NCN2C] | 188 | N-{7-methoxy-3-methyl-6-[(1E)-3-(4-methylpiperazin-1-yl)-3-oxoprop-1-en-1-yl]-2,3-dihydro-1H-1,3-benzodiazol-5-yl}-1H-pyrrole-2-sulfonamide | 460.56 |

TABLE 5-continued

| Analogs modeled from Second Series Hits | | | |
|---|---|---|---|
| Compound Structure | Cmpd. No. | IUPAC Name | MW |
| 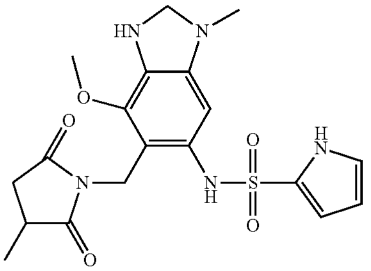 [SMILES: COc1c(CN2C(=O)CC(C)C2=O)c(NS(=O)(=O)c2ccc[nH]2)cc2c1NCN2C] | 189 | N-{7-methoxy-3-methyl-6-[(3-methyl-2,5-dioxopyrrolidin-1-yl)methyl]-2,3-dihydro-1H-1,3-benzodiazol-5-yl}-1H-pyrrole-2-sulfonamide | 433.49 |
| 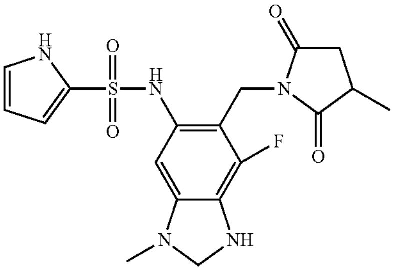 [SMILES: CC1CC(=O)N(Cc2c(NS(=O)(=O)c3ccc[nH]3)cc3c(c2F)NCN3C)C1=O] | 190 | N-{7-fluoro-3-methyl-6-[(3-methyl-2,5-dioxopyrrolidin-1-yl)methyl]-2,3-dihydro-1H-1,3-benzodiazol-5-yl}-1H-pyrrole-2-sulfonamide | 421.45 |

The table below shows results from a Proliferation Assay $IC_{50}$ data, pharmacokinetic (PK) and Surface Plasmon Resonance data for selected compounds.

Summary Table for CNKSR1 Inhibitors

| Properties of 7390 analogues | | | | | | |
|---|---|---|---|---|---|---|
| | In vitro $IC_{50}$ (μM) against mut-KRas NSCLC | | | | SPR | PK |
| Ana- | $2D^a$ | | $3D^b$ | | Kd | $T_{1/2}$ (hr)/AUC |
| logue | ave | range | ave | range | μM | (ng/mL/h) |
| 91 | 23 | 6.0-35 | | | 36 | 1.0/2.2 μM $C_{max}$ |
| 103 | 25 | 5.1-60 | | | ND | ND |
| 105 | 6.7 | 1.6-94 | | | 62 | ND |
| 106 | 16.3 | 0.8-100 | 8.4 | 0.096-75 | 33 | 1.7/7000 |
| 107 | 19.5 | 1.0-100 | 1.5 | 0.82-75 | 67 | 3.2/34,474 |
| 108 | 35 | 0.2-100 | | | >100 | 1.0/3,412 |
| 109 | 18.9 | 0.1-100 | | | 75 | 0.75/1,195 |
| 110 | 15.7 | 4.3-100 | 1.2 | 0.23-75 | <50 | ND |
| 111 | 19.2 | 0.6-100 | 4.1 | 0.12-13.2 | 25 | 1.0/29,972 |
| 112 | 65 | 19-100 | | | <50 | ND |
| 113 | 25 | 13.7-100 | | | 36 | ND |
| 114 | 57 | 12.1-100 | | | >100 | ND |
| 115 | 11.2 | 1.6-100 | | | >100 | ND |
| 151 | 18 | 0.5-100 | 0.69 | 0.025-2.7 | 7.9 | 0.5/NA (rapid metabolism) |
| 152 | 20 | 0.1-100 | 0.27 | 0.015-0.26 | 39 | 3.1/7000 |

[a]$IC_{50}$ mean of 12 mut-KRas NSCLC lines/range across mut-Kras cell lines (μM)
[b]$IC_{50}$ mean of 6 mut-KRas NSCLC lines/range across mut-Kras cell lines (μM)

While preferred embodiments have been shown and described herein, numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby. Throughout the above specification a number of references have been cited and or referred to it is to be understood that unless specifically noted, all references cited in the above specification and or referred to in the above specification are hereby incorporated by reference in their entirety.

What is claimed is:

1. A compound or a pharmaceutically acceptable salt or a stereoisomer according to Formula I:

Formula I

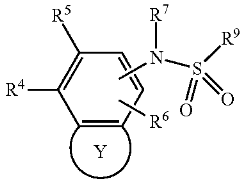

wherein

Y is an optionally substituted heterocycle selected from the group consisting of

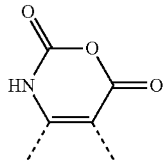,
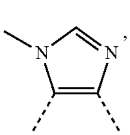,
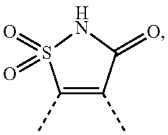,

-continued

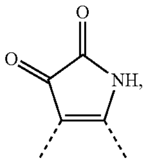 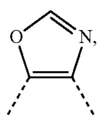 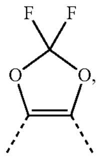

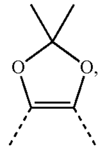 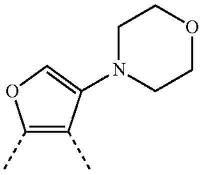 ,

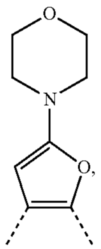 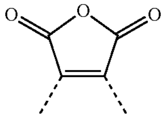 and

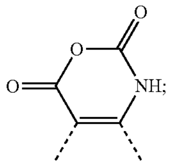

$R^4$ is hydrogen, halogen, hydroxy, —$C_1$-$C_4$ alkyl, —$C_1$-$C_4$ alkoxy, —$C_1$-$C_4$ perfluoroalkyl or optionally substituted $C_3$-$C_{10}$ heterocycle;

$R^5$ is —$C_1$-$C_4$ alkyl-OH, —$C_1$-$C_4$alkyl$R^8$, —$C_2$-$C_6$ alkenyl-OH, $C_1$-$C_4$ alkyl-$CO_2R^8$, $C_1$-$C_4$ alkenyl-$CO_2R^8$, —$C_1$-$C_4$ alkyl-C(O)—$C_1$-$C_4$ alkyl, —$C_2$-$C_6$ alkenyl-C(O)—$C_1$-$C_4$ alkyl, —$C_1$-$C_4$ alkyl-C(O)—$C_3$-$C_5$ cycloalkyl, —$C_2$-$C_6$ alkenyl-C(O)—$C_3$-$C_5$ cycloalkyl, NH—$SO_2$—$C_3$-$C_{10}$heteroaryl, C(O)—$C_2$-$C_6$alkenyl$R^8$,

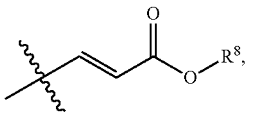 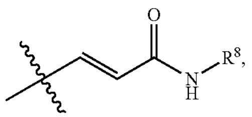

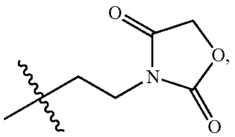 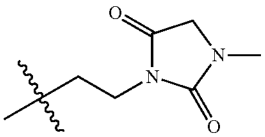

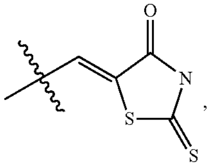 , 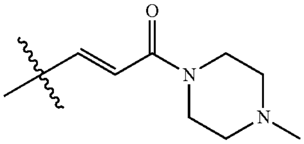 ,

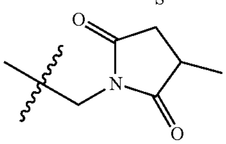 , 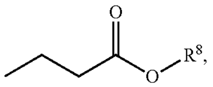

-continued

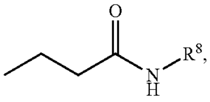 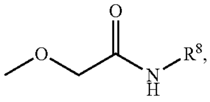

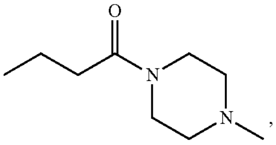 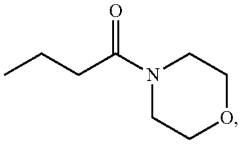

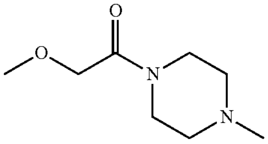 or

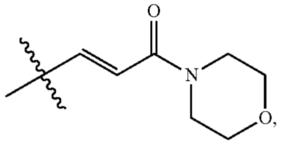

wherein $R^4$ and $R^5$ may be taken together to form a 5-10 membered, saturated, partially unsaturated or fully unsaturated heterocyclyl ring;

$R^6$ is hydrogen or —$C_1$-$C_4$alkoxy;

$R^7$ is -hydrogen or

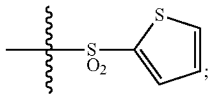 [SMILES: *S(=O)(=O)c1cccs1]

$R^8$, if present, is hydrogen, optionally substituted —$C_1$-C4 alkyl, —$C_3$-$C_5$ cycloalkyl or —$C_3$-$C_{10}$ heterocyclyl, wherein the —$C_1$-$C_4$ alkyl may be optionally substituted with —OH, —$C_3$-$C_{10}$heterocycle or —$C_3$-$C_{10}$ heteroaryl; and $R^9$ is optionally substituted $C_3$-$C_{10}$ aryl or optionally substituted $C_3$-$C_{10}$ heteroaryl.

2. The compound of claim 1 wherein $R^4$ is fluoro, methoxy or perfluoromethoxy.

3. The compound of claim 1, wherein $R^5$ is

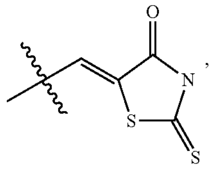 , 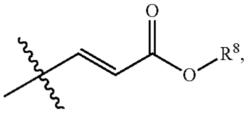

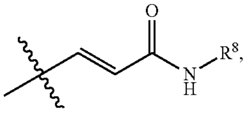

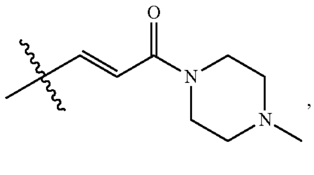 , 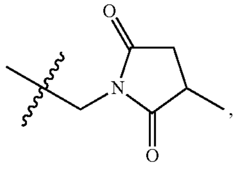 ,

-continued

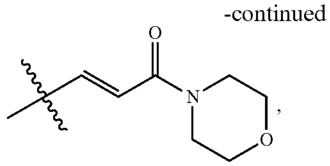

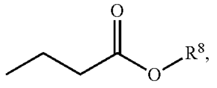

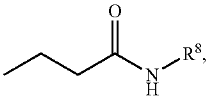

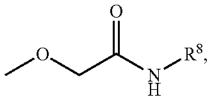

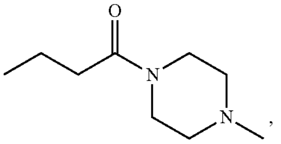

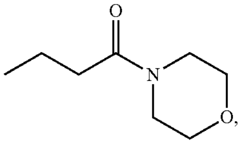

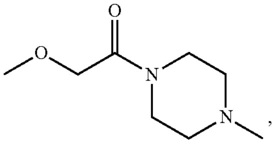

C(O)—$C_2$-$C_6$alkenyl$R^8$ or —$C_2$-$C_6$ alkenyl-OH, when $R^5$ is

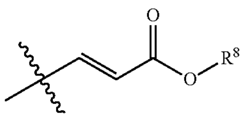

or —$C_2$-$C_6$ alkenyl-OH then

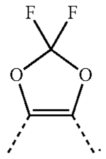

4. The compound of claim 1, wherein $R^4$ and $R^5$ taken together form

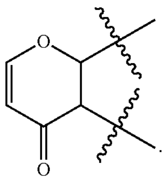 [SMILES: *C1OC=CC(=O)C1*]

5. The compound of claim 1, wherein $R^6$ is hydrogen or methoxy.

6. The compound of claim 1, wherein $R^7$ is hydrogen.

7. The compound of claim 1, wherein $R^8$ is hydrogen, methyl, ethyl, 2-hydroxypropyl, cyclopropyl, furan, methylfuran, methyl pyrrole, methylmorpholine, methylisoxazole or methyloxazole.

8. The compound of claim 1, wherein $R^9$ is optionally substituted phenyl, pyridine, pyrrole, thiophene, thiazole, oxazole, isoxazole, imidazole, indole or benzofuran.

9. The compound of claim 1 of the Formula:

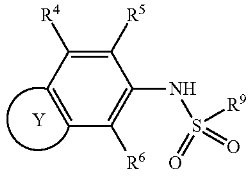

wherein $R^5$ is

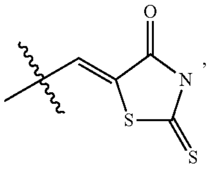

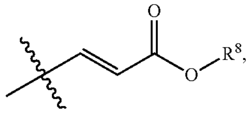

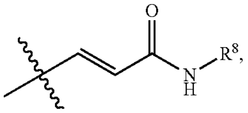

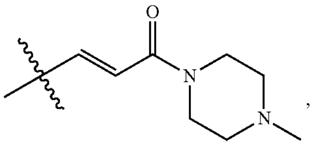

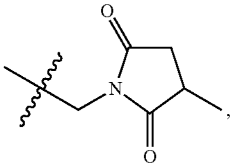

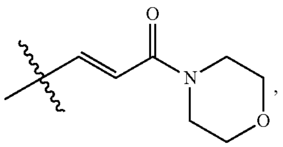

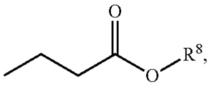

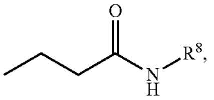

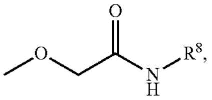

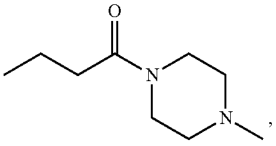

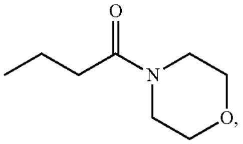

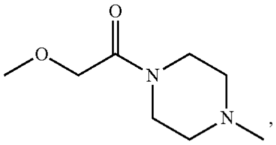

C(O)—$C_2$-$C_6$alkenyl$R^8$ or —$C_2$-$C_6$ alkenyl-OH, when $R^5$ is

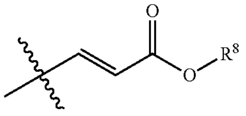

or —$C_2$-$C_6$ alkenyl-OH then

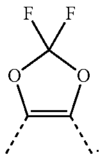

10. The compound of claim 9 wherein $R^4$ is fluoro, methoxy or perfluoromethoxy.

11. The compound of claim 9, wherein $R^4$ and $R^5$ taken together form

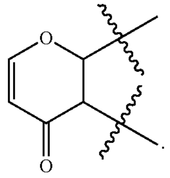 [SMILES: *C1OC=CC(=O)C1*]

12. The compound of claim 9, wherein $R^6$ is hydrogen or methoxy.

13. The compound of claim 9, wherein $R^8$ is hydrogen, methyl, ethyl, 2-hydroxypropyl, cyclopropyl, furan, methylfuran, methyl pyrrole, methylmorpholine, methylisoxazole or methyloxazole.

14. The compound of claim 9, wherein $R^9$ is optionally substituted phenyl, pyridine, pyrrole, thiophene, thiazole, oxazole, isoxazole, imidazole, indole or benzofuran.

15. The compound of claim 1, according to Formula IV:

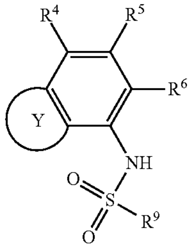

wherein $R^5$ is

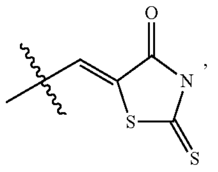
,
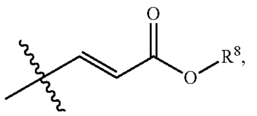

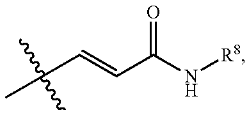

-continued

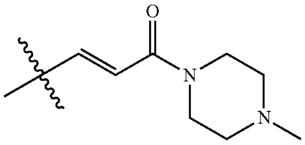
,
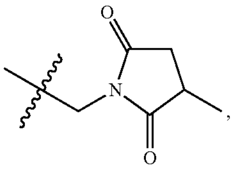
,

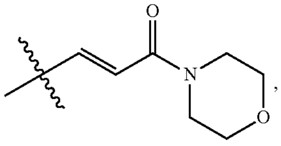
,
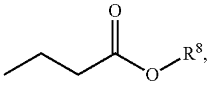

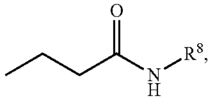

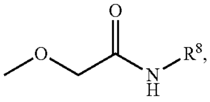

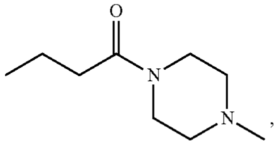
,
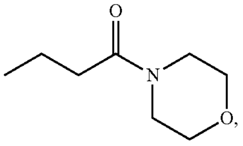

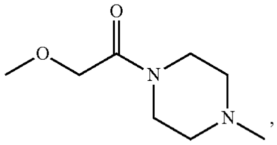
,

C(O)—$C_2$-$C_6$alkenyl$R^8$ or —$C_2$-$C_6$ alkenyl-OH, when $R^5$ is

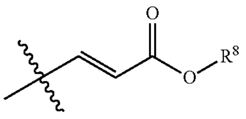

or —$C_2$-$C_6$ alkenyl-OH then

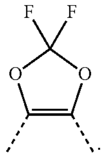

16. The compound of claim 15, wherein $R^4$ is fluoro, methoxy or perfluoromethoxy.

17. The compound of claim 15, wherein $R^4$ and $R^5$ taken together form

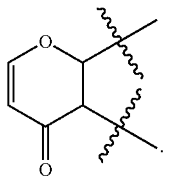 [SMILES: *C1OC=CC(=O)C1*]

18. The compound of claim 15, wherein $R^6$ is hydrogen or methoxy.

19. The compound of claim 15, wherein $R^8$ is hydrogen, methyl, ethyl, 2-hydroxypropyl, cyclopropyl, furan, methylfuran, methyl pyrrole, methylmorpholine, methylisoxazole or methyloxazole.

20. The compound of claim 15, wherein $R^9$ is optionally substituted phenyl, pyridine, pyrrole, thiophene, thiazole, oxazole, isoxazole, imidazole, indole or benzofuran.

21. The compound of claim 1 selected from the group consisting of:

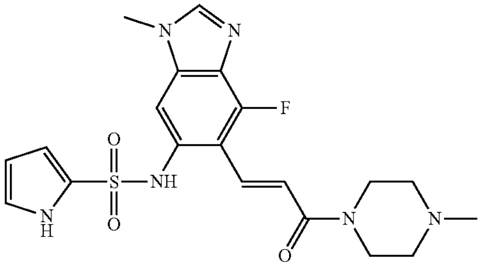
,

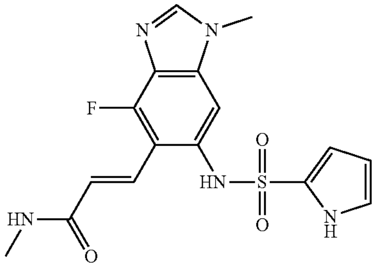
,

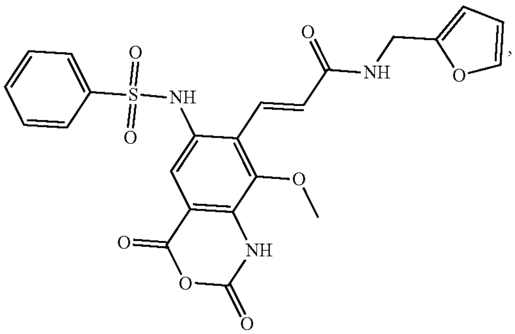
,

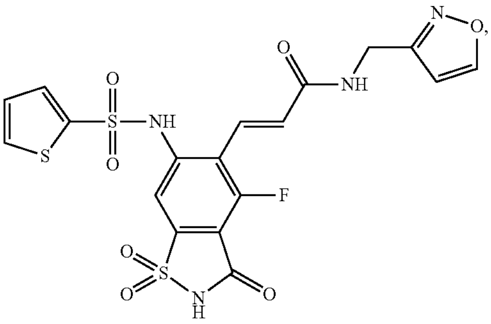
,

-continued

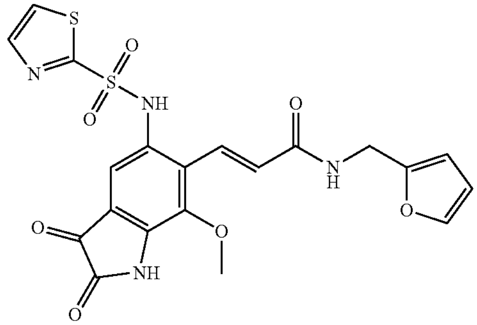
,

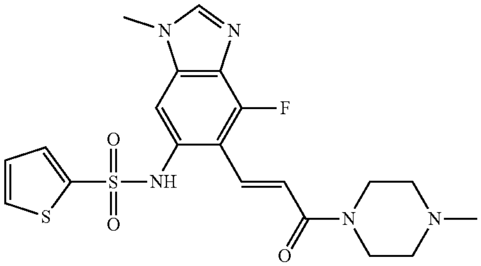
,

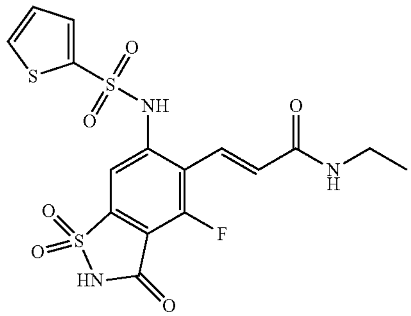
,

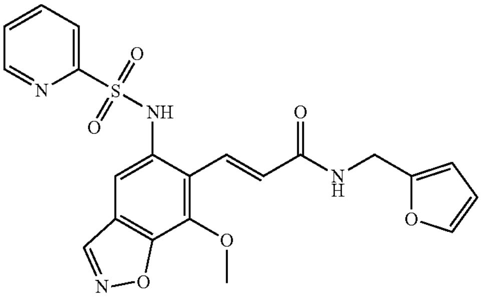
,

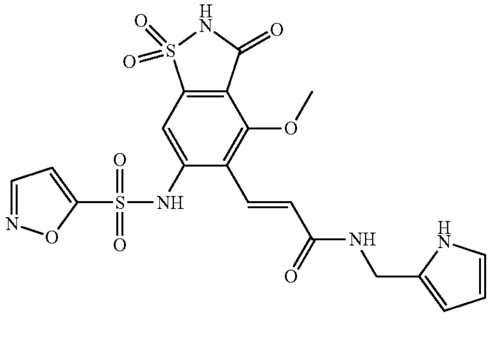
,

-continued
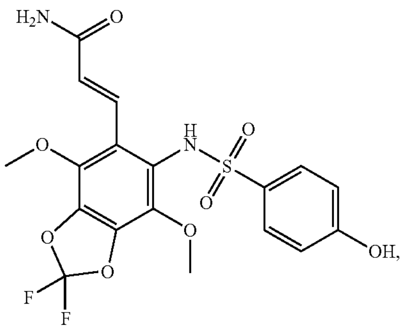
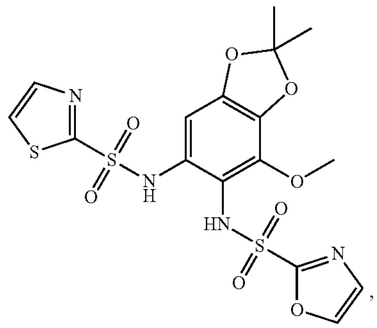
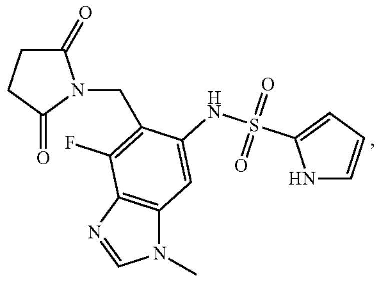
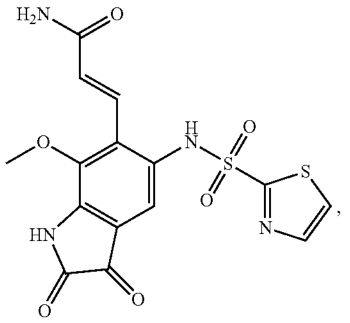
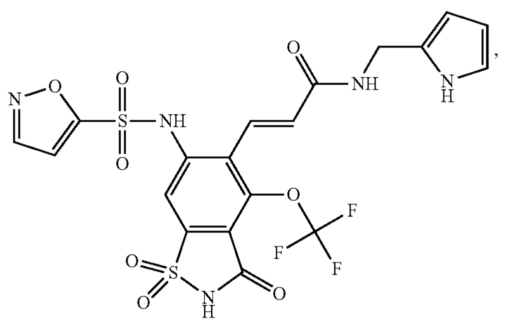
-continued
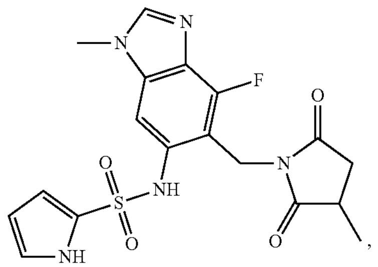
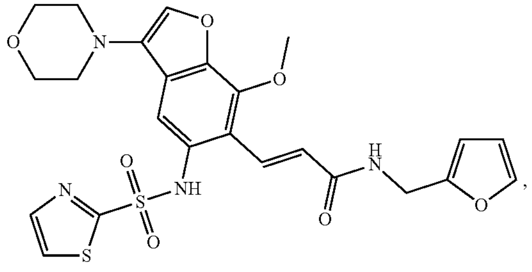
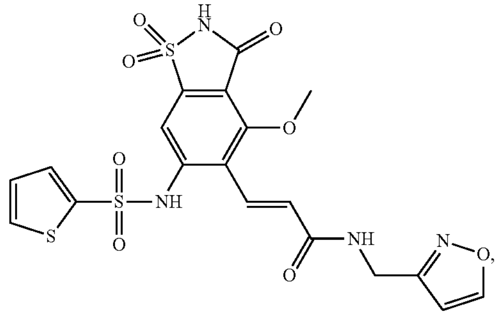
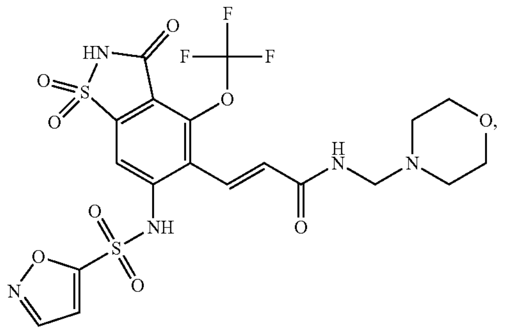
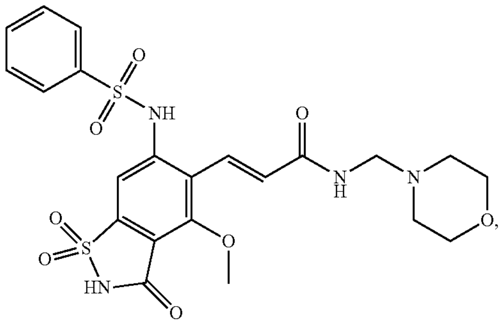

-continued
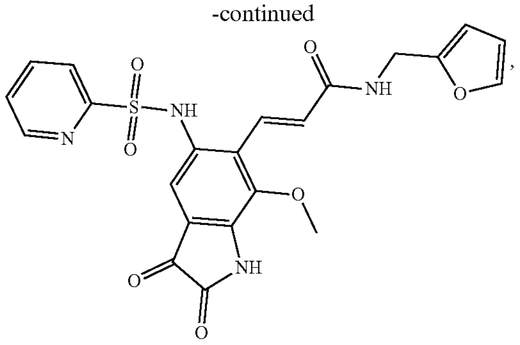
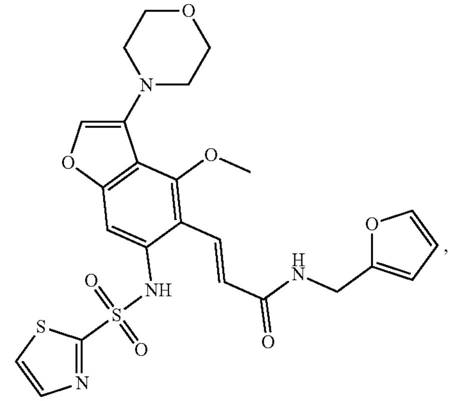
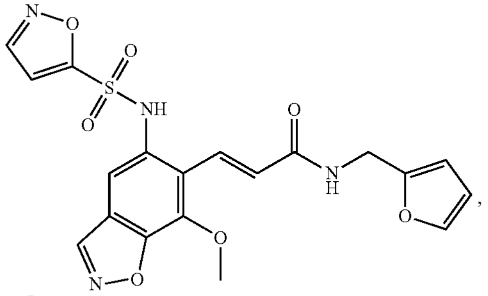
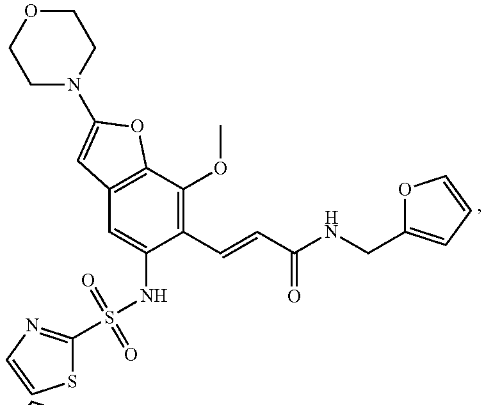
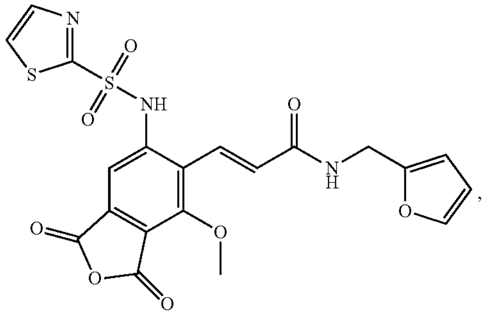
-continued
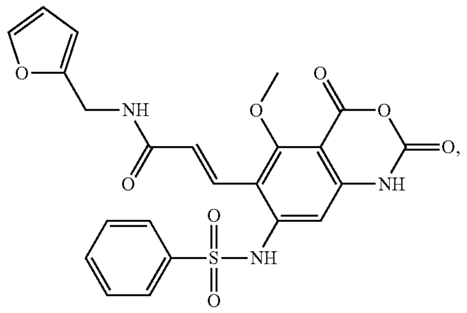
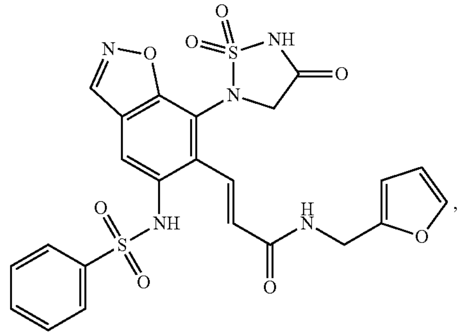
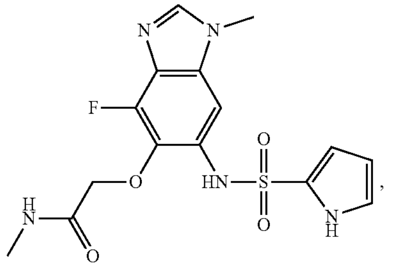
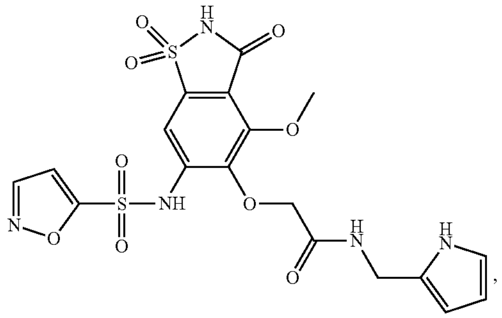
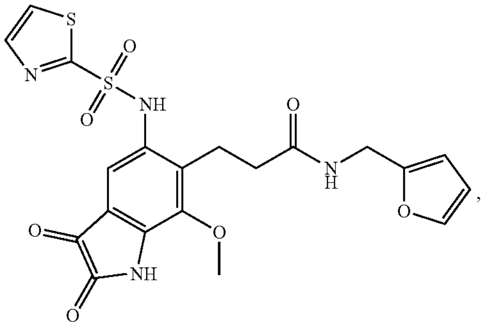

-continued
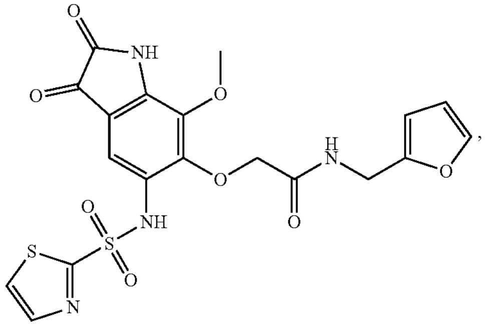
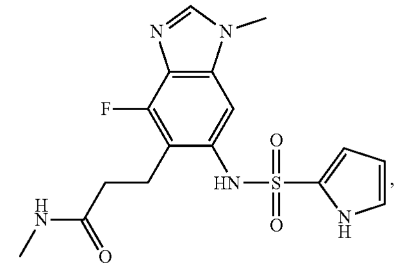
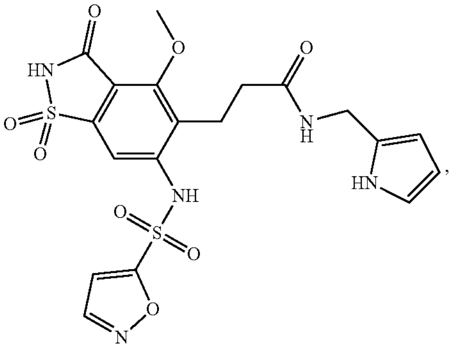
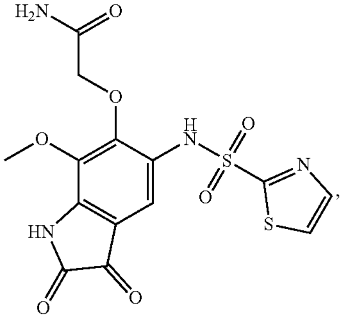
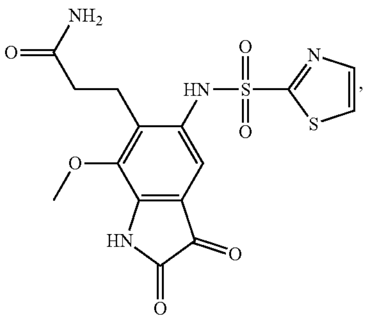
-continued
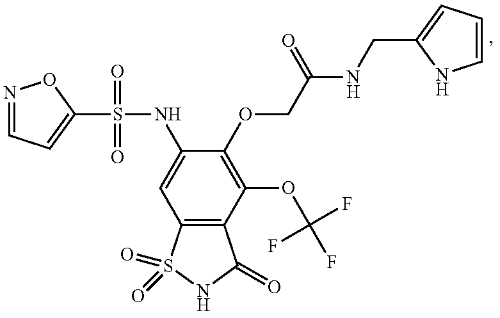
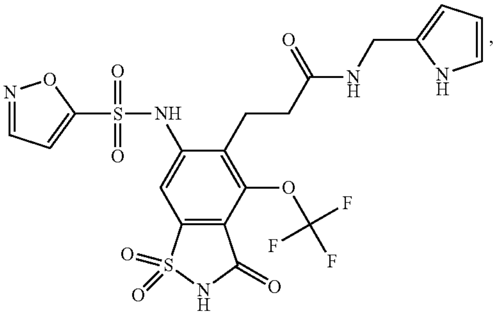
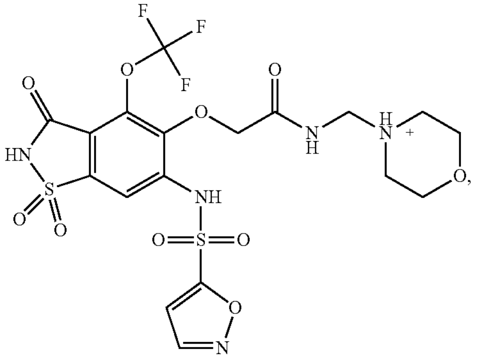
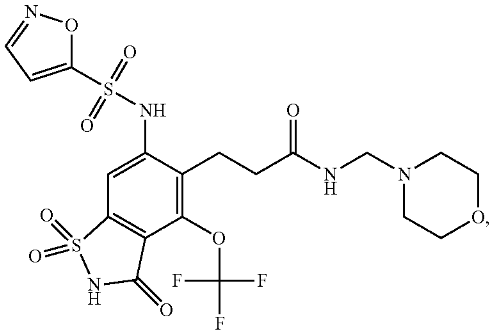
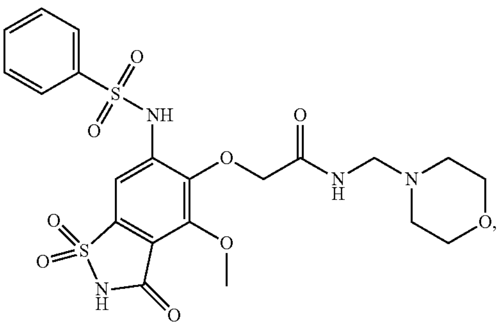

-continued
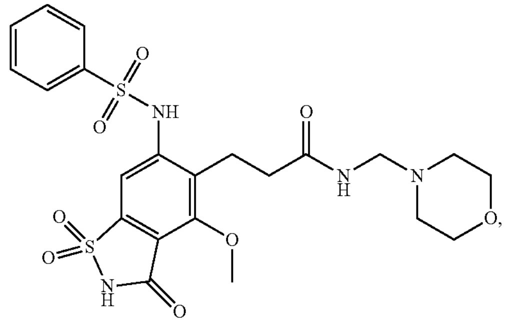
,
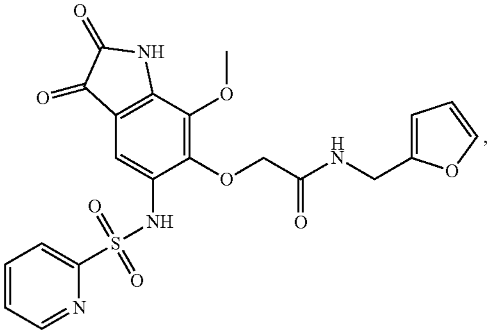
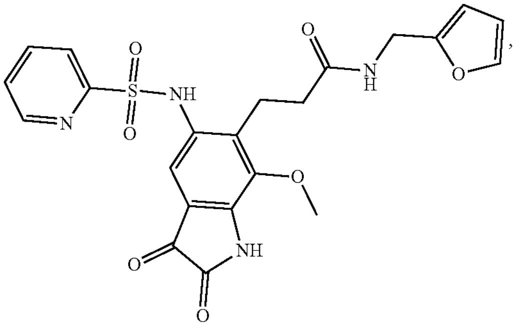
,
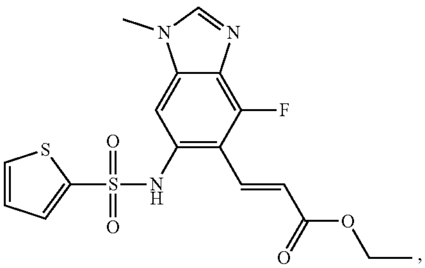
,
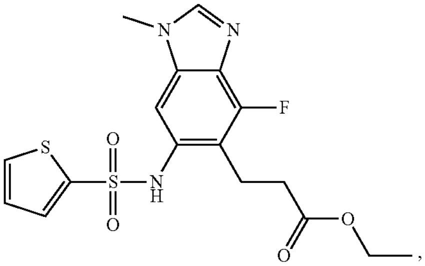
,
-continued
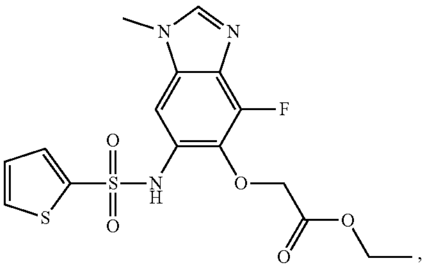
,
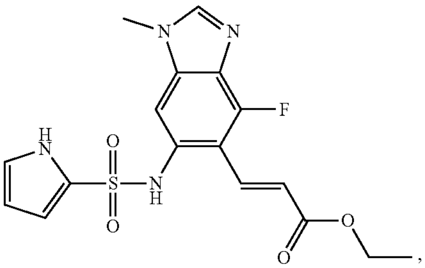
,
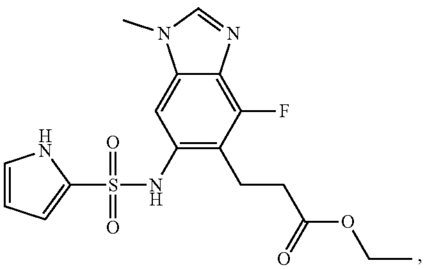
,
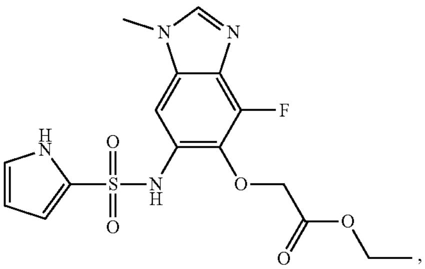
,
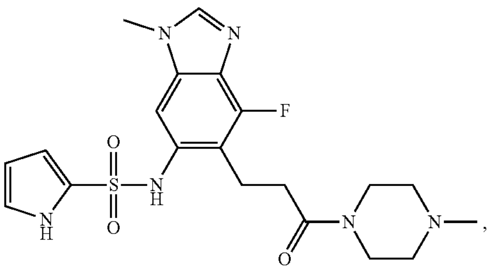
,
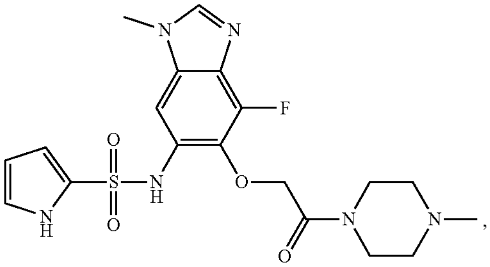
, -continued

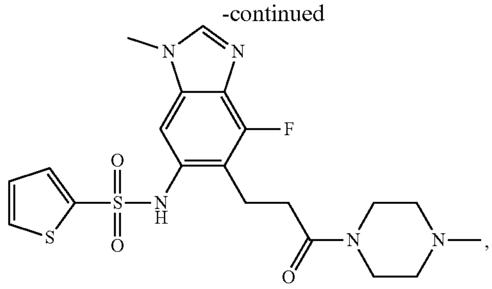

and

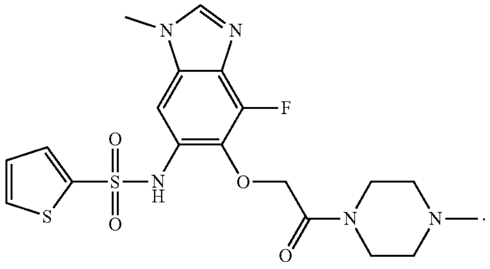

22. A pharmaceutical composition, comprising a therapeutically effective amount of a compound according to claim 1 and a pharmaceutically acceptable carrier or diluent.

23. A method of treating cancer in a patient in need thereof comprising administering to the patient a therapeutically effective amount of a compound according to claim 1, wherein the cancer is selected from colon cancer, lung cancer, pancreatic cancer, and combinations thereof.

24. The method of claim 23, wherein the cancer is colon cancer.

25. The method of claim 23, wherein the cancer is pancreatic cancer.

26. The method of claim 23, wherein the cancer is non-small cell lung cancer.

27. A method of inhibiting CNKSR1 in a patient in need thereof, comprising administering to the patient, an effective amount of a compound according to claim 1.

28. A compound or a pharmaceutically acceptable salt or a stereoisomer according to the Formula:

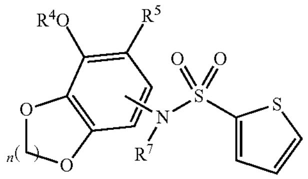

wherein $R^4$ is —H, —$C_1$-$C_4$ alkyl;

$R^5$ is

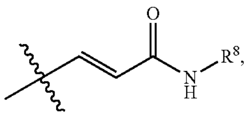

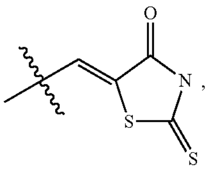

-continued

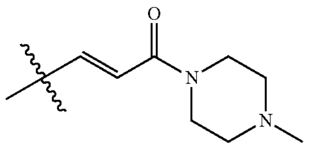

or

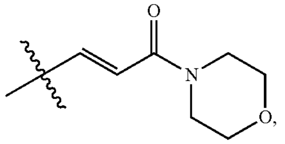

wherein $R^4$ and $R^5$ may be taken together to form a 5-10 membered, saturated, partially unsaturated or fully unsaturated heterocyclyl ring;

$R^8$ is H, optionally substituted —$C_1$-$C_4$ alkyl, —$C_3$-$C_5$ cycloalkyl or —$C_3$-$C_{10}$ heterocyclyl, wherein the —$C_1$-$C_4$ alkyl may be optionally substituted with —OH or —$C_3$-$C_{10}$ heteroaryl;

$R^7$ is —H or

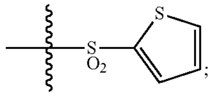 [SMILES: *S(=O)(=O)c1cccs1]

and n is 1 or 2.

29. A pharmaceutical composition, comprising a therapeutically effective amount of a compound according to claim 28 and a pharmaceutically acceptable carrier or diluent.

30. A compound or a pharmaceutically acceptable salt or a stereoisomer thereof, selected from the group consisting of:

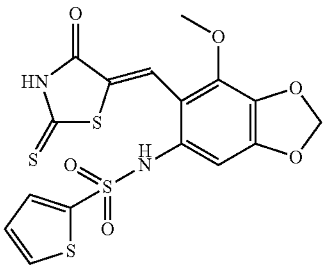

,

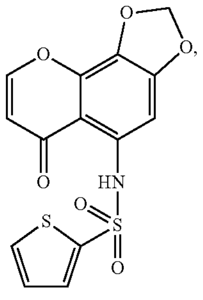

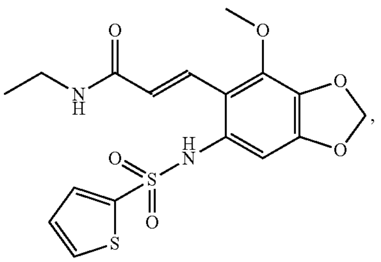

-continued

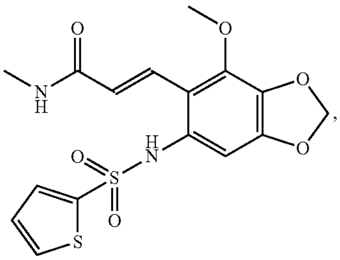

,

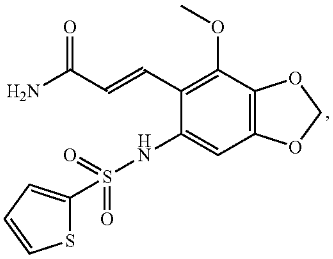

,

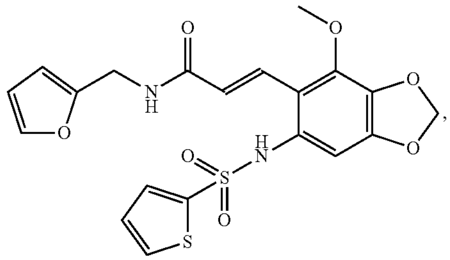

,

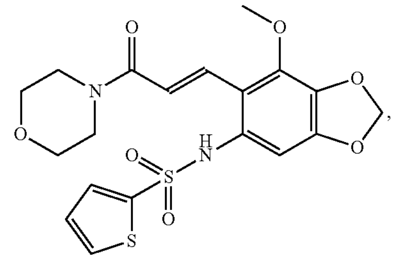

,

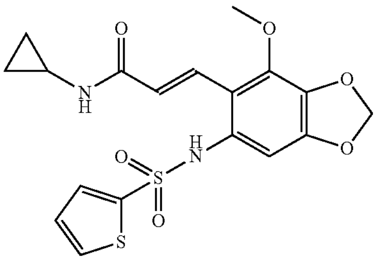

,

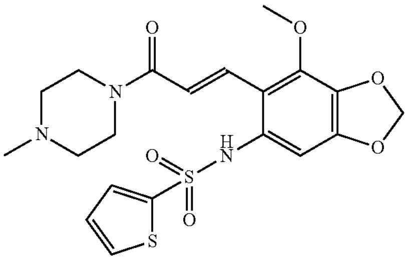

,

-continued

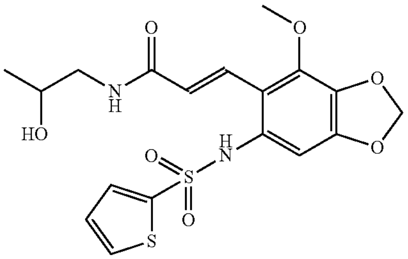

,

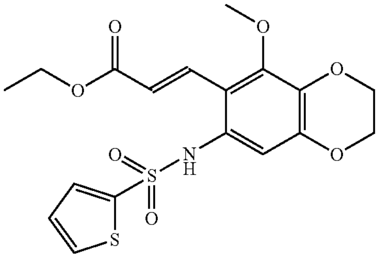

,

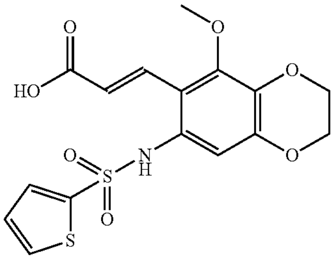

, and

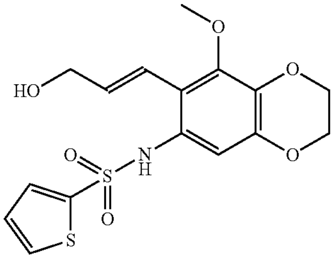

.

31. A method of treating cancer in a patient in need thereof comprising administering to the patient a therapeutically effective amount of a compound according to claim 28, wherein the cancer is selected from colon cancer, lung cancer, pancreatic cancer, and combinations thereof.

32. A method of inhibiting CNKSR1 in a patient in need thereof comprising administering to the patient, an effective amount of a compound according to claim 28.

33. A compound or a pharmaceutically acceptable salt or a stereoisomer according to Formula I:

Formula I

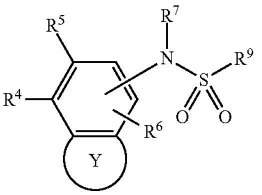

wherein

Y is a heterocycle of the Formula:

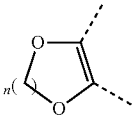

wherein n is 1 or 2;

$R^4$ is, halogen, hydroxy, —$C_1$-$C_4$ alkyl, —$C_1$-$C_4$ alkoxy, —$C_1$-$C_4$ perfluoroalkyl or optionally substituted $C_3$-$C_{10}$ heterocycle;

$R^5$ is —$C_1$-$C_4$ alkyl-OH, —$C_1$-$C_4$alkylR$^8$, —$C_2$-$C_6$ alkenyl-OH, $C_1$-$C_4$ alkyl-$CO_2R^8$, $C_1$-$C_4$ alkenyl-$CO_2R^8$, —$C_1$-$C_4$ alkyl-C(O)—$C_1$-$C_4$ alkyl, —$C_2$-$C_6$ alkenyl-C(O)—$C_1$-$C_4$ alkyl, —$C_1$-$C_4$ alkyl-C(O)—$C_3$-$C_5$ cycloalkyl, —$C_2$-$C_6$ alkenyl-C(O)—$C_3$-$C_5$ cycloalkyl, NH—$SO_2$—$C_3$-$C_{10}$heteroaryl, C(O)—$C_2$-$C_6$alkenylR$^8$,

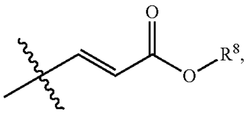

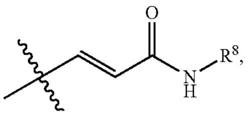

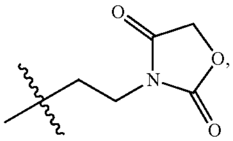

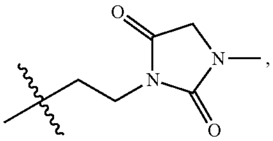

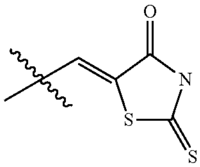,

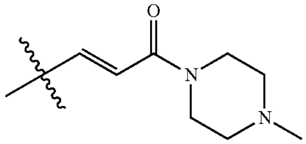,

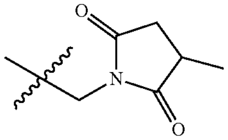,

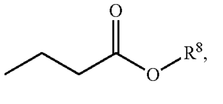

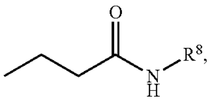

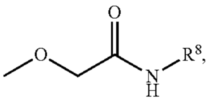

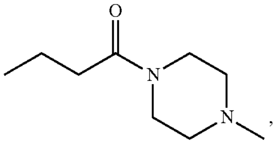,

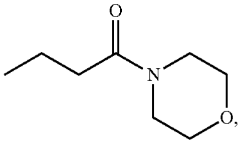

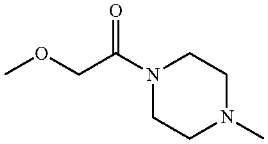 or

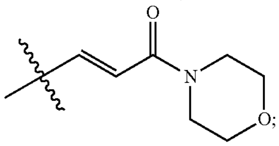

wherein $R^4$ and $R^5$ may be taken together to form a 5-10 membered, saturated, partially unsaturated or fully unsaturated heterocyclyl ring;

$R^6$ is hydrogen or —$C_1$-$C_4$alkoxy;

$R^7$ is -hydrogen or

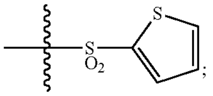 [SMILES: *S(=O)(=O)c1cccs1];

$R^8$, if present, is hydrogen, optionally substituted —$C_1$-$C_4$ alkyl, —$C_3$-$C_5$ cycloalkyl or —$C_3$-$C_{10}$ heterocyclyl, wherein the —$C_1$-$C_4$ alkyl may be optionally substituted with —OH, —$C_3$-$C_{10}$heterocycle or —$C_3$-$C_{10}$ heteroaryl; and $R^9$ is optionally substituted $C_3$-$C_{10}$ aryl or optionally substituted $C_3$-$C_{10}$ heteroaryl;

provided that $R^9$ is not thiophene when $R^4$ is hydroxy or —$C_1$-$C_4$ alkoxy.

34. A pharmaceutical composition, comprising a therapeutically effective amount of a compound according to claim 33 and a pharmaceutically acceptable carrier or diluent.

35. A compound or a pharmaceutically acceptable salt or a stereoisomer thereof, selected from the group consisting of

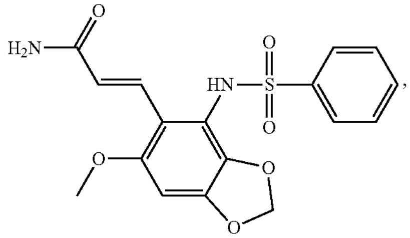,

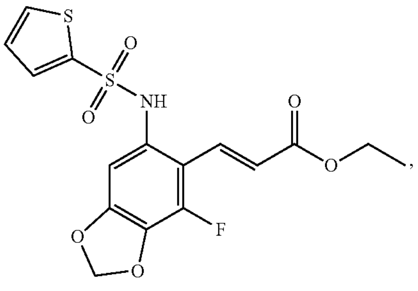,

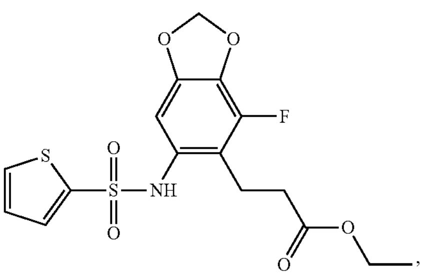,

-continued

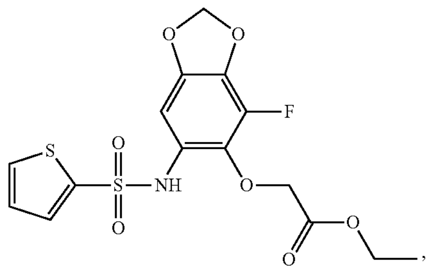

,

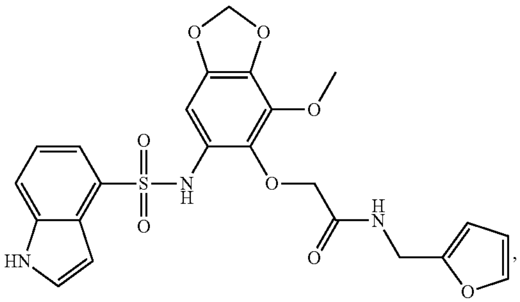

,

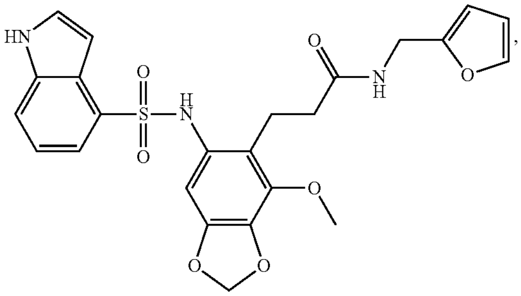

,

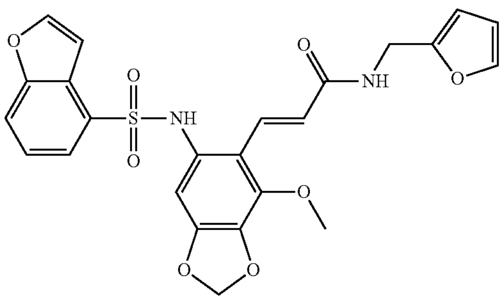

,

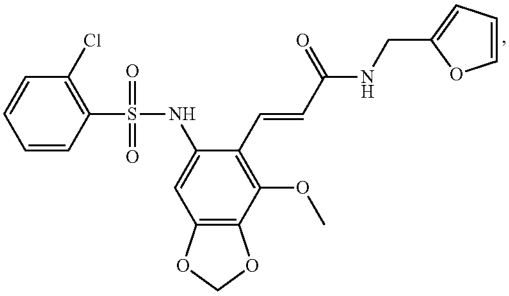

, and

-continued

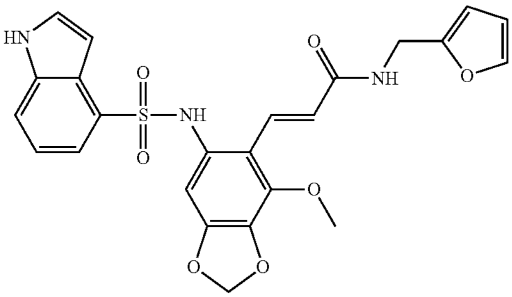

.

36. A method of treating cancer in a patient in need thereof comprising administering to the patient a therapeutically effective amount of a compound according to claim 33, wherein the cancer is selected from colon cancer, lung cancer, pancreatic cancer; and combinations thereof.

37. A compound or a pharmaceutically acceptable salt or a stereoisomer thereof, selected from the group consisting of:

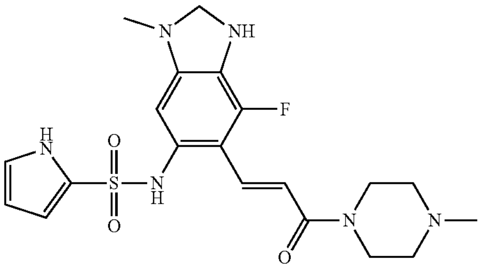

,

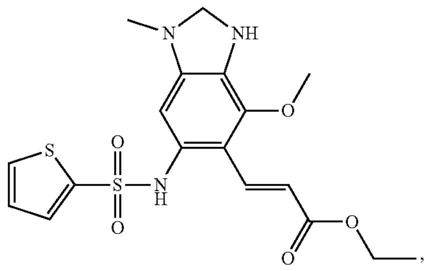

,

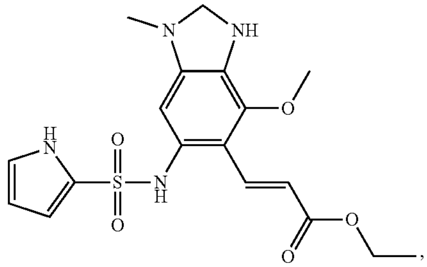

,

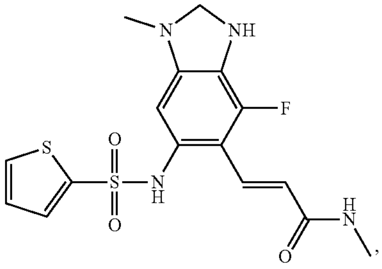

,

-continued
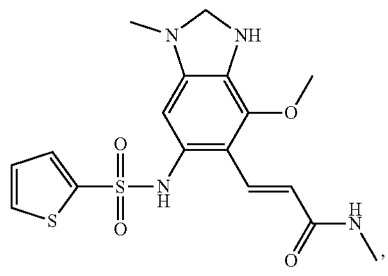
,
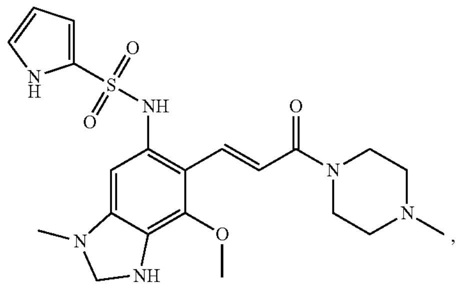
,
-continued
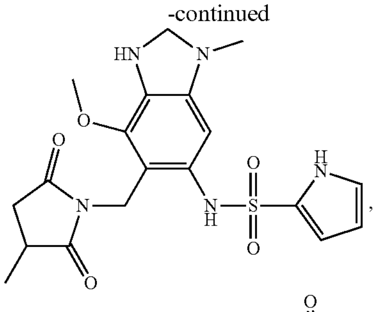
, and
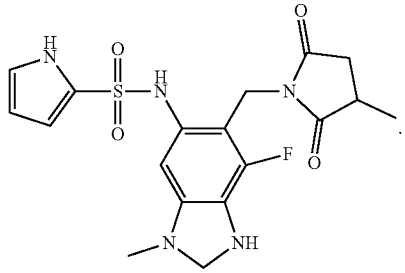
.
* * * * *